US011534500B2

(12) United States Patent
Nash et al.

(10) Patent No.: US 11,534,500 B2
(45) Date of Patent: Dec. 27, 2022

(54) MODIFIED UBE3A GENE FOR A GENE THERAPY APPROACH FOR ANGELMAN SYNDROME

(71) Applicant: University of South Florida, Tampa, FL (US)

(72) Inventors: Kevin Ron Nash, Seffner, FL (US); Edwin John Weeber, Apollo Beach, FL (US); Jennifer Leigh Daily, New York, NY (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/805,442

(22) Filed: Nov. 7, 2017

(65) Prior Publication Data

US 2018/0104358 A1    Apr. 19, 2018

Related U.S. Application Data

(63) Continuation of application No. PCT/US2016/031468, filed on May 9, 2016.

(60) Provisional application No. 62/158,269, filed on May 7, 2015.

(51) Int. Cl.
| | |
|---|---|
| *A61K 48/00* | (2006.01) |
| *C12N 15/52* | (2006.01) |
| *C12N 15/864* | (2006.01) |
| *C12N 9/10* | (2006.01) |
| *C12N 9/00* | (2006.01) |
| *C12N 15/85* | (2006.01) |

(52) U.S. Cl.
CPC ............ *A61K 48/005* (2013.01); *C12N 9/104* (2013.01); *C12N 9/93* (2013.01); *C12N 15/52* (2013.01); *C12N 15/85* (2013.01); *C12Y 203/02* (2013.01); *C12Y 603/02019* (2013.01); *C07K 2319/01* (2013.01); *C07K 2319/02* (2013.01); *C07K 2319/036* (2013.01); *C07K 2319/10* (2013.01); *C12N 2750/14143* (2013.01)

(58) Field of Classification Search
CPC combination set(s) only.
See application file for complete search history.

(56) References Cited

U.S. PATENT DOCUMENTS

| | | | |
|---|---|---|---|
| 6,468,754 B1 | 10/2002 | Greene et al. | |
| 6,706,505 B1 * | 3/2004 | Han | C07H 21/04 435/183 |
| 2006/0002946 A1 | 1/2006 | Gallichan et al. | |
| 2006/0062772 A1 | 3/2006 | Keegan et al. | |
| 2013/0058915 A1 | 3/2013 | Greenberg et al. | |
| 2013/0317018 A1 | 11/2013 | Philpot et al. | |
| 2015/0010578 A1 | 1/2015 | Balazs et al. | |
| 2015/0361148 A1 * | 12/2015 | Haque | C12N 15/85 435/32 |
| 2017/0088593 A1 * | 3/2017 | Ildefonso | C07K 14/4702 |

FOREIGN PATENT DOCUMENTS

| | | | | |
|---|---|---|---|---|
| EP | 2703487 A1 | 3/2014 | | |
| EP | 2724721 A1 | 4/2014 | | |
| JP | 2007535898 A | 12/2007 | | |
| WO | WO-9534670 A2 * | 12/1995 | ............. | A61P 25/28 |
| WO | 0192582 A1 | 12/2001 | | |
| WO | 03088916 A2 | 10/2003 | | |
| WO | 2005084714 A2 | 9/2005 | | |
| WO | WO-2005084714 A2 * | 9/2005 | ............. | C12N 15/86 |
| WO | 2012064806 A2 | 5/2012 | | |
| WO | WO-2013016279 A1 * | 1/2013 | ......... | A01K 67/0278 |
| WO | 2014004572 A2 | 1/2014 | | |

OTHER PUBLICATIONS

Jin et al., Transduction of Human Catalase Mediated by an HIV-1 TAT Protein Basic Domain and Arginine-Rich Peptides Into Mammalian Cells. Free Radical Biology & Medicine, vol. 31, No. 11, pp. 1509-1519, 2001 (Year: 2001).*
Garg et al., The Hybrid Cytomegalovirus Enhancer/Chicken beta-Actin Promoter along with Woodchuck Hepatitis Virus Post-transcriptional Regulatory Element Enhances the Protective Efficacy of DNA Vaccines. The Journal of Immunology, 2004, 173: 550-558. (Year: 2004).*
Carty et al., Intracranial Injection of AAV Expressing NEP but Not IDE Reduces Amyloid Pathology in APP+PS1 Transgenic Mice. PLoS One. 2013; 8(3): e59626 (Year: 2013).*
Burger et al., Systemic Mannitol-Induced Hyperosmolality Amplifies rAAV2-Mediated Striatal Transduction to a Greater Extent Than Local Co-infusion (Mol Ther, 2005, 11:327-331) (Year: 2005).*
Geng et al., Sorting Protein-related Receptor SorLA Controls Regulated Secretion of Glial Cell Line-derived Neurotrophic Factor (JBC, 2011,48:41871-41882) (Year: 2011).*
Wakamatsu et al., (GenBank Acc No. AK291405, Direct submission Oct. 9, 2007, p. 1-2), (Year: 2007).*

(Continued)

*Primary Examiner* — Arthur S Leonard
(74) *Attorney, Agent, or Firm* — Michele L. Lawson; Smith & Hopen, P.A.

(57) ABSTRACT

Angelman Syndrome (AS) is a genetic disorder occurring in approximately one in every 15,000 births. It is characterized by severe mental retardation, seizures, difficulty speaking and ataxia. The gene responsible for AS was discovered to be UBE3A and encodes for E6-AP, an ubiquitin ligase. A unique feature of this gene is that it undergoes maternal imprinting in a neuron-specific manner. In the majority of AS cases, there is a mutation or deletion in the maternally inherited UBE3A gene, although other cases are the result of uniparental disomy or mismethylation of the maternal gene. While most human disorders characterized by severe mental retardation involve abnormalities in brain structure, no gross anatomical changes are associated with AS. We have generated a Ube3a protein with additional sequences that should allow the secretion from cells and uptake by neighboring neuronal cells. This would confer a functional E6-AP protein into the neurons and rescue disease pathology.

16 Claims, 18 Drawing Sheets

Specification includes a Sequence Listing.

(56) References Cited

OTHER PUBLICATIONS

Kaplan, et al., Clinical heterogeneity associated with deletions in the long arm of chromosome 15: report of 3 new cases and their possible significance. Am J Med Genet. Sep. 1987; 28(1):45-53.
Buiting, et al., Inherited microdeletions in the Angelman and Prader-Willi syndromes define an imprinting centre on human chromosome 15. Nat Genet. Apr. 1995;9(4):395-400.
Gabriel, et al., A transgene insertion creating a heritable chromosome deletion mouse model of Prader-Willi and Angelman syndrome. Proc Natl Acad Sci U.S.A. Aug. 1999;96(16):9258-63.
Knoll, et al., Angelman and Prader-Willi syndromes share a common chromosome 15 deletion but differ in parental prigin of the deletion. Am J Med Genet. 1989 Fed;32(2):285-90.
Malcolm, et al., Uniparental paternal disomy in Angelman's syndrome. Lancet. Mar. 23, 1991;337(8743):694-7.
Greer, et al., The Angelman Syndrome protein Ube3A regulates synapse Development by ubiquitinating arc. Cell. Mar. 5, 2010;140(5): 704-16.
Jiang, et al., Mutation of the Angelman ubiquitin ligase in mice causes increased cytoplasmic p53 and deficits of contextual learning and long-term potentiation. Neuron. Oct. 1998;21(4):799-811.
Davies, et al., Imprinted gene expression in the brain. Neurosci Biobehav Rev. May 2005;29(3):421-430.
Mah et al. Dual vectors expressing murine factor VIII result in sustained correction of hemophilia A mice, Hum Gene Ther, Jan. 20, 2003, vol. 14, pp. 143-152.
Weeber, et al., Derangements of hippocampal calcium/calmodulin-dependent protein kinase II in a mouse model for Angelman mental retardation syndrome. J Neurosci. Apr. 2003;23(7):2634-44.
T. Kishino, M. Lalande, and J. Wagstaff. "UBE3A/E6-AP mutations cause Angelman syndrome." Nature genetics 15.1 (1997): 70-73.
T. Matsuura, J.S. Sutcliffe, P. Fang, R-J. Galjaard, Y-h. Jiang, C.S. Benton, J.M. Rommens, and A.L. Beaudet. "De novo truncating mutations in E6-AP ubiquitin-protein ligase gene (UBE3A) in Angelman syndrome." Nature genetics 15.1 (1997): 74-77.
U. Albrecht, J.S. Sutcliffe, B.M. Cattanach, C.V. Beechey, D. Armstrong, G. Eichele, and A.L. Beaudet. "Imprinted expression of the murine Angelman syndrome gene, Ube3a, in hippocampal and Purkinje neurons." Nature genetics 17.1 (1997): 75-78.
J.L. Daily, K. Nash, U. Jinwal, T. Golde, J. Rogers, M.M. Peters, R.D. Burdine, C. Dickey, J.L. Banko and E.J. Weeber. "Adeno-Associated Virus-Mediated Rescue of the Cognitive Defects in a Mouse Model for Angelman Syndrome." Ed. Harold A. Burgess. PLoS One 6.12 (2011): e27221. PMC. Web. Apr. 21, 2015.
International Search Report and Written Opinion issued by the International Searching Authority dated Sep. 30, 2016 for corresponding International Patent Application No. PCT/US2016/031468.
International Preliminary Report on Patentability issued by the International Bureau dated Nov. 16, 2017 for corresponding International Patent Application No. PCT/US2016/031468.
Daily, J.L. Efficacy of Increased Ube3a Protein Levels in the Bain in Rescuing the Phenotype of an Angelman Syndrome Mouse. Thesis, University of South Florida, Department of Molecular Pharmacology and Physiology, Aug. 1, 2012. pp. 1-132.
Satoh et al. Site-specific integration of an adeno-associated virus vector plasmid mediated by regulated expression of rep based on Cre-loxP recombination. J. Virol. Nov. 2000, vol. 74, pp. 10631-8.
Lodish et al. Section 7.1 DNA Cloning with Plasmid Vectors, Molecular Cell Biology 4th Ed., Ed. Lodish et al. Freeman, Jun. 1, 1999, pp. 1-7.
QIAprep Miniprep Handbook. QIAGEN, May 1, 2004, pp. 1-52.
Daily et al. Adeno-associated virus-mediated rescue of the cognitive defects in a mouse model for Angelman Syndrome, PLoS One, Dec. 9, 2011, vol. 6, e27221, pp. 1-7.
Extended European Search Report (EPO Form 1507S) dated Nov. 6, 2018 for corresponding European Patent Application No. 16790226.1.

Notification of First Office Action issued by the Chinese State Intellectual Property Office dated Jul. 15, 2020 for corresponding Chinese Patent Application No. 201680026461.3.
English Translation of Notification of First Office Action issued by the Chinese State Intellectual Property Office dated Jul. 15, 2020 for corresponding Chinese Patent Application No. 201680026461.3.
Search Report issued by the Chinese State Intellectual Property Office dated Jul. 15, 2020 for corresponding Chinese Patent Application No. 201680026461.3.
English Translation of Search Report issued by the Chinese State Intellectual Property Office dated Jul. 15, 2020 for corresponding Chinese Patent Application No. 201680026461.3.
Official Action issued by the Japanese Patent Office dated Mar. 3, 2020 for corresponding Japanese Patent Application No. 2017-556744.
English Notification of Reasons for Refusal dated Mar. 3, 2020 for corresponding Japanese Patent Application No. 2017-556744.
Daily, Jennifer L. Efficacy of Increased Ube3a Protein Levels in the Brain in Rescuing the Phenotype of an Angelman Syndrome Mouse. Graduate Theses and Dissertations. University of South Florida Scholar Commons, Jan. 2012; 1-119.
Genbank [online], Accession No. AK291405.1, 2008, [retrieved on Feb. 5, 2020], Retrieved from the Internet: URL https://www.ncbi.nlm.nih.gov/nuccore/AK291405. *Homo sapiens* cDNA FLJ77551 complete cds, highly similar to *Homo sapiens* ubiquitin protein ligase E3A (human papilloma virus E6-associated protein, Angelman syndrome) (UBE3A), transcript variant 1, mRNA.
Genbank [online], Accession No. AK292514.1, 2008, [retrieved on Feb. 5, 2020], Retrieved from the Internet: URL https://www.ncbi.nlm.nih.gov/nuccore/AK292514. *Homo sapiens* cDNA FLJ77614 complete cds, highly similar to *Homo sapiens* ubiquitin protein ligase E3A (human papilloma virus E6-associated protein, Angelman syndrome) (UBE3A), transcript variant 3, mRNA.
Carty, Nikisha et al. Intracranial Injection of AAV Expressing NEP but Not IDE Reduces Amyloid Pathology in APP+PS1 Transgenic Mice. PLoS One, Mar. 2013. vol. 8, Issue 3, pp. 1-13.
Wilhelm, Franziska et al. The human ubiquitin C promoter drives selective expression in principal neurons in the brain of a transgenic mouse line. Neurochemistry International 59 (2011), 976-980.
Communication pursuant to Article 94(3) EPC (EPO Form 2001) issued by the European Patent Office dated Mar. 13, 2020 for corresponding European Patent Application No. 167901226.1.
Flinterman, Marcella et al. Delivery of Therapeutic Proteins as Secretable TAT Fusion Products. The American Society of Gene Therapy. www.moleculartherapy.org, Feb. 2009. vol. 17, No. 2, 334-342. Published online Dec. 2, 2008. doi:10.1038/mt.2008.256.
Shen, Ying et al. Expressed Cell-penetrating Peptides Can Induce a Bystander Effect, but Passage Through the Secretory Pathway Reduces Protein Transduction Activity. Molecular Therapy, May 2011. vol. 19, No. 5, 903-912. Published online Dec. 21, 2010. doi:10.1038/mt.2010.283.
Genbank [online], Accession No. AAB69154, Jun. 10, 2016, [retrieved on Jul. 15, 2020], Retrieved from the Internet: URL http://www.ncibi.nlm.nih.gov/protein,AAB69154.1?report=genbank&log$=protalign&blast_rank=1&RID=GZEB4KD4014. E6-AP ubiquitin-protein ligase [*Homo sapiens*].
Genbank [online], Accession No. KM359881.1, Nov. 11, 2014, [retrieved on Jul. 15, 2020], Retrieved from the Internet: URL http://www.ncibi.nlm.nih.gov/nuccore/704001889. HIV-1 isolate MU012 from India tat protein (tat) gene, partial cds; and vpu protein (vpu) gene, complete cds.
Genbank [online], Accession No. AH005553.2, Jun. 10, 2016, [retrieved on Jul. 14, 2020], Retrieved from the Internet: URL http://www.ncibi.nlm.nih.gov/nuccore/AH005553. *Homo sapiens* chromosome 15 E6-AP ubiquitin-protein ligase (UBE3A) gene, complete cds.
Genbank [online], Accession No. AH002844, Jun. 10, 2016, [retrieved on Jul. 15, 2020], Retrieved from the Internet: URL http://www.ncibi.nlm.nih.gov/nucleotide/AH002844.2?report=genbank&log$=nuclalign&blast_rank=7&RID=GZD8EGYZ016&from=2424to=2495. *Homo sapiens* insulin (INS) gene, complete cds.
Genbank [online], Accession No. KF688150, Oct. 2, 2013, [retrieved on Jul. 15, 2020], Retrieved from the Internet: URL http://www.

(56) References Cited

OTHER PUBLICATIONS ncibi.nlm.nih.gov/nucleotide/KF688150.1?report=genbank&log$=nuclalign&blast_rank=1&RID=GZDJM3NV014. *Homo sapiens* monoclonal antibody CH40 light chain mRNA, partial cds.
Genbank [online], Accession No. AH003115, Oct. 2, 2013, [retrieved on Jul. 15, 2020], Retrieved from the Internet: URL http://www.ncibi.nlm.nih.gov/nucleotide/AH003115.2?report=genbank&log$=nuclalign&blast_rank=3&RID=GZCZ6Y1G014. *Homo sapiens* neurotrophic factor gene, complete cds.
Genbank [online], Accession No. NM_000462, Oct. 2, 2013, [retrieved on Jul. 14, 2020], Retrieved from the Internet: URL http://www.ncibi.nlm.nih.gov/nucleotide/NM_000462.5?report=genbank&log$=nuclalign&blast_rank=1&RID=GVMK143201R&from=29&to=5304. *Homo sapiens* ubiquitin protein ligase E3A (UBE3A), transcript variant 2, mRNA.
Genbank [online], Accession No. NP_032412, Jul. 12, 2020, [retrieved on Jul. 14, 2020], Retrieved from the Internet: URL http://www.ncibi.nlm.nih.gov/protein/NP_032412.3?report-genbank&log$=protalign&blast_rank=2&RID=GW4579W401R. insulin-1 preproprotein [Mus musculus].
Genbank [online], Accession No. U82122, Feb. 19, 1997, [retrieved on Jul. 14, 2020], Retrieved from the Internet: URL http://www.ncibi.nlm.nih.gov/nuccore/U82122.1?report-genbank. Mus musculus E6-AP ubiquitin-protein ligase (Ube3a) mRNA, complete cds.
Genbank [online], Accession No. NM_008386, Jul. 12, 2020, [retrieved on Jul. 14, 2020], Retrieved from the Internet: URL http://www.ncibi.nlm.nih.gov/nucleotide/NM_008386?report=genbank&log$=protalign&blast_rank=1&RID=GW3PRTTM016. Mus musculus insulin I (Ins1), mRNA.
Genbank [online], Accession No. AIW51918, Nov. 11, 2014, [retrieved on Jul. 15, 2020], Retrieved from the Internet: URL http://www.ncibi.nlm.nih.gov/protein/AIW51918.1. tat protein, partial [Human immunodeficiency virus 1].
Genbank [online], Accession No. NP_000453, Jul. 12, 2020, [retrieved on Jul. 15, 2020], Retrieved from the Internet: URL http://www.ncibi.nlm.nih.gov/protein/NP_000453.2?report=genbank&log$=protalign&blast_rank=1&RID=GZE7C970014&from=1&to=875. ubiquitin-protein ligase E3A isoform 2 [*Homo sapiens*].
Decision of Rejection issued by the Chinese National Intellectual Property Administration dated Nov. 29, 2021 for corresponding Chinese Patent Application No. 201680026461.3.
English Translation of the Decision of Rejection issued by the Chinese National Intellectual Property Administration dated Nov. 29, 2021 for corresponding Chinese Patent Application No. 201680026461.3.
Notification of the Second Office Action issued by the Chinese National Intellectual Property Administration dated Jun. 25, 2021 for corresponding Chinese Patent Application No. 201680026461.3.
English Translation of Notification of the Second Office Action issued by the Chinese National Intellectual Property Administration dated Jun. 25, 2021 for corresponding Chinese Patent Application No. 201680026461.3.
Official Action issued by the Canadian Patent Office dated Apr. 5, 2022 for corresponding Canadian Patent Application No. 2,984,629.

Richard, Jean Philippe et al. 2003. "Cell-Penetrating Peptides. A Reevaluation of the Mechanism of Cellular Uptake." The Journal of Biological Chemistry 278 (1): 585-90.
Simon, Melissa J. et al. 2009. "TAT-Mediated Intracellular Protein Delivery to Primary Brain Cells Is Dependent on Glycosaminoglycan Expression" Biotechnology and Bioengineering 104 (1): 10-19.
Chauhan, Ashok et al. 2007. "The Taming of the Cell Penetrating Domain of the HIV Tat: Myths and Realities." Journal of Controlled Release: Official Journal of the Controlled Release Society 117 (2): 148-62.
Flinterman, Marcella et al. 2009. "Delivery of Therapeutic Proteins as Secretable TAT Fusion Products." Molecular Therapy: The Journal of the American Society of Gene Therapy 17 (2): 334-42.
Erazo-Oliveras, Alfredo et al. 2012. "Improving the Endosomal Escape of Cell-Penetrating Peptides and Their Cargos: Strategies and Challenges." Pharmaceuticals 5 (11): 1177-1209.
El-Andaloussi, Samir et al. 2007. "Cargo-Dependent Cytotoxicity and Delivery Efficacy of Cell-Penetrating Peptides: A Comparative Study." Biochemical Journal 407 (2): 285-92.
Carty, N. et al. Convection-Enhanced Delivery and Systemic Mannitol Increase Gene Product Distribution of AAV Vectors 5, 8, and 9 and Increase Gene Product in the Adult Mouse Brain. J. Neurosci Methods. Dec. 15, 2010; 194(1): 144-153.
Nash, K. and M. Gordon. Convection Enhanced Delivery of Recombinant Adeno-associated Virus into the Mouse Brain. Gene Therapy for Neurological Disorders: Methods and Protocols, Methods in Molecular Biology, vol. 1382, Chapter 21: 285-295, 2016.
Colley, K. et al. Cellular Organization of Glycosylation. Essentials of Glycobiology. 3rd Edition. Cold Spring Harbor (NY): Cold Spring Harbor Laboratory Press; 2015-2017.
Dodge, A. et al. Generation of a Novel Rat Model of Angelman Syndrome with a Complete Ube3a Gene Deletion. Autism Res, 2020. 13(3): 397-409.
Hang, H.C. Molecular Probes for Protein Glycosylation, in Comprehensive Natural Products II,H.—W.B. Liu and L. Mander, Editors. 2010: Elsevier, p. 261-296.
Shinohara, Y. et al. Hippocampal CA3 and CA2 have distinct bilateral innervation patters to CA1 in rodents. European Journal of Neuroscience, 2012. 35(5): p. 702-710.
Silva-Santos, S. et al. Ube3a reinstatement identifies distinct developmental windows in a murine Angelman syndrome model. The Journal of Clinical Investigation, vol. 125, No. 5, May 2015;: 2069-2076.
Carty, N. et al. Intracranial Injection of AAV Expressing NEP but Not IDE Reduces Amyloid Pathology in APP+PS1 Transgenic Mice. PLoS One, vol. 8, Issue 3, e59626, Mar. 2013.
Tsagkaris, Christos et al. Gene Therapy for Angelman Syndrome: Contemporary Approaches and Future Endeavors. Current Gene Therapy, 2019, vol. 19, No. 6, 1-8.
Guerriero, Christopher and Jeffrey L. Brodsky. The Delicate Balance Between Secreted Protein Folding and Endoplasmic Reticulum-Associated Degradation in Human Physiology. Physiol Rev 92: 537-576, 2012.

* cited by examiner

MODIFIED UBE3A GENE FOR A GENE THERAPY APPROACH FOR ANGELMAN SYNDROME

CROSS-REFERENCE TO RELATED APPLICATIONS

This application is a continuation of and claims priority to International Patent Application No. PCT/US2016/031468, filed May 9, 2016 which claims priority to U.S. Provisional Application No. 62/158,269, entitled "Modified UBE3A Gene for a Gene Therapy Approach for Angelman Syndrome", filed May 7, 2015, which is incorporated herein by reference.

FIELD OF INVENTION

This invention relates to treatment of Angelman syndrome. More specifically, the present invention provides therapeutic methods and compositions for treating Angelman syndrome.

BACKGROUND OF INVENTION

Angelman syndrome (AS) is a genetic disorder affecting neurons, estimated to effect about one in every 15,000 births (Clayton-Smith, Clinical research on Angelman syndrome in the United Kingdom: observations on 82 affected individuals. Am J Med Genet. 1993 Apr. 1; 46(1):12-5), though the actual number of diagnosed AS cases is lower likely due to misdiagnosis.

Angelman syndrome is a continuum of impairment, which presents with delayed and reduced intellectual and developmental advancement, in particular with respect to language and motor skills. In particular, AS is defined by little or no verbal communication, with some non-verbal communication, ataxia, and disposition that includes frequent laughing and smiling and excitable movement.

More advanced cases result in severe mental retardation, seizures that may be difficult to control that typically begin before or by three years of age, frequent laughter (Nicholls, New insights reveal complex mechanisms involved in genomic imprinting. Am J Hum Genet. 1994 May; 54(5): 733-40), miroencephaly, and abnormal EEG. In severe cases, patients may not develop language or may only have use of 5-10 words. Movement is commonly jerky, and walking commonly is associated with hand flapping and a stiff-gait. The patients are commonly epileptic, especially earlier in life, and suffer from sleep apnea, commonly only sleeping for 5 hours at a time. They are social and desire human contact. In some cases, sin and eyes may have little or no pigment, possess sucking and swallowing problems, sensitivity to heat, and a fixation to water bodies. Studies in UBE3A-deficient mice show disturbances in long-term synaptic plasticity. There are currently no cures for Angelman syndrome, and treatment is palliative. For example, anticonvulsant medication is used to reduce epileptic seizures, and speech and physical therapy are used to improve language and motor skills.

The gene UBE3A is responsible for AS and it is unique in that it is one of a small family of human imprinted genes. UBE3A, found on chromosome 15, encodes for the homologous to E6AP C terminus (HECT) protein (E6-associated protein (E6AP) (Kishino, et al., UBE3A/E6-AP mutations cause Angelman syndrome. Nat Gen. 1997 Jan. 15. 15(1): 70-3). UBE3A undergoes spatially-defined maternal imprinting in the brain; thus, the paternal copy is silenced via DNA methylation (Albrecht, et al., Imprinted expression of the murine Angelman syndrome gene, Ube3a, in hippocampal and Purkinje neurons. Nat Genet. 1997 September; 17(1):75-8). As such, only the maternal copy is active, the paternal chromosome having little or no effect on the proteosome of the neurons in that region of the brain. Inactivation, translocation, or deletion of portions of chromosome 15 therefore results in uncompensated loss of function. Some studies suggest improper E3-AP protein levels alter neurite contact in Angelman syndrome patients (Tonazzini, et al., Impaired neurite contract guidance in ubuitin ligase E3a (Ube3a)-deficient hippocampal neurons on nanostructured substrates. Adv Healthc Mater. 2016 April; 5(7):850-62).

The majority of Angelman's syndrome cases (70%) occur through a de novo deletion of around 4 Mb from 15q11-q13 of the maternal chromosome which incorporates the UBE3A gene (Kaplan, et al., Clinical heterogeneity associated with deletions in the long arm of chromosome 15: report of 3 new cases and their possible significance. Am J Med Genet. 1987 September; 28(1):45-53), but it can also occur as a result of abnormal methylation of the maternal copy, preventing its expression (Buiting, et al., Inherited microdeletions in the Angelman and Prader-Willi syndromes define an imprinting centre on human chromosome 15. Nat Genet. 1995 April; 9(4):395-400; Gabriel, et al., A transgene insertion creating a heritable chromosome deletion mouse model of Prader-Willi and Angelman syndrome. Proc Natl Acad Sci U.S.A. 1999 August; 96(16):9258-63) or uniparental disomy in which two copies of the paternal gene are inherited (Knoll, et al., Angelman and Prader-Willi syndromes share a common chromosome 15 deletion but differ in parental origin of the deletion. Am J Med Genet. 1989 Fed; 32(2):285-90; Malcolm, et al., Uniparental paternal disomy in Angelman's syndrome. Lancet. 1991 Mar. 23; 337(8743):694-7). The remaining AS cases arise through various UBE3A mutations of the maternal chromosome or they are diagnosed without a genetic cause (12-15UBE3A codes for the E6-associated protein (E6-AP) ubiquitin ligase. E6-AP is an E3 ubiquitin ligase, therefore it exhibits specificity for its protein targets, which include the tumor suppressor molecule p53 (Huibregtse, et al., A cellular protein mediates association of p53 with the E6 oncoprotein of human papillomavirus types 16 or 18. EMBO J. 1991 December; 10(13):4129-35), a human homologue to the yeast DNA repair protein Rad23 (Kumar, et al., Identification of HHR23A as a substrate for E6-associated protein-mediated ubiquitination. J Biol Chem. 1999 Jun. 25; 274(26):18785-92), E6-AP itself, and Arc, the most recently identified target (Nuber, et al., The ubiquitin-protein ligase E6-associated protein (E6-AP) serves as its own substrate. Eur J Biochem. 1998 Jun. 15; 254(3):643-9; Greer, et al., The Angelman Syndrome protein Ube3A regulates synapse Development by ubiquitinating arc. Cell. 2010 Mar. 5; 140(5): 704-16).

Mild cases are likely due to a mutation in the UBE3A gene at chromosome 15q11-13, which encodes for E6-AP ubiquitin ligase protein of the ubiquitin pathway, and more severe cases resulting from larger deletions of chromosome 15. Commonly, the loss of the UBE3A gene in the hippocampus and cerebellum result in Angelman syndrome, though single loss-of-function mutations can also result in the disorder.

The anatomy of the mouse and human AS brain shows no major alterations compared to the normal brain, indicating the cognitive deficits may be biochemical in nature as opposed to developmental (Jiang, et al., Mutation of the Angelman ubiquitin ligase in mice causes increased cytoplasmic p53 and deficits of contextual learning and long-term potentiation. Neuron. 1998 October; 21(4):799-811; Davies, et al., Imprinted gene expression in the brain. Neurosci Biobehav Rev. 2005 May; 29(3):421-430). An Angelman syndrome mouse model possessing a disruption of the maternal UBE3A gene through a null mutation of exon 2 (Jiang, et al., Mutation of the Angelman ubiquitin ligase in mice causes increased cytoplasmic p53 and deficits of contextual learning and long-term potentiation. Neuron. 1998 October; 21(4):799-811) was used. This model has been incredibly beneficial to the field of AS research due to its ability in recapitulating the major phenotypes characteristic of AS patients. For example, the AS mouse has inducible seizures, poor motor coordination, hippocampal-dependent learning deficits, and defects in hippocampal LTP. Cognitive deficits in the AS mouse model were previously shown to be associated with abnormalities in the phosphorylation state of calcium/calmodulin-dependent protein kinase II (CaMKII) (Weeber, et al., Derangements of hippocampal calcium/calmodulin-dependent protein kinase II in a mouse model for Angelman mental retardation syndrome. J Neurosci. 2003 April; 23(7):2634-44). There was a significant increase in phosphorylation at both the activating $Thr^{286}$ site as well as the inhibitory $Thr^{305}$ site of αCaMKII without any changes in total enzyme level, resulting in an overall decrease in its activity. There was also a reduction in the total amount of CaMKII at the postsynaptic density, indicating a reduction in the amount of active CaMKII. Crossing a mutant mouse model having a point mutation at the $Thr^{305}$ site preventing phosphorylation with the AS mouse rescued the AS phenotype. i.e. seizure activity, motor coordination, hippocampal-dependent learning, and LTP were restored similar to wildtype levels. Thus, postnatal expression of αCaMKII suggests that the major phenotypes of the AS mouse model are due to postnatal biochemical alterations as opposed to a global developmental defect (Bayer, et al., Developmental expression of the CaM kinase II isoforms: ubiquitous γ- and δ-CaM kinase II are the early isoforms and most abundant in the developing nervous system. Brain Res Mol Brain Res. 1999 Jun. 18; 70(1):147-54).

Deficiencies in Ube3a are also linked in Huntington's disease (Maheshwari, et al., Deficeincy of Ube3a in Huntington's disease mice brain increases aggregate load and accelerates disease pathology. Hum Mol Genet. 2014 Dec. 1; 23(23):6235-45).

Matentzoglu noted E6-AP possesses non-E3 activity related to hormone signaling (Matentzoglu, EP 2,724,721 A1). As such, administration of steroids, such as androgens, estrogens, and glucocorticoids, was used for treating various E6-AP disorders, including Angelman syndrome, autism, epilepsy, Prader-Willi syndrome, cervical cancer, fragile X syndrome, and Ret syndrome. Philpot suggested using a topoisomerase inhibitor to demethylate silenced genes thereby correcting for deficiencies in Ube3A (Philpot, et al., P.G. Pub. US 2013/0317018 A1). However, work in the field, and proposed therapeutics, do not address the underlying disorder, as in the use of steroids, or may result in other disorders, such as autism, where demethylation compounds are used. Accordingly, what is needed is a therapeutic that addresses the underlying cause of UBE3A deficiency disorders, in a safe, efficacious manner.

SUMMARY OF THE INVENTION

While most human disorders characterized by severe mental retardation involve abnormalities in brain structure, no gross anatomical changes are associated with AS. A, Ube3a protein has been generated containing an appended to a cellular secretion sequence that allows the secretion of Ube3a from cells and cellular uptake sequence that provides uptake by neighboring neuronal cells. This provides a functional E6-AP protein into the neurons thereby rescuing from disease pathology.

As such, a UBE3A vector was formed using a transcription initiation sequence, and a UBE construct disposed downstream of the transcription initiation sequence. The UBE construct is formed of a UBE3A sequence, a secretion sequence, and a cell uptake sequence. Nonlimiting examples of the UBE3A sequence are SEQ ID No. 1, SEQ ID No. 6, SEQ ID No. 12, SEQ ID No. 13, a cDNA of SEQ ID No. 7, or a homologous sequence. Variations of the DNA sequence include conservative mutations in the DNA triplet code, as seen in the Table. In specific variations, the UBE3A sequence is *Mus musculus* UBE3A U82122.1, *Homo sapiens* UBE3A variant 1, and variant 2. Nonlimiting examples of the secretion sequence are SEQ ID No. 2, SEQ ID No. 8, SEQ ID No. 9, SEQ ID No. 10, a cDNA of SEQ ID No. 3, or a homologous sequence, with variations of the DNA sequence that include the aforementioned conservative mutations. Nonlimiting examples of the cell uptake sequence are SEQ ID No. 4, SEQ ID No. 11, a cDNA of SEQ ID No. 5, or a homologous sequence. Variations of the DNA sequence include the aforementioned conservative mutations. In specific variations of the invention, the secretion sequence is disposed upstream of the UBE3A sequence, and more specifically is optionally is disposed upstream of the UBE3A sequence and downstream of the secretion sequence.

The Table shows the redundant triplet code and corresponding encoded amino acids, based on functional group category.

| Nonpolar, aliphatic | Gly | G | GGT | Polar, uncharged | Ser | S | AGT |
| --- | --- | --- | --- | --- | --- | --- | --- |
| | | | GGC | | | | AGC |
| | | | GGA | | | | TCT |
| | | | GGG | | | | TCC |
| | | | | | | | TCA |
| | | | | | | | TCG |
| | Ala | A | GCT | | Thr | T | ACT |
| | | | GCC | | | | ACC |
| | | | GCA | | | | ACA |
| | | | GCG | | | | ACG |
| | Val | V | GTT | | Cys | C | TGT |
| | | | GTC | | | | TGC |
| | | | GTA | | | | |
| | | | GTG | | | | |
| | Leu | L | TTA | | Pro | P | CCT |
| | | | TTG | | | | CCC |
| | | | CTT | | | | CCA |
| | | | CTC | | | | CCG |
| | | | CTA | | | | |
| | | | CTG | | | | |
| | Met | M | ATG | | Asn | N | AAT |
| | | | | | | | AAC |
| | Ile | I | ATT | | Gln | Q | CAA |
| | | | ATC | | | | CAG |
| | | | ATA | | | | |
| Aromatic | Phe | F | TTT | Positive charge | Lys | K | AAA |
| | | | TTC | | | | AAG |
| | Tyr | Y | TAT | | His | H | CAT |
| | | | TAC | | | | CAC |
| | Trp | W | TGG | | Arg | R | CGT |
| | | | | | | | CGC |
| | | | | | | | CGA |
| | | | | | | | CGG |
| | | | | | | | AGA |
| | | | | | | | AGG |

-continued

| Negative charge | Asp | D | GAT GAC | OTHER | stop | TTA TAG TGA |
|---|---|---|---|---|---|---|
|  | Glu | E | GAA GAG |  |  |  |

In some variations of the invention, the transcription initiation sequence is a cytomegalovirus chicken-beta actin hybrid promoter, or human ubiquitin c promoter. The invention optionally includes an enhancer sequence. A nonlimiting example of the enhancer sequence is a cytomegalovirus immediate-early enhancer sequence disposed upstream of the transcription initiation sequence. The vector optionally also includes a woodchuck hepatitis post-transcriptional regulatory element.

In variations, the vector is inserted into a plasmid, such as a recombinant adeno-associated virus serotype 2-based plasmid. In specific variations, the recombinant adeno-associated virus serotype 2-based plasmid lacks DNA integration elements. A nonlimiting example of the recombinant adeno-associated virus serotype 2-based plasmid is a pTR plasmid.

A method of synthesizing a UBE3A vector is also provided. A UBE3A construct was inserted into a backbone plasmid having a transcription initiation sequence, where the UBE3A construct is formed of a UBE3A sequence, a secretion sequence, and a cell uptake sequence. In some variations, the UBE3A construct was inserted downstream of the transcription initiation sequence. Nonlimiting examples of the UBE3A sequence are SEQ ID No. 1, SEQ ID No. 6, SEQ ID No. 12, SEQ ID No. 13, a cDNA of SEQ ID No. 7, or a homologous sequence. Variations of the DNA sequence include conservative mutations in the DNA triplet code, as seen in the Table. Nonlimiting examples of the secretion sequence are SEQ ID No. 2, SEQ ID No. 8, SEQ ID No. 9, SEQ ID No. 10, a cDNA of SEQ ID No. 3, or a homologous sequence, with variations of the DNA sequence that include the aforementioned conservative mutations. Nonlimiting examples of the cell uptake sequence are SEQ ID No. 4, SEQ ID No. 11, a cDNA of SEQ ID No. 5, or a homologous sequence. Variations of the DNA sequence include the aforementioned conservative mutations. In specific variations of the invention, the secretion sequence is disposed upstream of the UBE3A sequence, and more specifically is optionally is disposed upstream of the UBE3A sequence and downstream of the secretion sequence. For example, Ube3a gene was cloned and fused in frame to the 3' DNA sequence (N-terminus with two other peptide sequences), signal peptide and HIV TAT sequences, which were cloned into a recombinant adeno-associated viral vector for expression of the secreted E6-AP protein in the brain and spinal cord of AS patients. The UBE construct is optionally inserted by cleaving the backbone plasmid with at least one endonuclease, and the UBE3A construct ligated to the cleaved ends of the backbone plasmid.

The vector was then optionally inserted into an amplifaction host, possessing an antibiotic resistance gene, and subjected to an antibiotic selection corresponding to the antibiotic resistance gene. The amplifaction host was then expanded in a medium containing the antibiotic selection and the expanded amplifaction host collected. The vector was then isolated from the amplifaction host. In specific variations of the invention, the antibiotic resistance gene is an ampicillin resistance gene, with the corresponding antibiotic selection, ampicillin.

A method of treating a UBE3A deficiency disease, such as Angelman syndrome, Prader-Willi syndrome, or Huntington's disease, is also provided. A vector, as described above, was administered to the brain of a patient suffering from the UBE3A deficiency disease to correct the UBE deficiency. The vector was optionally administered by injection. Nonlimiting examples include intrahippocampal or ventricular injection. In specific variations, the vector was injected bilaterally. Optional dosages include about $5.55 \times 10^{11}$ genomes/g brain mass to about $2.86 \times 10^{12}$ genomes/g brain mass, or more specifically $5.55 \times 10^{11}$ to $2.86 \times 10^{12}$ genomes/g brain mass. Nonlimiting examples of dosages are:

$5.55 \times 10^{11}$ genomes/g brain mass, $5.75 \times 10^{11}$ genomes/g brain mass, $5.8 \times 10^{11}$ genomes/g brain mass, $5.9 \times 10^{11}$ genomes/g brain mass, $6.0 \times 10^{11}$ genomes/g brain mass, $6.1 \times 10^{11}$ genomes/g brain mass, $6.2 \times 10^{11}$ genomes/g brain mass, $6.3 \times 10^{11}$ genomes/g brain mass, $6.4 \times 10^{11}$ genomes/g brain mass, $6.5 \times 10^{11}$ genomes/g brain mass, $6.6. \times 10^{11}$ genomes/g brain mass, $6.7 \times 10^{11}$ genomes/g brain mass, $6.8 \times 10^{11}$ genomes/g brain mass, $6.9. \times 10^{11}$ genomes/g brain mass, $7.0 \times 10^{11}$ genomes/g brain mass, $7.1 \times 10^{11}$ genomes/g brain mass, $7.2 \times 10^{11}$ genomes/g brain mass, $7.3 \times 10^{11}$ genomes/g brain mass, $7.4 \times 10^{11}$ genomes/g brain mass, $7.5 \times 10^{11}$ genomes/g brain mass, $7.6 \times 10^{11}$ genomes/g brain mass, $7.7 \times 10^{11}$ genomes/g brain mass, $7.8 \times 10^{11}$ genomes/g brain mass, $7.9 \times 10^{11}$ genomes/g brain mass, $8.0 \times 10^{11}$ genomes/g brain mass, $8.1 \times 10^{11}$ genomes/g brain mass, $8.2 \times 10^{11}$ genomes/g brain mass, $8.3 \times 10^{11}$ genomes/g brain mass, $8.4 \times 10^{11}$ genomes/g brain mass, $8.5 \times 10^{11}$ genomes/g brain mass, $8.6 \times 10^{11}$ genomes/g brain mass, $8.7 \times 10^{11}$ genomes/g brain mass, $8.8 \times 10^{11}$ genomes/g brain mass, $8.9 \times 10^{11}$ genomes/g brain mass, $9.0 \times 10^{11}$ genomes/g brain mass, $9.1 \times 10^{11}$ genomes/g brain mass, $9.2 \times 10^{11}$ genomes/g brain mass, $9.3 \times 10^{11}$ genomes/g brain mass, $9.4 \times 10^{11}$ genomes/g brain mass, $9.5 \times 10^{11}$ genomes/g brain mass, $9.6 \times 10^{11}$ genomes/g brain mass, $9.7 \times 10^{11}$ genomes/g brain mass, $9.80 \times 10^{11}$ genomes/g brain mass, $1.0 \times 10^{12}$ genomes/g brain mass, $1.1 \times 10^{12}$ genomes/g brain mass, $1.2 \times 10^{12}$ genomes/g brain mass, $1.3 \times 10^{12}$ genomes/g brain mass, $1.4 \times 10^{12}$ genomes/g brain mass, $1.5 \times 10^{12}$ genomes/g brain mass, $1.6 \times 10^{12}$ genomes/g brain mass, $1.7 \times 10^{12}$ genomes/g brain mass, $1.8 \times 10^{12}$ genomes/g brain mass, $1.9 \times 10^{12}$ genomes/g brain mass, $2.0 \times 10^{12}$ genomes/g brain mass, $2.1 \times 10^{12}$ genomes/g brain mass, $2.2 \times 10^{12}$ genomes/g brain mass, $2.3 \times 10^{12}$ genomes/g brain mass, $2.40 \times 10^{12}$ genomes/g brain mass, $2.5 \times 10^{12}$ genomes/g brain mass, $2.6 \times 10^{12}$ genomes/g brain mass, $2.7 \times 10^{12}$ genomes/g brain mass, $2.75 \times 10^{12}$ genomes/g brain mass, $2.8 \times 10^{12}$ genomes/g brain mass, or $2.86 \times 10^{12}$ genomes/g brain mass.

BRIEF DESCRIPTION OF THE DRAWINGS

For a fuller understanding of the invention, reference should be made to the following detailed description, taken in connection with the accompanying drawings, in which.

For a fuller understanding of the invention, reference should be made to the following detailed description, taken in connection with the accompanying drawings, in which.

DETAILED DESCRIPTION OF THE PREFERRED EMBODIMENT

Figure 1:
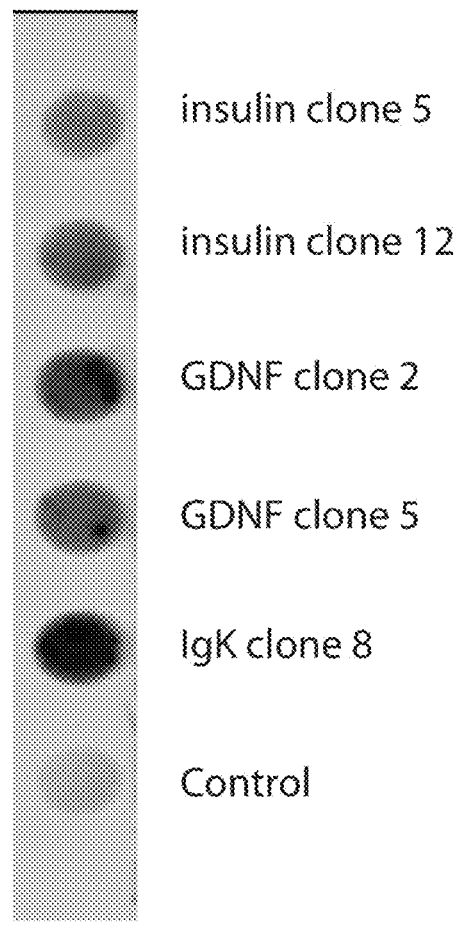
FIG. 1 is a dot blot of anti-GFP on media from HEK293 cells transfected with GFP clones containing signal peptides as indicated.

As used herein, the singular forms "a," "an" and "the" include plural referents unless the context clearly dictates otherwise. Thus, for example, reference to "a polypeptide" includes a mixture of two or more polypeptides and the like.

As used herein, "about" means approximately or nearly and in the context of a numerical value or range set forth means±15% of the numerical "Administration" or "administering" is used to describe the process in which compounds of the present invention, alone or in combination with other compounds, are delivered to a patient. The composition may be administered in various ways including oral, parenteral (referring to intravenous and intraarterial and other appropriate parenteral routes), intratheceally, intramuscularly, subcutaneously, colonically, rectally, and nasally, among others. Each of these conditions may be readily treated using other administration routes of compounds of the present invention to treat a disease or condition. The dosing of compounds and compositions of the present invention to obtain a therapeutic or prophylactic effect is determined by the circumstances of the patient, as known in the art. The dosing of a patient herein may be accomplished through individual or unit doses of the compounds or compositions herein or by a combined or prepackaged or pre-formulated dose of a compounds or compositions. An average 40 g mouse has a brain weighing 0.416 g, and a 160 g mouse has a brain weighing 1.02 g, a 250 g mouse has a brain weighing 1.802 g. An average human brain weighs 1508 g, which can be used to direct the amount of thereapeutic needed or useful to accomplish the treatment described herein.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations which can be used in connection with the subject invention.

As used herein "animal" means a multicellular, eukaryotic organism classified in the kingdom Animalia or Metazoa. The term includes, but is not limited to, mammals. Non-limiting examples include rodents, mammals, aquatic mammals, domestic animals such as dogs and cats, farm animals such as sheep, pigs, cows and horses, and humans. Wherein the terms "animal" or the plural "animals" are used, it is contemplated that it also applies to any animals.

As used herein, the term "homologous" means a nucleotide sequence possessing at least 80% sequence identity, preferably at least 90% sequence identity, more preferably at least 95% sequence identity, and even more preferably at least 98% sequence identity to the target sequence. Variations in the nucleotide sequence can be conservative mutations in the nucleotide sequence, i.e. mutations in the triplet code that encode for the same amino acid as seen in the Table.

As used herein, the term "therapeutically effective amount" refers to that amount of a therapy (e.g., a therapeutic agent or vector) sufficient to result in the amelioration of Angelman syndrome or other UBE3A-related disorder or one or more symptoms thereof, prevent advancement of Angelman syndrome or other UBE3A-related disorder, or cause regression of Angelman syndrome or other UBE3A-related disorder.

As used herein "patient" is used to describe an animal, preferably a human, to whom treatment is administered, including prophylactic treatment with the compositions of the present invention.

Example 1

To test the efficacy of the secretion signal, GFP was cloned in frame with human insulin, GDNF or IgK signal peptides. The construct was inserted into a pTR plasmid and transfected into HEK293 cells (American Type Culture Collection, Manassas, Va.). HEK293 cells were grown at 37° C. 5% $CO_2$ in Dulbecco's Modified Essential Medium (DMEM) with 10% FBS and 1% Pen/Strep and subcultured at 80% confluence.

The vector (2 µg/well in a 6-well plate) was transfected into the cells using PEI transfection method. The cells were subcultured at 0.5×10$^6$ cells per well in a 6-well plate with DMEM medium two days before the transfection. Medium was replaced the night before transfection. Endotoxin-free $dH_2O$ was heated to at around 80° C., and polyethylenimine (Sigma-Aldrich Co. LLC, St. Louis, Mo.) dissolved. The solution was allowed to cool to around 25° C., and the solution neutralized using sodium hydroxide. AAV4-STUb vector or negative control (medium only) was added to serum-free DMEM at 2 µg to every 200 µL for each well transfected, and 9 µL of 1 µg/µL polyethylenimine added to the mix for each well. The transfection mix was incubated at room temperature for 15 minutes, then then added to each well of cells at 210 µL per well and incubated for 48 hours.

Media was collected from each culture well and 2 µL spotted onto a nitrocellulose membrane using a narrow-tipped pipette. After the samples dried, the membrane was blocked applying 5% BSA in TBS-T to the membrane and incubating at room temperature for 30 minutes to 1 hour, followed by incubating the membrane with chicken anti-GFP (5 µg/mL, Abcam PLC, Cambridge, UK; #ab13970) in BSA/TBS-T for 30 min at room temperature. The membrane was washed with TBS-T 3 times, 5 minutes for each wash. The membrane was incubated with anti-chicken HRP conjugate secondary antibody (Southern Biotechnology, Thermo Fisher Scientific. Inc., Waltham, Mass.; #6100-05, 1/3000) conjugated with HRP for 30 minutes at room temperature, followed by washing the membrane three times with TBS-T, once for 15 minutes, and subsequent washed at 5 minutes each. The membrane was washed with TBS for 5 minutes at room temperatire, and incubated with luminescence reagent for 1 minute (Millipore, Merck KGaA, Darmstadt, Del.; #WBKLS0100). The membrane was recorded on a GE Amersham Imager 600 (General Electric, Fairfield, Calif.), shown in FIG. 1.

As seen from FIG. 1, all three secretion signals resulted in release of GFP-tagged protein from cells as observed by comparison to untransfected control cells. Of the three secretion constructs, the IgK construct showed the highest level of secretion, though clone 2 of the GDNF construct did display similarly high secretion of GFP-tagged protein.

Example 2

A mouse-UBE3A vector construct was generated using a pTR plasmid. The mouse (*Mus musculus*) UBE3A gene was formed from cDNA (U82122.1);

(SEQ ID No. 1)
```
atgaagcgag cagctgcaaa gcatctaata gaacgctact
accatcagtt aactgaggc tgtggaaatg aggcctgcac
gaatgagttt tgtgcttcct gtccaacttt tcttcgtatg
gataacaatg cagcagctat aaagcccctt gagctttata
aaattaatgc aaaactctgt gatcctcatc cctccaagaa
aggagcaagc tcagcttacc ttgagaactc aaaaggtgca
tctaacaact cagagataaa aatgaacaag aaggaaggaa
aagattttaa agatgtgatt tacctaactg aagagaaagt
atatgaaatt tatgaatttt gtagagagag tgaggattat
tccccttttaa ttcgtgtaat tggaagaata ttttctagtg
ctgaggcact ggttctgagc tttcggaaag tcaaacagca
cacaaaggag gaattgaaat ctcttcaaga aaaggatgaa
gacaaggatg aagatgaaaa ggaaaaagct gcatgttctg
ctgctgctat ggaagaagac tcagaagcat cttcttcaag
gatgggtgat agttcacagg gagacaacaa tgtacaaaaa
ttaggtcctg atgatgtgac tgtggatatt gatgctatta
gaagggtcta cagcagtttg ctcgctaatg aaaaattaga
aactgccttc ctgaatgcac ttgtatatct gtcacctaac
gtggaatgtg atttgacata tcataatgtg tatactcgag
atcctaatta tctcaatttg ttcattattg taatggagaa
tagtaatctc cacagtcctg aatatctgga aatggcgttg
ccattatttt gcaaagctat gtgtaagcta cccccttgaag
ctcaaggaaa actgattagg ctgtggtcta aatacagtgc
tgaccagatt cggagaatga tggaaacatt tcagcaactt
attcctaca aagtcataag caatgaattt aatagccgaa
atctagtgaa tgatgatgat gccattgttg ctgcttcaaa
gtgtttgaaa atggtttact atgcaaatgt agtgggaggg
gatgtggaca caaatcataa tgaggaagat gatgaagaac
ccatacctga gtccagcgaa ttaacacttc aggagcttct
gggagatgaa agaagaaata agaaaggtcc tcgagtggat
ccactagaaa ccgaacttgg cgttaaaact ctagactgtc
gaaaaccact tatctccttt gaagaattca ttaatgaacc
actgaatgat gttctagaaa tggacaaaga ttataccttt
ttcaaagttg aaacagagaa caaattctct tttatgacat
gtccctttat attgaatgct gtcacaaaga atctgggatt
atattatgac aatagaattc gcatgtacag tgaaagaaga
atcactgttc tttacagcct agttcaagga cagcagttga
atccgtatt gagactcaaa gtcagacgtg accatattat
agatgatgca ctggtccggc tagagatgat tgctatgaa
aatcctgcag acttgaagaa gcagttgtat gtggaatttg
```
aaggagaaca aggagtaatg agggaggcgt ttccaaagag
ttttttcagt tgggttgtgg aggaaatttt taatccaaat
attggtatgt tcacatatga tgaagctacg aaattatttt
ggtttaatcc atcttctttt gaaactgagg gtcaggttta
ctctgattgg catatcctgg gtctggctat ttacaataat
tgtatactgg atgtccattt tcccatggtt gtatacagga
agctaatggg gaaaaaagga acctttcgtg acttgggaga
ctctcaccca gttttatatc agagtttaaa ggatttattg
gaatatgaag gagtgtgga agatgatatg atgatcactt
tccagatatc acagacagat cttttggta acccaatgat
gtatgatcta aaagaaaatg gtgataaaat tccaattaca
aatgaaaaca ggaaggaatt tgtcaatctc tattcagact
acattctcaa taaatctgta gaaaaacaat tcaaggcatt
tcgcagaggt tttcatatgg tgactaatga atcgcccta
aaatacttat tcagaccaga agaaattgaa ttgcttatat
gtggaagccg gaatctagat ttccaggcac tagaagaaac
tacagagtat gacggtggct atacgaggga atctgttgtg
attagggagt tctgggaaat tgttcattcg tttacagatg
aacagaaaag actctttctg cagtttacaa caggcacaga
cagagcacct gttggaggac taggaaaatt gaagatgatt
atagccaaaa atggcccaga cacagaaagg ttacctacat
ctcatacttg ctttaatgtc ctttttacttc cggaatattc
aagcaaagaa aaacttaaag agagattgtt gaaggccatc
acatatgcca aaggatttgg catgctgtaa.
```

The cDNA was subcloned and sequenced. The mouse UBE3A gene (SEQ ID No. 1) was fused to DNA sequences encoding a section signaling peptide (SEQ ID No. 2) and HIV TAT sequence (SEQ ID No. 4). The section signaling peptide has the DNA sequence;

(SEQ ID No. 2)
```
atg gcc ctg ttg gtg cac ttc cta ccc ctg ctg gcc
ctg ctt gcc ctc tgg gag ccc aaa ccc acc cag gct
ttt gtc,
``` encoding to protein sequence;

(SEQ ID No. 3)
MALLVHFLPLLALLALWEPKPTQAFV;

while HIV TAT sequence is;

(SEQ ID No. 4)
```
tac ggc aga aag aag agg agg cag aga agg aga,
``` encoding to protein sequence;

(SEQ ID No. 5)
YGRKKRRQRRR.

Figure 2:
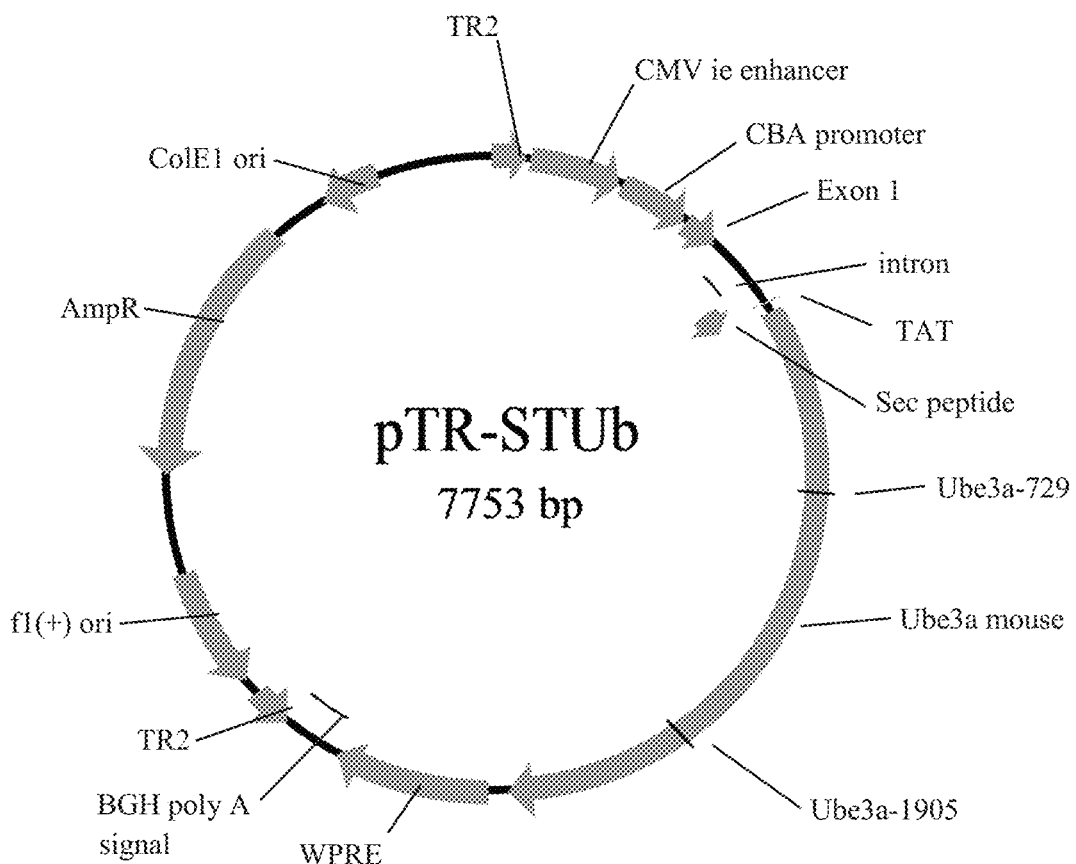
FIG. 2 is a map of the mouse UBE3A vector construct used in the present invention. Major genes are noted.

The construct sequence of SEQ ID No. 1 fused with SEQ ID No. 2 and SEQ ID No. 4 was inserted into a pTR plasmid. The plasmid was cleaved using Age I and Xho I endonucleases and the construct sequence ligated using ligase. The vector contains AAV serotype 2 terminal repeats, CMV-chicken-beta actin hybrid promoter and a WPRE, seen in FIG. 2. The recombinant plasmid lacks the Rep and Cap elements, limiting integration of the plasmid into host DNA.

The vector (AAV4-STUb vector) was then transformed into *Escherichia coli* (*E. coli*, Invitrogen, Thermo Fisher Scientific, Inc., Waltham, Mass.; SURE2 cells). Briefly, cells were equilibrated on ice and 1 pg to 500 ng of the vector were added to the *E. coli* and allowed to incubate for about 1 minute. The cells were electroporated with a BioRad Gene Pulser in a 0.1 cm cuvette (1.7V, 200 Ohms). The *E. Coli* were then grown in media for 60 min preior to being plated onto agar, such as ATCC medium 1065 (American Type Culture Collection, Manassas, Va.), with ampicillin (50 μg/mL).

*E. coli* was expanded in broth containing ampicillin to collect large amounts of vector.

Example 3

The mouse vector properties of the construct generated in Example 2 were tested in HEK293 cells (American Type Culture Collection, Manassas, Va.). HEK293 cells were grown at 37° C. 5% $CO_2$ in Dulbecco's Modified Essential Medium (DMEM) with 10% FBS and 1% Pen/Strep and subcultured at 80% confluence.

The vector (2 μg/well in a 6-well plate) was transfected into the cells using PEI transfection method. The cells were subcultured at $0.5 \times 10^6$ cells per well in a 6-well plate with DMEM medium two days before the transfection. Medium was replaced the night before transfection. Endotoxin-free $dH_2O$ was heated to at around 80° C., and polyethylenimine (Sigma-Aldrich Co. LLC, St. Louis, Mo.) dissolved. The solution was allowed to cool to around 25° C., and the solution neutralized using sodium hydroxide. AAV4-STUb vector or negative control (medium only) was added to serum-free DMEM at 2 μg to every 200 μl for each well transfected, and 9 μl of 1 μg/μ; polyethylenimine added to the mix for each well. The transfection mix was incubated at room temperature for 15 minutes, then then added to each well of cells at 210 μl per well and incubated for 48 hours.

Figure 3:
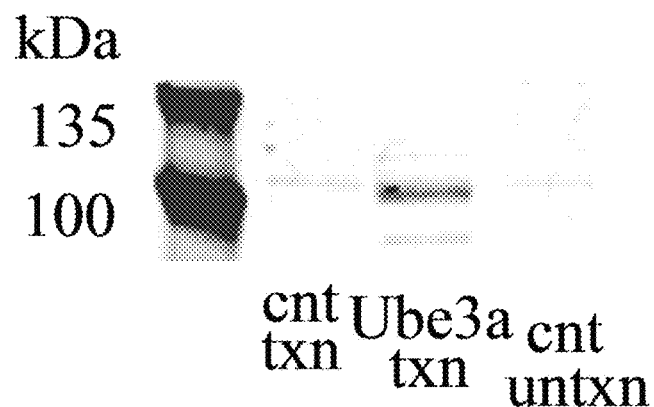
FIG. 3 is a Western blot showing secretion of E6-AP protein from plasmid transfected HEK293 cells. Culture media taken from control cells transfected cell culture media (cnt txn), media from Ube3a transfected cells (Ube3a txn); and media from untransfected cells (cnt untxn) were run on an acrylamide gel and anti-E6-AP antibody.

Media was collected from AAV4-STUb vector transfected cells, medium-only transfected control cells, and untransfected control cells. The medium was run on Western blot and stained with rabbit anti-E6-AP antibody (A300-351A, Bethyl Labs, Montgomery, Tex.), which is reactive against human and mouse E6-AP, at 0.4 μg/ml. Secondary conjugation was performed with rabbit-conjugated horseradish peroxidase (Southern Biotechnology, Thermo Fisher Scientific, Inc., Waltham, Mass.). The results were determined densiometrically, and show the HEK293 cells transfected with AAV4-STUb secrete E6-AP protein into the medium, as seen in FIG. 3.

Example 4

Transgenic mice were formed by crossbreeding mice having a deletion in the maternal UBE3A (Jiang, et al., Mutation of the Angelman ubiquitin ligase in mice causes increased cytoplasmic p53 and deficits of contextual learning and long-term potentiation. Neuron. 1998 October; 21(4):799-811; Gustin, et al., Tissue-specific variation of Ube3a protein expression in rodents and in a mouse model of Angelman syndrome. Neurobiol Dis. 2010 September; 39(3):283-91); Heck, et al., Analysis of cerebellar function in Ube3a-deficient mice reveals novel genotype-specific behaviors. Hum Mol Genet. 2008 Jul. 15; 17(14):2181-9) and GABARB3 ( ). Mice were housed in a 12 hour day-light cycle and fed food and water ad libitum. Three month old mice were treated with the vector.

Mice were anesthetized with isoflurane and placed in the stereotaxic apparatus (51725D Digital Just for Mice Stereotaxic Instrument, Stoelting, Wood Dale, Ill.). An incision was made sagitally over the middle of the cranium and the surrounding skin pushed back to enlarge the opening. The following coordinates were used to locate the left and right hippocampus: AP 22.7 mm, L 62.7 mm, and V 23.0 mm. Mice received bilateral intrahippocampal injections of either AAV4-STUb particles at a concentration of $1 \times 10^{12}$ genomes/mL (N=2) in 10 μL of 20% mannitol or vehicle (10 μL of 20% mannitol) using a 10 mL Hamilton syringe in each hemisphere. The wound was cleaned with saline and closed using Vetbond (NC9286393 Fisher Scientific, Pittsburgh, Pa.). Control animals included uninjected AS mice and littermate wild type mice (n=2). Mice recovered in a clean, empty cage on a warm heating pad and were then singly housed until sacrificed. The mice were monitored over the course of the experiment.

At day 30 after treatment, the mice were euthanized by injecting a commercial euthanasia solution, Somnasol®, (0.22 ml/kg) intraperitoneally. After euthanizing the animals, CSF was collected and the animals were perfused with PBS and the brain removed. The brain was fixed in 4% paraformaldehyde solution overnight prior to cryoprotection in sucrose solutions. Brains were sectioned at 25 μm using a microtome.

Most recombinant adeno-associated virus vector studies inject the vector directly into the parenchymal, which typically results in limited cellular transduction (Li, et al., Intra-ventricular infusion of rAAV-1-EGFP resulted in transduction in multiple regions of adult rat brain: a comparative study with rAAV2 and rAAV5 vectors. Brain Res. 2006 Nov. 29; 1122(1):1-9). However, appending a secretion signaling sequence and TAT sequence to the Ube3A protein allows for secretion of the HECT protein (i.e., UBE3A) from transfected cells and uptake of the peptide by adjacent neurons, allowing injection into a discrete site to service as a supply of protein for other sites throughout the brain.

Brains from sacrificed mice were sliced using a microtome and stained for E6-AP protein using anti-E6-AP antibody (A300-351A, Bethyl Labs, Montgomery, Tex.) with a biotinylated anti-rabbit secondary antibody (Vector Labs #AB-1000). Staining was completed with ABC (Vector Labs) and DAB reaction. Sections were mounted and scanned using Zeiss Axio Scan microscope. Percentage area staining was quantified using IAE-NearCYTE image analysis software (University of Pittsburgh Starzl Transplant Institute, Pittsburgh, Pa.).

Figure 4:
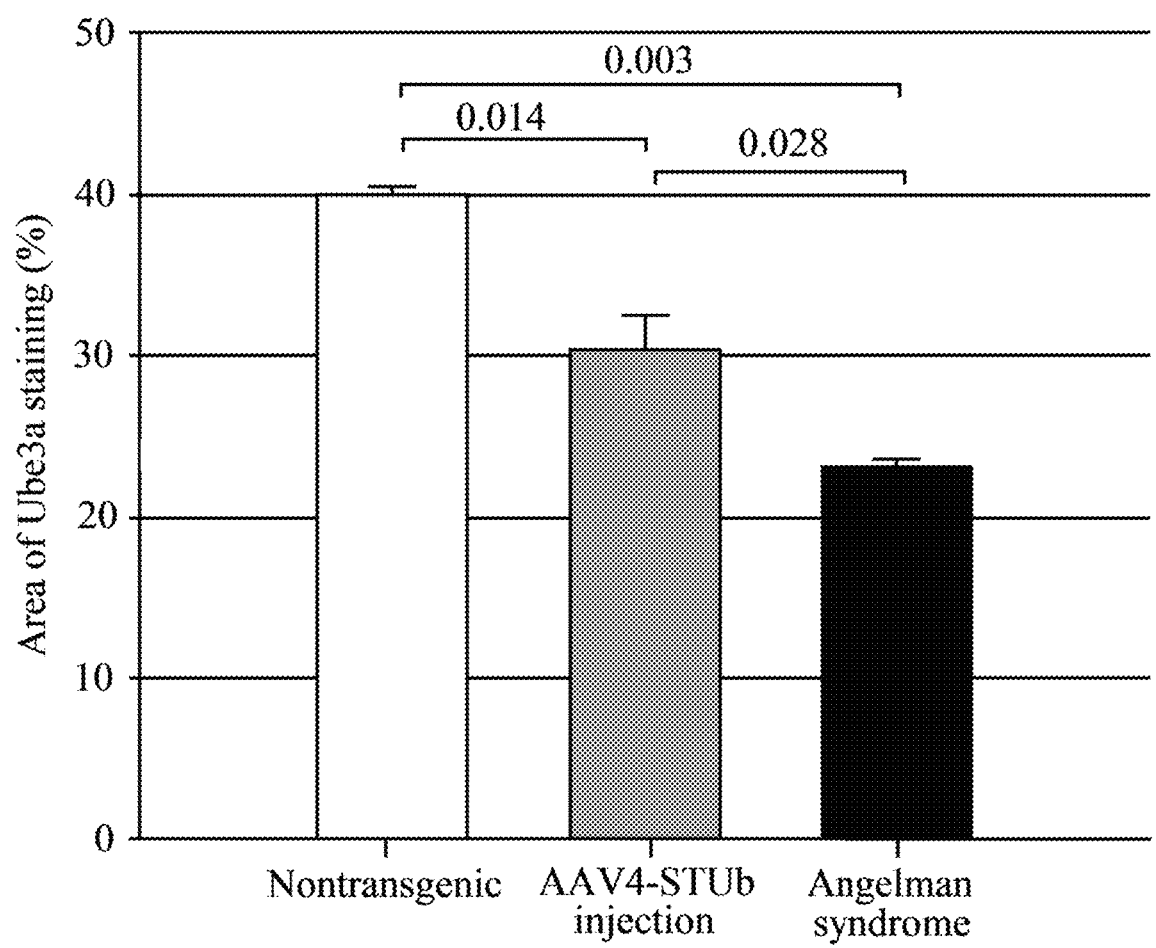
FIG. 4 is a graph of percentage area staining for E6-AP protein. Nontransgenic (Ntg) control mice shows the level of Ube3a expression in a normal mouse brain. Angelman syndrome mice (AS) show staining level in those mice (aka background staining). Injection of AAV4-STUb into the lateral ventricles of an AS mouse shows the level of E6-AP protein staining is increased as compared to an AS mouse. n=2

Nontransgenic (Ntg) control mice shows the level of Ube3a expression in a normal mouse brain, which was about 40%, as seen in FIG. 4. By comparison, Angelman syndrome mice (AS) show Ube3a protein staining levels of about 25%. Insertion of the AAV4-STUb vector into the lateral ventricles of an AS mouse shows the vector increased the level of E6-AP to around 30-35%.

Figure 5:
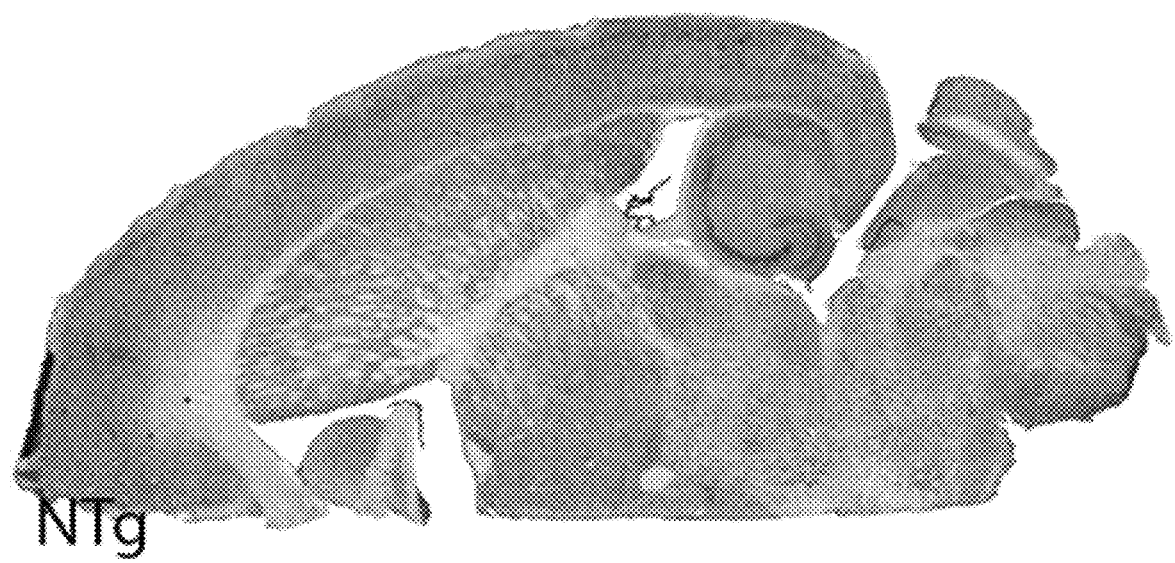
FIG. 5 is a microscopic image of anti-E6-AP staining in a nontransgenic mouse. GFP (green fluorescent protein) is a cytosolic protein which is not secreted. This suggests that the Ube3a is being released from the ependymal cells and taken up in the parenchyma.
Figure 6:
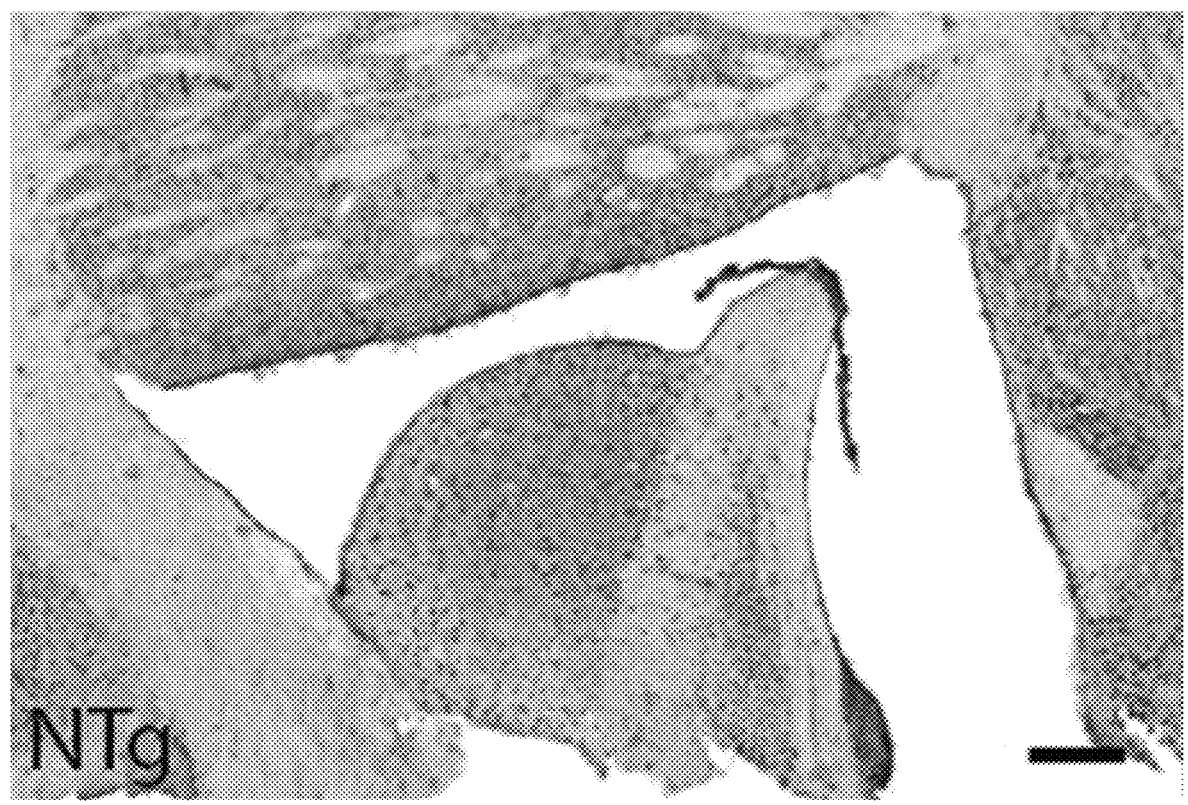
FIG. 6 is a microscopic image of anti-E6-AP staining in a nontransgenic mouse showing higher magnification images of the ventricular system (Lateral ventricle (LV), 3rd ventricle). GFP (green fluorescent protein) is a cytosolic protein which is not secreted. This suggests that the Ube3a is being released from the ependymal cells and taken up in the parenchyma.
Figure 7:
FIG. 7 is a microscopic image of anti-E6-AP staining in an uninjected AS mouse.
Figure 8:
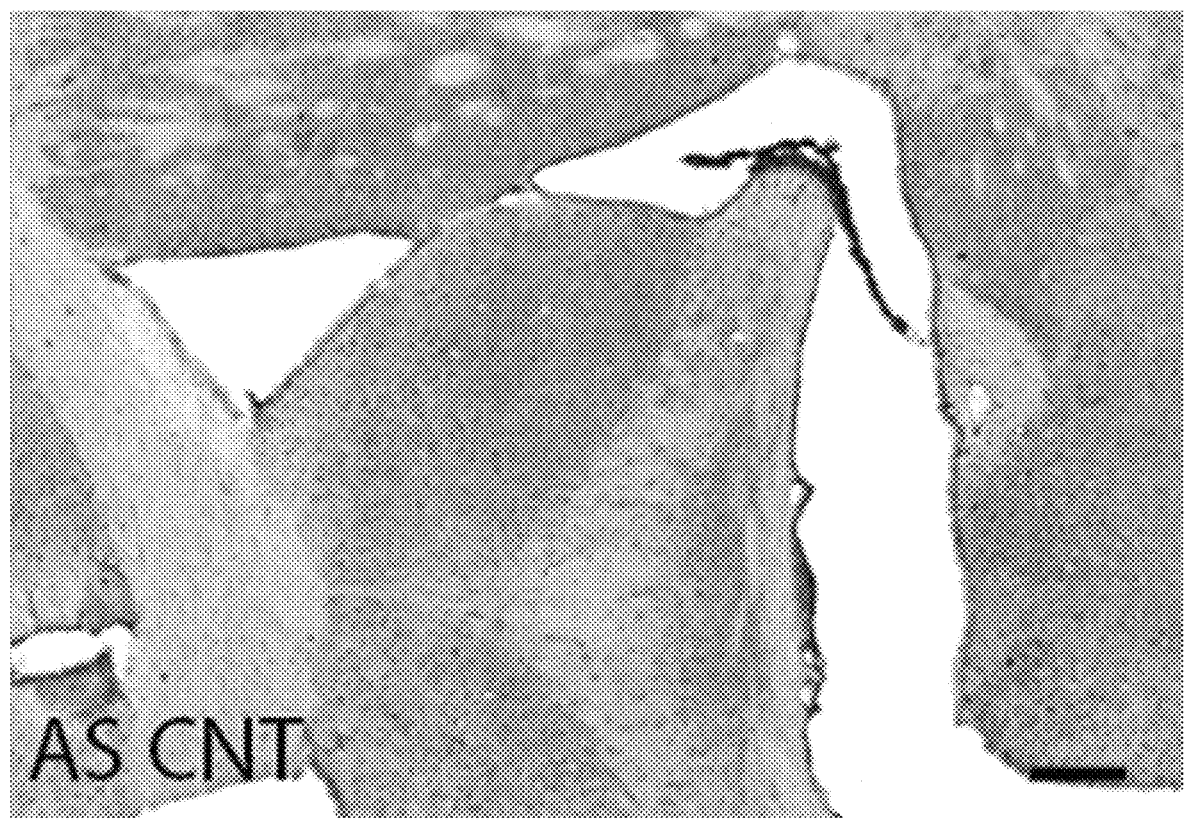
FIG. 8 is a microscopic image of anti-E6-AP staining in an uninjected AS mouse. showing higher magnification images of the ventricular system (Lateral ventricle (LV), 3rd ventricle).
Figure 9:
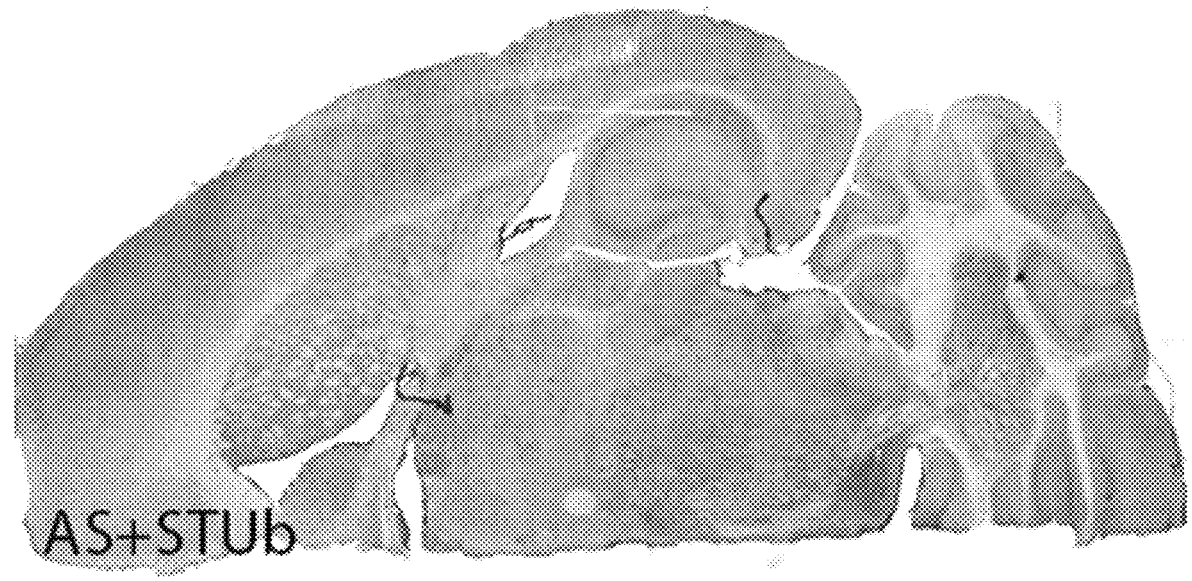
FIG. 9 is a microscopic image of anti-E6-AP staining in an AS mouse injected into the lateral ventricle with AAV4-STUb. Expression can be seen in the ependymal cells but staining is also observed in the parenchyma immediately adjacent to the ventricles (indicated with arrows). GFP (green fluorescent protein) is a cytosolic protein which is not secreted. This suggests that the Ube3a is being released from the ependymal cells and taken up in the parenchyma.
Figure 10:
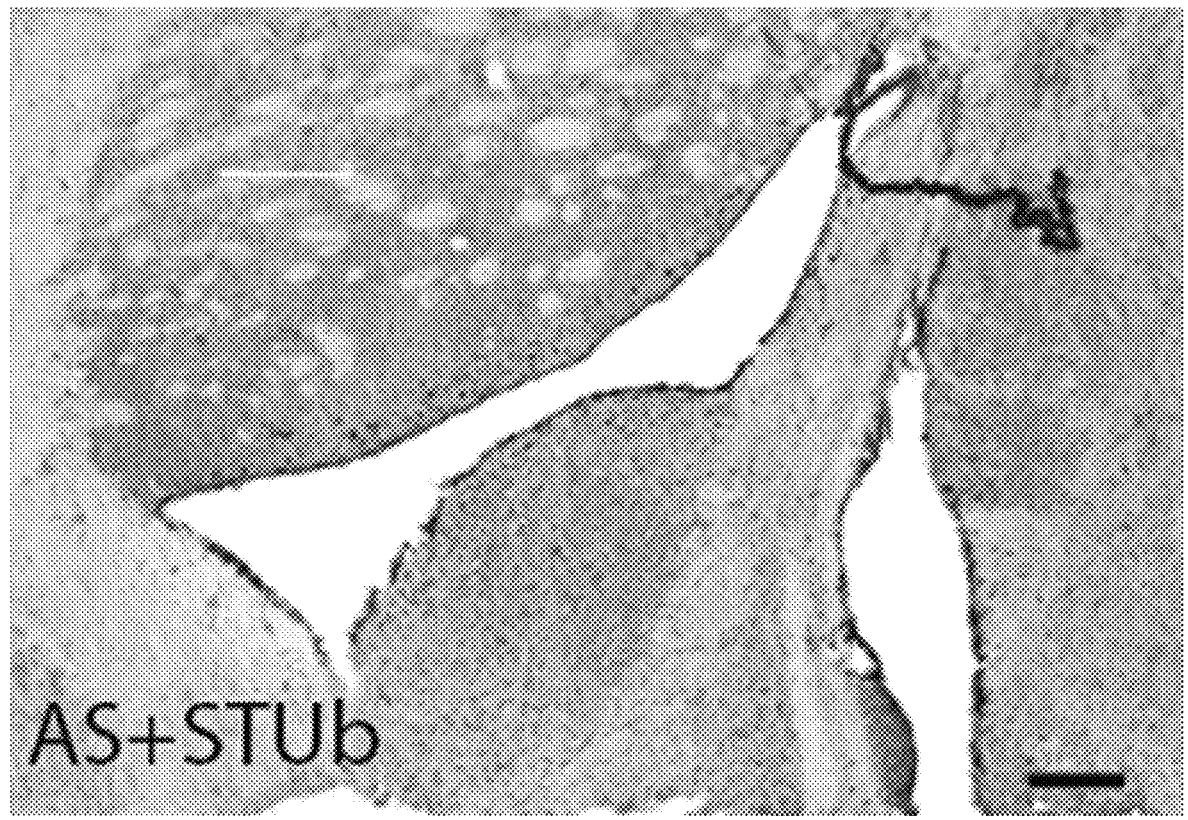
FIG. 10 is a microscopic image of anti-E6-AP staining in an AS mouse injected into the lateral ventricle with AAV4-STUb showing higher magnification images of the ventricular system (Lateral ventricle (LV), $3^{rd}$ ventricle). Expression can be seen in the ependymal cells but staining is also observed in the parenchyma immediately adjacent to the ventricles (indicated with arrows). GFP (green fluorescent protein) is a cytosolic protein which is not secreted. This suggests that the Ube3a is being released from the ependymal cells and taken up in the parenchyma.
Figure 11:
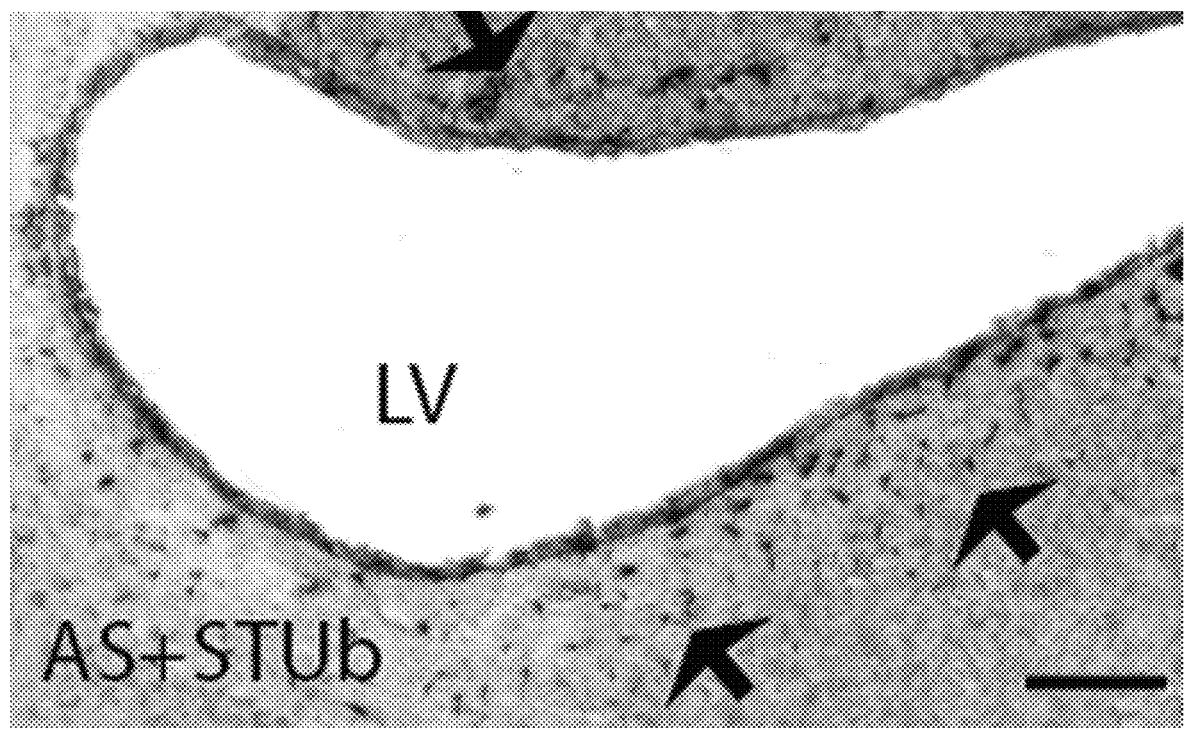
FIG. 11 is a microscopic image of anti-E6-AP staining in an AS mouse injected into the lateral ventricle with AAV4-STUb. Higher magnification images of the ventricular system (Lateral ventricle (LV)) of Ube3a expression after AAV4-STUb delivery. Expression can be seen in the ependymal cells but staining is also observed in the parenchyma immediately adjacent to the ventricles (indicated with arrows). GFP (green fluorescent protein) is a cytosolic protein which is not secreted. This suggests that the Ube3a is being released from the ependymal cells and taken up in the parenchyma.
Figure 12:
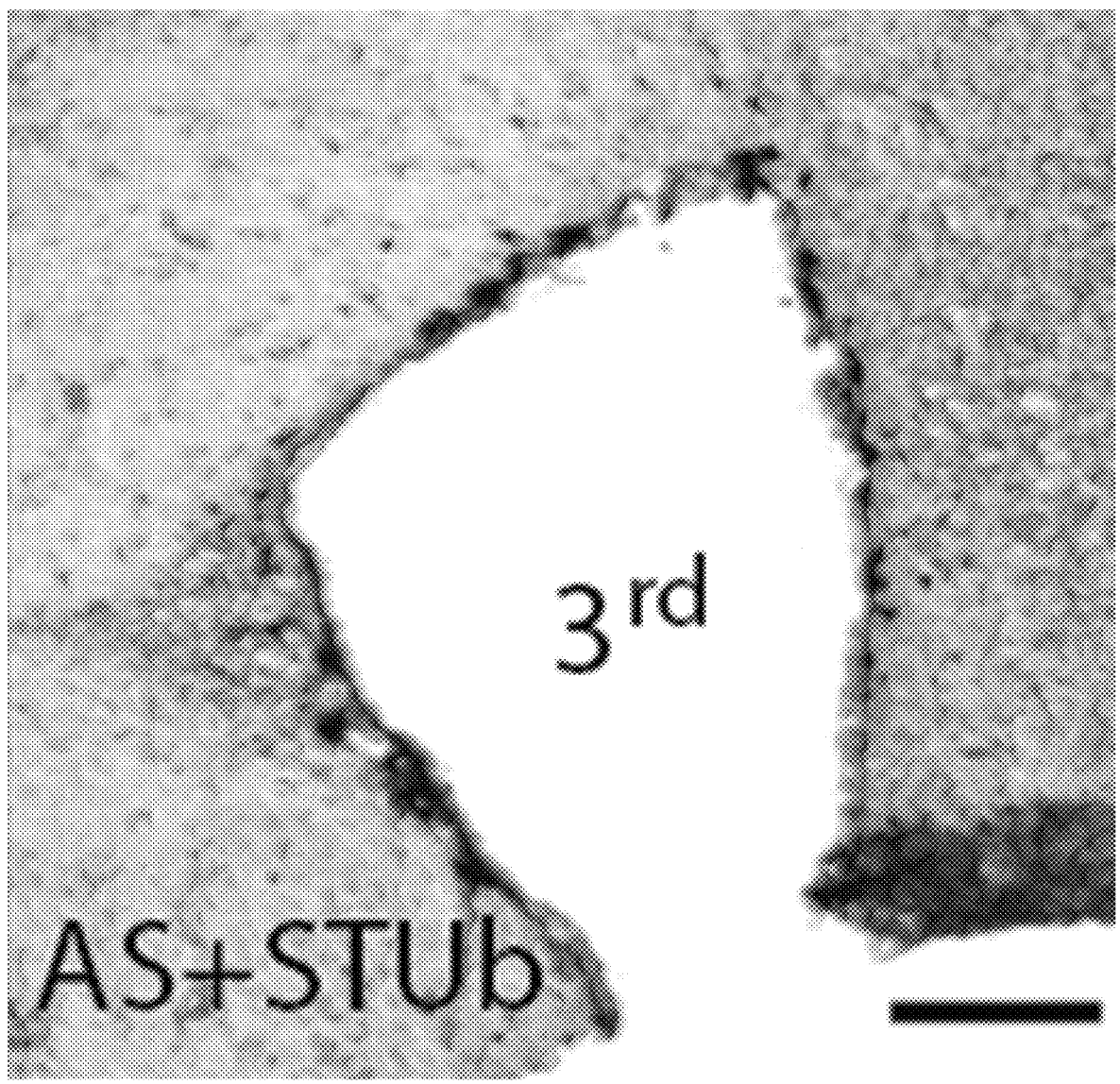
FIG. 12 is a microscopic image of anti-E6-AP staining in an AS mouse injected into the lateral ventricle with AAV4-STUb. Higher magnification images of the ventricular system (3rd ventricle) of Ube3a expression after AAV4-STUb delivery. Expression can be seen in the ependymal cells but staining is also observed in the parenchyma immediately adjacent to the ventricles (indicated with arrows). GFP (green fluorescent protein) is a cytosolic protein which is not secreted. This suggests that the Ube3a is being released from the ependymal cells and taken up in the parenchyma.
Figure 13:
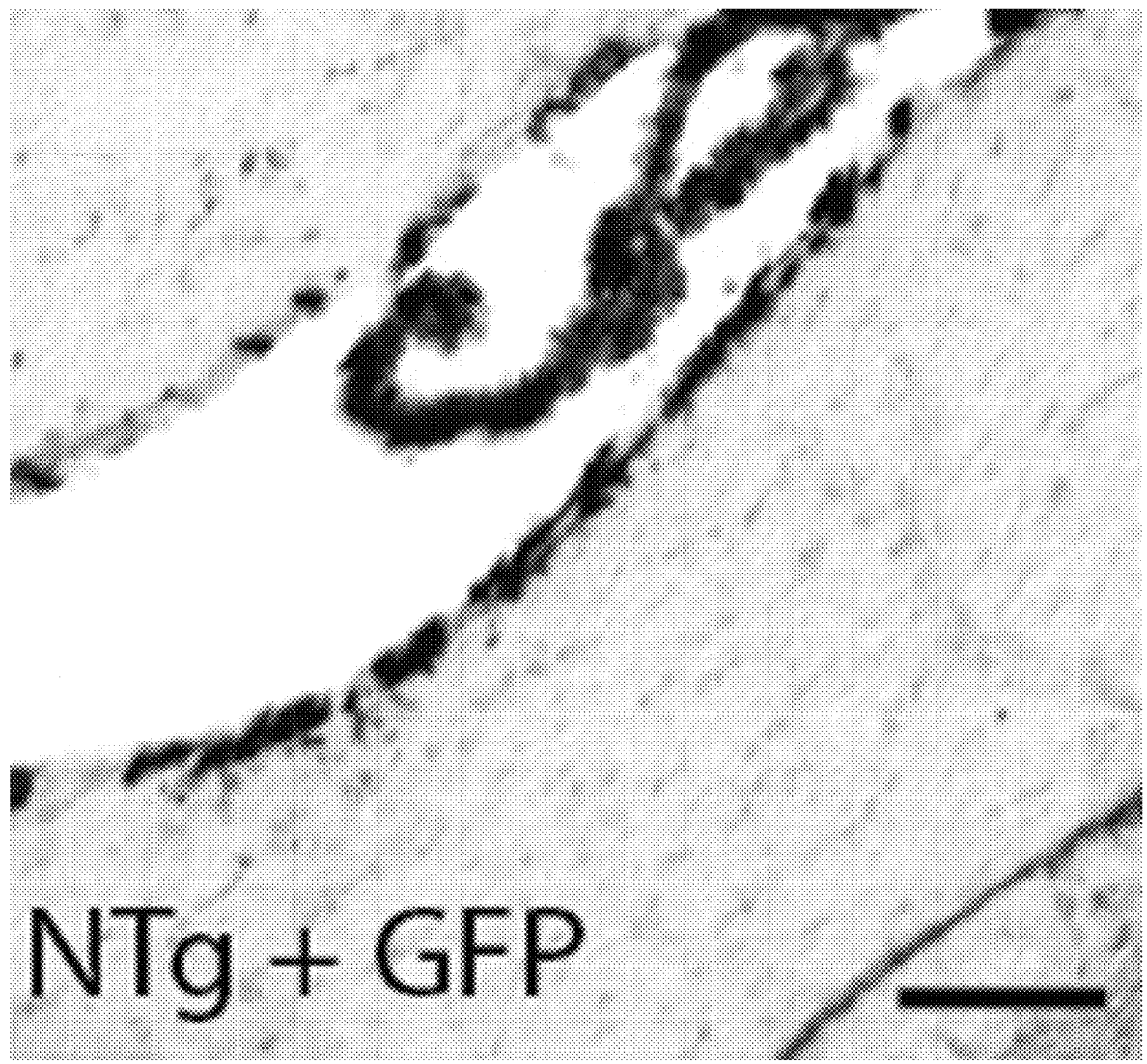
FIG. 13 is a microscopic image of anti-E6-AP staining in a nontransgenic mouse transfected with GFP. Expression is not observed with the AAV4-GFP injections, which shows only transduction of the ependymal and choroid plexus cells. GFP (green fluorescent protein) is a cytosolic protein which is not secreted. This suggests that the Ube3a is being released from the ependymal cells and taken up in the parenchyma.
Figure 14:
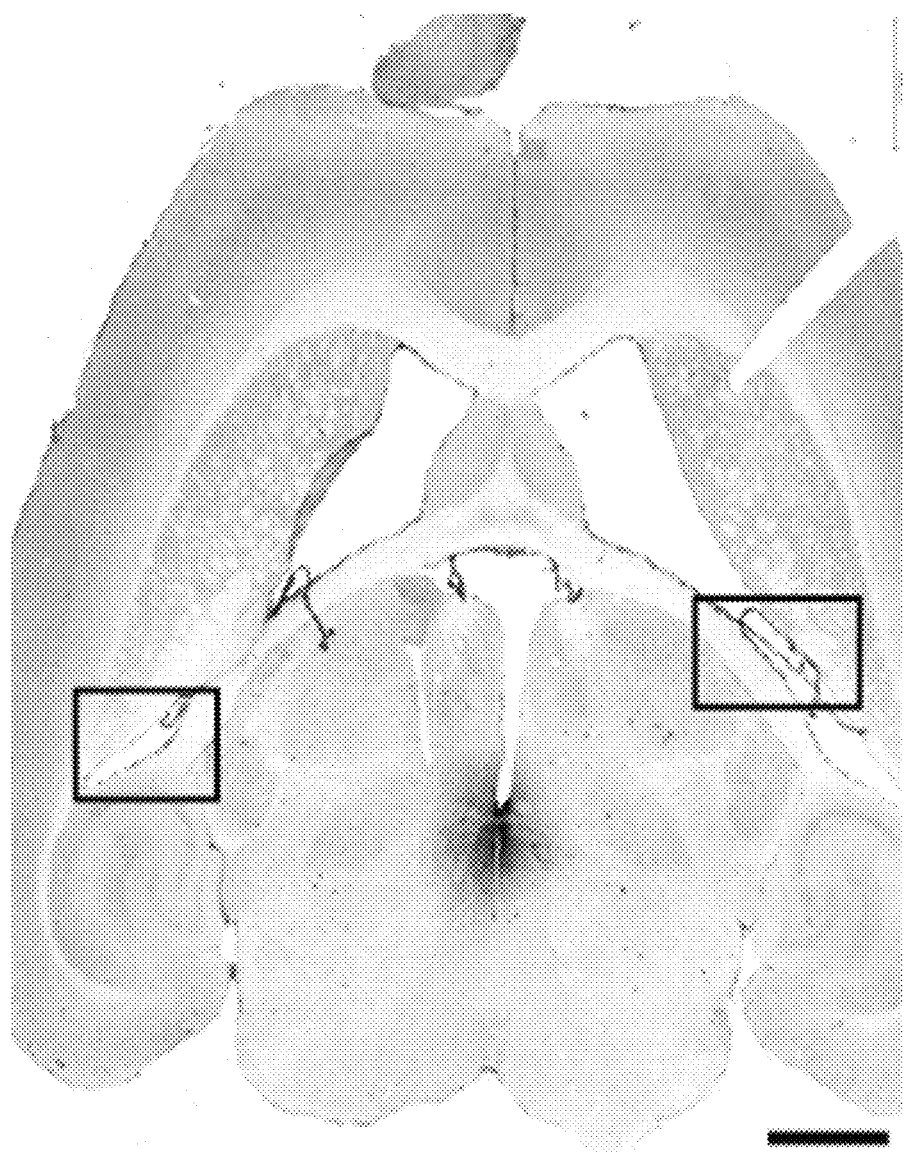
FIG. 14 is a microscopic image of anti-E6-AP staining in an AS mouse injected into the lateral ventricle with AAV4-STUb. Sagittal cross section of the brain of Ube3a expression after AAV4-STUb delivery.
Figure 15:
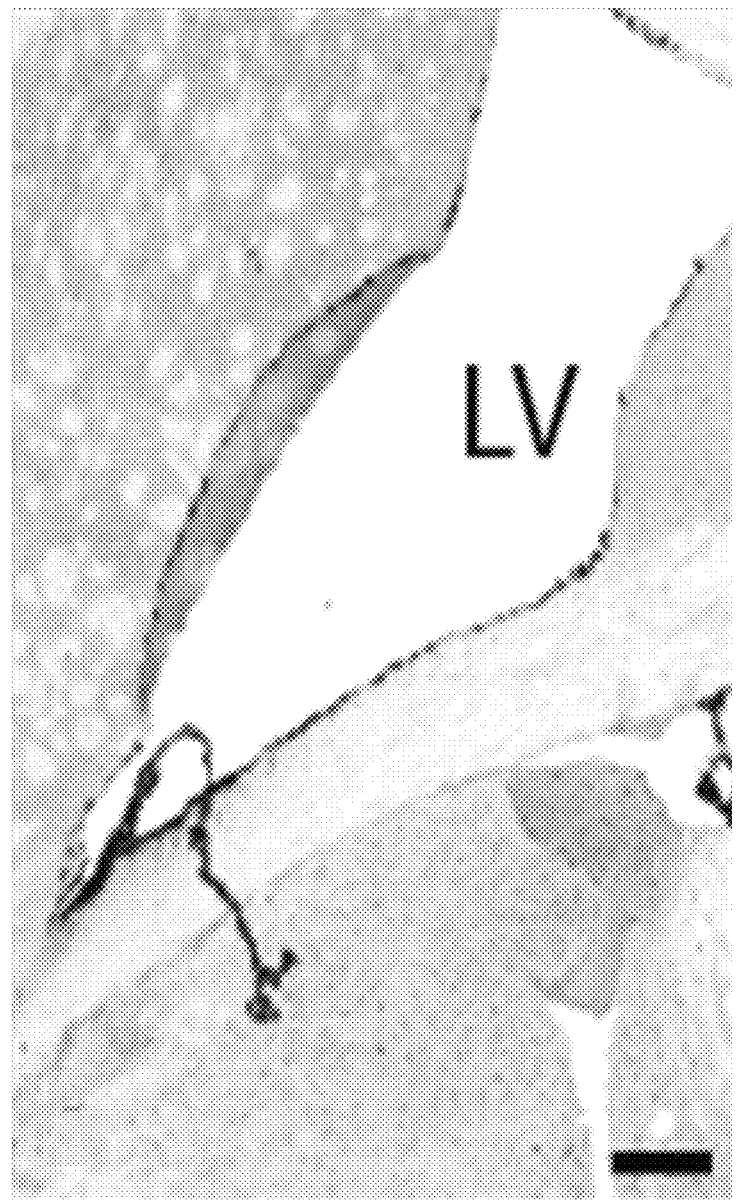
FIG. 15 is a microscopic image of anti-E6-AP staining in an AS mouse injected into the lateral ventricle with AAV4-STUb. Sagittal cross section of the lateral ventricle (LV) in the brain showing Ube3a expression after AAV4-STUb delivery.
Figure 16:
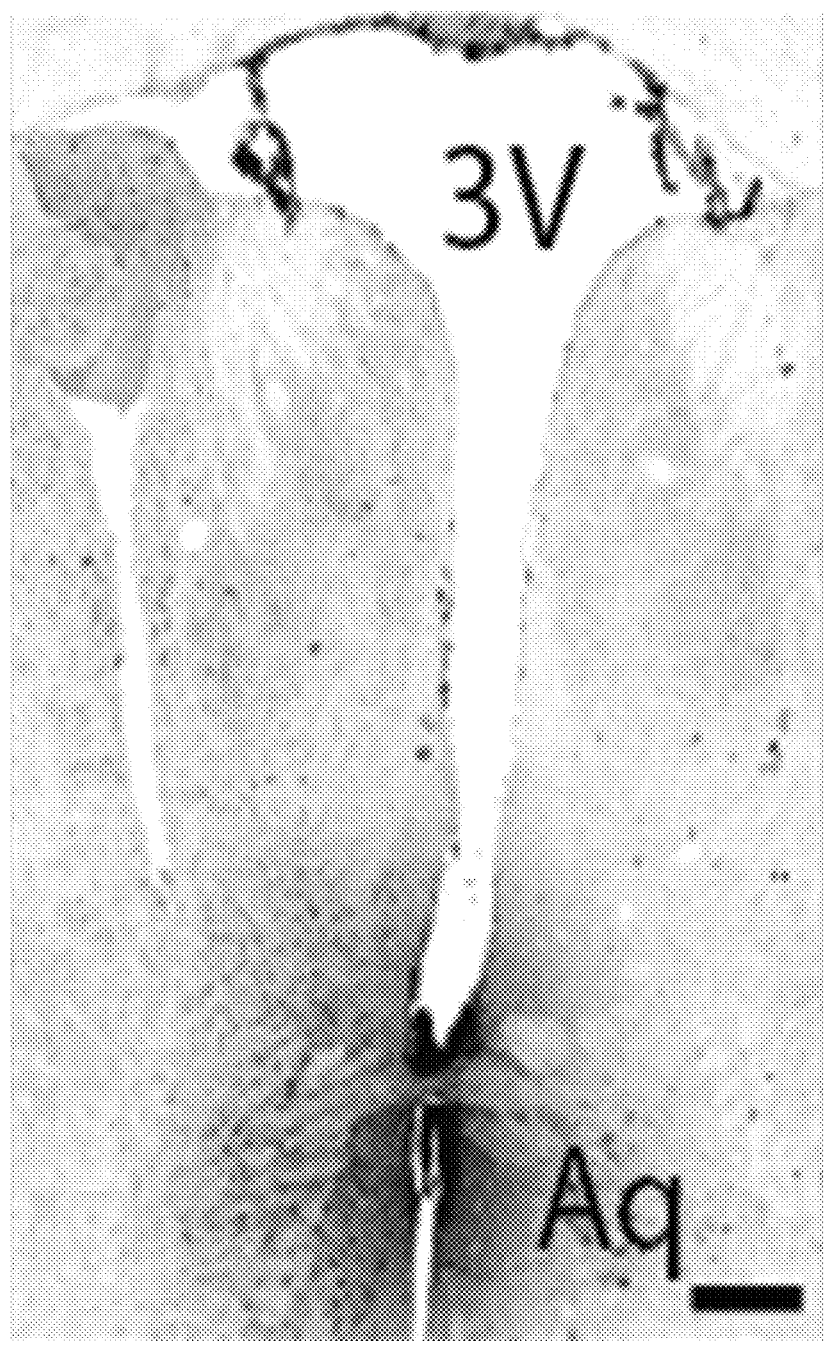
FIG. 16 is a microscopic image of anti-E6-AP staining in an AS mouse injected into the lateral ventricle with AAV4-STUb. Sagittal cross section of the 3rd ventricle (3V) in the brain showing Ube3a expression after AAV4-STUb delivery.
Figure 17:
FIG. 17 is a microscopic image of anti-E6-AP staining in an AS mouse injected into the lateral ventricle with AAV4-STUb. Sagittal cross section of the interior horn of the lateral ventricle (LV) in the brain showing Ube3a expression after AAV4-STUb delivery.
Figure 18:
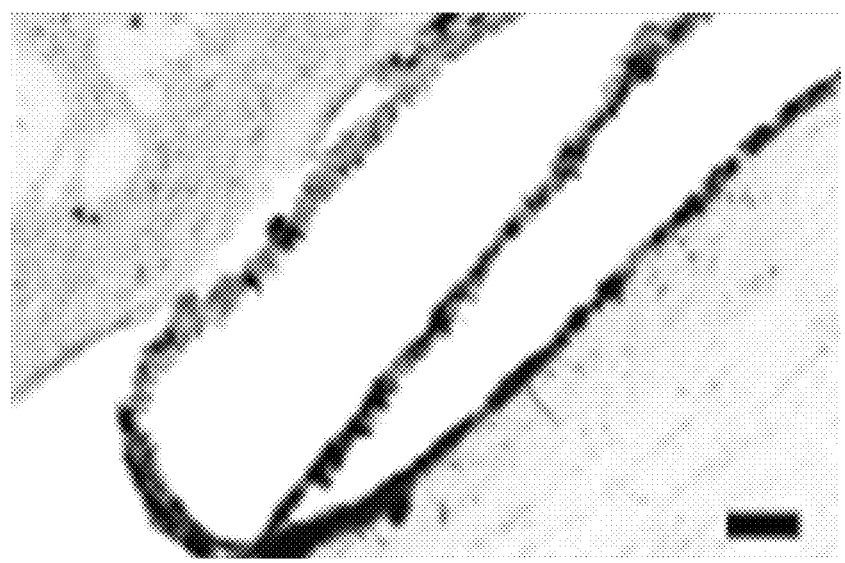
FIG. 18 is a microscopic image of anti-E6-AP staining in an AS mouse injected into the lateral ventricle with AAV4-STUb. Sagittal cross section of the lateral ventricle (4V) in the brain showing Ube3a expression after AAV4-STUb delivery.
Figure 19:
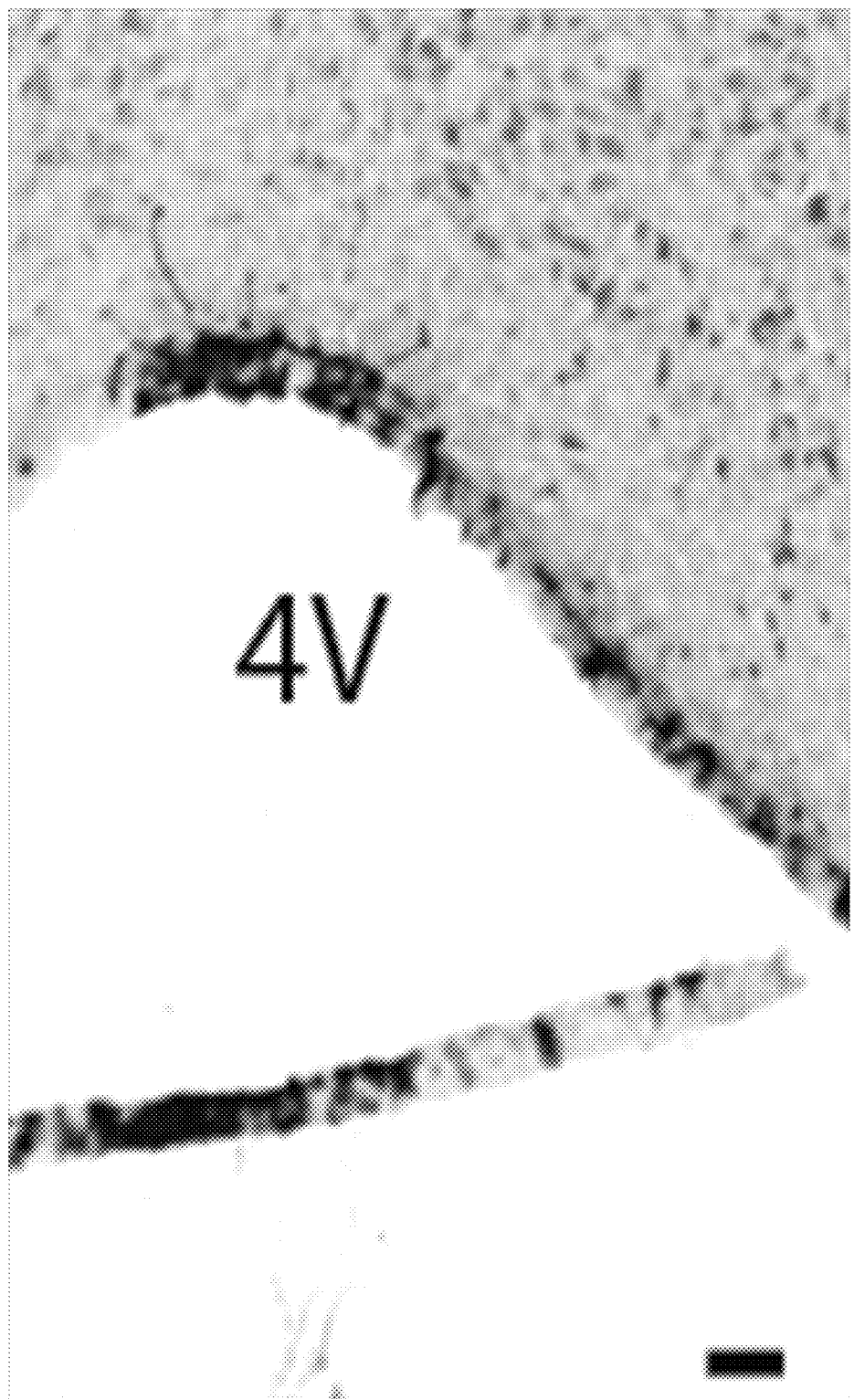
FIG. 19 is a microscopic image of anti-E6-AP staining in an AS mouse injected into the lateral ventricle with AAV4-STUb. Sagittal cross section of the fourth ventricle (LV) in the brain showing Ube3a expression after AAV4-STUb delivery.
Figure 20:
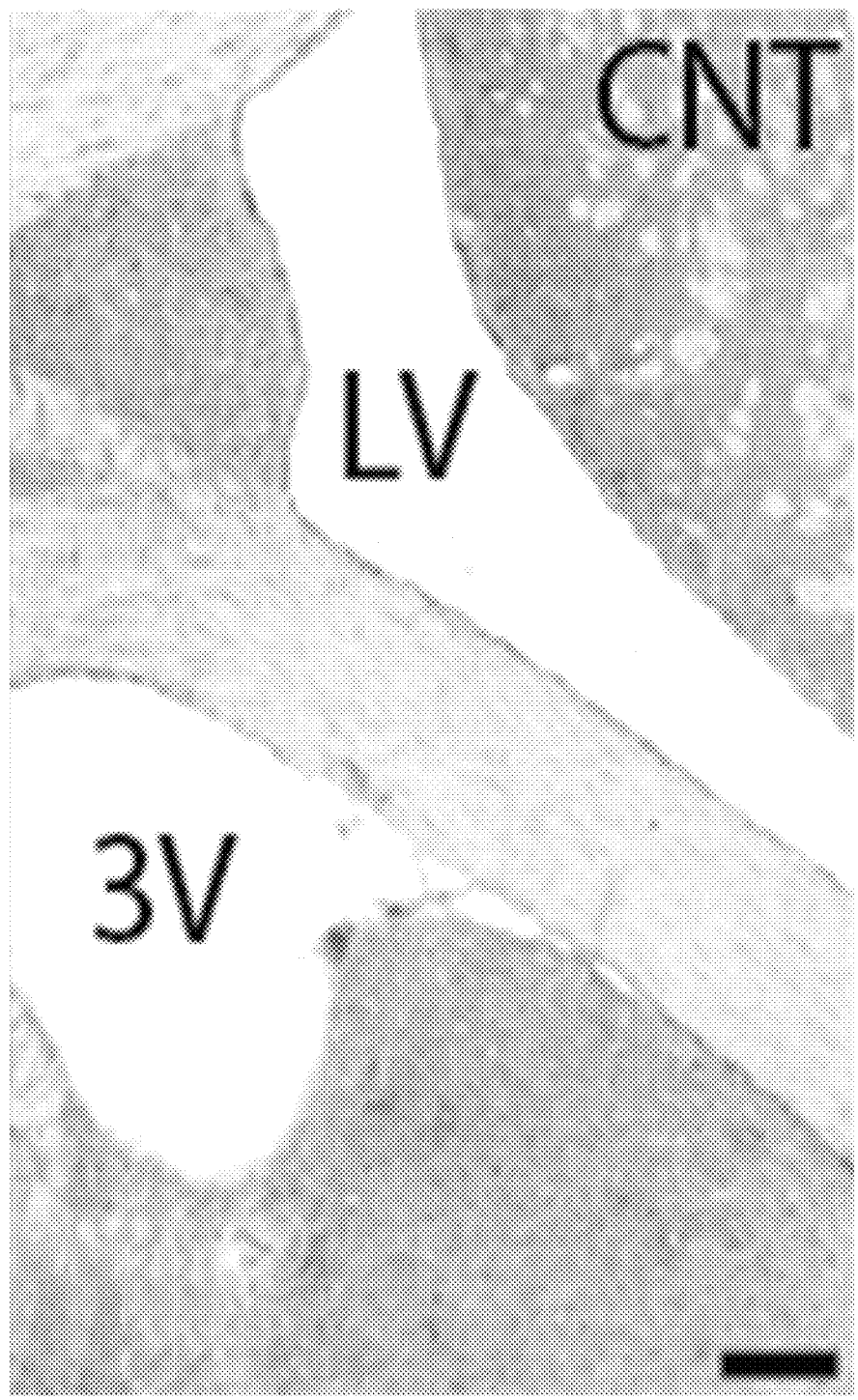
FIG. 20 is a microscopic image of anti-E6-AP staining in an AS mouse injected into the lateral ventricle with AAV4-STUb. Sagittal cross section of the brain with higher magnification images of the ventricular system on the lateral ventricle (LV), and (C) 3rd ventricle (3V) of Ube3a expression after AAV4-STUb delivery.

Immunohistochemical analysis of brain slices indicate nontransgenic mice possess relatively high levels of E6-AP, with region-specific staining, seen in FIGS. 5 and 6. In Angelman syndrome-model mice, staining patterns of E6-AP are similar, but the levels of E6-AP are drastically reduced, seen in FIGS. 7 and 8, as expected. Administration of the mouse UBE3A vector to Angelman syndrome model mice did increase levels of E6-AP, though not to the level of nontransgenic mice, as seen in FIGS. 9 and 10. A detailed analysis of the lateral ventricle shows that the injection of UBE3A vector resulted in uptake of the vector by ependymal cells, as seen in FIG. 11. However, in addition to the uptake of UBE3A vector and expression of E6-AP by ependymal cells, adjacent cells in the parenchyma also stained positive for E6-AP, as seen by arrows in the Figure. Moreover, staining was seen in more distal locations, such as the 3d ventricle, seen in FIG. 12. This indicates that E6-AP was being secreted by the transfected cells and successfully uptaken by adjacent cells, confirming that the construct can be used to introduce E6-AP and that the E6-AP construct can be used as a therapeutic to treat global cerebral deficiency in E6-AP epxression, such as Angelman syndrome. Control treatment using AAV4-GFP vector did not exhibit uptake of the control protein, as seen in FIG. 13, as only transduction of the ependymal and choroid plexus cells.

Detailed analysis of the cornocal cross sections of Anegelman syndrome-model mice confirmed that administration of the UBE3A construct increased levels of E6-AP in and around the the lateral ventricle, as seen in FIGS. 14 through 20.

Example 5

A human vector construct was generated using a pTR plasmid. A *Homo sapien* UBE3A gene was formed from cDNA (AH005553.1);

(SEQ ID No. 6)
```
ggagtagttt actgagccac taatctaaag tttaatactg tgagtgaata ccagtgagta cctttgttaa tgtggataac caatacttgg ctataggaag ttttttagtt gtgtgtttta tnacacgtat ttgactttgt gaataattat ggcttataat ggcttgtctg ttggtatcta tgtatagcgt ttacagtttc ctttaaaaaa catgcattga gttttttaat agtccaaccc ttaaaataaa tgtgttgtat ggccacctga tctgaccact ttctttcatg ttgacatctt taattttaaa actgttttat ttagtgctta aatcttgttn acaaaattgt cttcctaagt aatatgtcta cctttttttt tggaatatgg aatattttgc taactgtttc tcaattgcat tttacagatc aggagaacct cagtctgacg acattgaagc tagccgaatg taagtgtaac ttggttgaga ctgtggttct tattttgagt tgccctagac tgctttaaat tacgtcacat tatttggaaa taatttctgg ttaaaagaaa ggaatcattt agcagtaaat gggagatagg aacataccta ctttttttcc tatcagataa ctctaaacct cggtaacagt ttactaggtt tctactacta gatagataaa tgcacacgcc taaattctta gtcttttgc ttccctggta gcagttgtag ggaaataggg aggttgagga aagagtttaa cagtctcaac gcctaccata tttaaggcat caagtactat gttatagata cagagatgcg taataattag ttttcaccct acagaaattt atattatact caagagtgaa agatgcagaa gcaaataatt tcagtcactg aggtagaatg gtatccaaaa tacaatagta acatgaagga gtactggagt accaggtatg caataggaat ctagtgtaga tggcagggaa gtaagagtgg ccaggaaatg ctaagttcag tcttgaaatg tgactgggaa tcaggcagct atcaactata agtcaaatgt ttacaagctg ttaaaaatga aatactgatt atgtaaaaga aaaccggatt gatgctttaa atagactcat tttcntaatg ctaatttta aaatgataga atcctacaan tcttagctgt aaaccttgtg atttttcagc tgttgtacta aacaacttaa gcacatatac catcagacaa gccccntcc cccttttaa accaaaggaa tgtatactct gttaatacag tcagtaagca ttgacattct ttatcataat atcctagaaa atatttatta actatttcac tagtcaggag ttgtggtaaa tagtgcatct ccattttcta cttctcatct tcatacacag gttaatcact tcagtgcttg actaactttt gccttgatga tatgttgagc tttgtacttg agagctgtac taatcactgt gcttattgtt tgaatgtttg gtacaggaag cgagcagctg caaagcatct aatagaacgc tactaccacc agttaactga gggctgtgga aatgaagcct gcacgaatga gttttgtgct tcctgtccaa cttttcttcg tatggataat aatgcagcag ctattaaagc cctcgagctt tataagatta atgcaaaact ctgtgatcct catccctcca agaaaggagc aagctcagct taccttgaga actcgaaagg tgcccccaac aactcctgct ctgagataaa aatgaacaag aaaggcgcta gaattgattt taaaggtaag atgtttatt ttcaattgag aattgttgcc tgaaaaccat gtgggagatt taaatgtatt agttttatt tgttttttct tctgtgacat aaagacattt tgatatcgta gaaccaattt tttattgtgg taacggacag gaataataac tacatttac aggtctaatc attgctaatt agaagcagat catatgccaa aagttcattt gttaatagat tgatttgaac tttttaaaat tcttaggaaa aatgtattaa gtggtagtga atctccaaaa ctatttaaga gctgtattat gattaatcag tacatgacat attggttcat atttataatt aaagctatac attaatagat atcttgatta taaagaaagt ttaaactcat gatcttatta agagttatac attgttgaaa gaatgtaaaa gcatgggtga ggtcattggt ataggtaggt agttcattga aaaaaatagg taagcattaa attttgtttg ctgaatctaa gtattagata ctttaagagt tgtatatcat aaatgatatt gagcctagaa tgtttggctg ttttactttt agaactttt gcaacagagt aaacatacat attatgaaaa taaatgttct ctttttcct ctgatttct agatgtgact tacttaacag aagagaaggt atatgaaatt
```

-continued

```
cttgaattat gtagagaaag agaggattat tccccttttaa
tccgtgttat tggaagagtt ttttctagtg ctgaggcatt
ggtacagagc ttccggaaag ttaaacaaca caccaaggaa
gaactgaaat ctcttcaagc aaaagatgaa gacaaagatg
aagatgaaaa ggaaaaagct gcatgttctg ctgctgctat
ggaagaagac tcagaagcat cttcctcaag gataggtgat
agctcacagg gagacaacaa tttgcaaaaa ttaggccctg
atgatgtgtc tgtggatatt gatgccatta gaagggtcta
caccagattg ctctctaatg aaaaaattga aactgccttt
ctcaatgcac ttgtatattt gtcacctaac gtggaatgtg
acttgacgta tcacaatgta tactctcgag atcctaatta
tctgaatttg ttcattatcg taatggaaaa tagaaatctc
cacagtcctg aatatctgga aatggctttg ccattatttt
gcaaagcgat gagcaagcta cccccttgcag cccaaggaaa
actgatcaga ctgtggtcta aatacaatgc agaccagatt
cggagaatga tggagacatt tcagcaactt attacttata
aagtcataag caatgaattt aacagtcgaa atctagtgaa
tgatgatgat gccattgttg ctgcttcgaa gtgcttgaaa
atggtttact atgcaaatgt agtgggaggg gaagtggaca
caaatcacaa tgaagaagat gatgaagagc ccatccctga
gtccagcgag ctgacacttc aggaactttt gggagaagaa
agaagaaaca gaaaggtcc tcgagtggac cccctggaaa
ctgaacttgg tgttaaaacc ctggattgtc gaaaaccact
tatcccttt gaagagttta ttaatgaacc actgaatgag
gttctagaaa tggataaaga ttatacttt ttcaaagtag
aaacagagaa caaattctct tttatgacat gtccctttat
attgaatgct gtcacaaaga atttgggatt atattatgac
aatagaattc gcatgtacag tgaacgaaga atcactgttc
tctacagctt agttcaagga cagcagttga atccatattt
gagactcaaa gttagacgtg accatatcat agatgatgca
cttgtccggg taagttgggc tgctagatta aaaacctaat
aatggggata tcatgataca gttcagtgaa ttcatttaa
aagtgactga aaaaaatgat accatatagc ataggaacac
atggacattt ctgatcttat ataagtatta tactttgtt
gttcctgtgc aagtttatag atgtgttcta caaagtatcg
gttgtattat ataatggtca tgctatcttt gaaaagaat
gggttttcta atcttgaaa actaaatcca aagtttcttt
cattcagaag agaatagagt gttggacaaa gaccagaaca
agagaaatgt ggagataccc aataataagt gtggatgtgc
agtcttgaac tgggagtaat ggtacagtaa aaccatacca
taaaattata ggtagtgtcc aaaaaattcc atcgtgtaaa
```

-continued

```
attcagagtt gcattattgt ggacttgaag aagcagttgt
atgtgggacg gtatcgataa gcttgatatc gaattcctgc
agcccggggg atccactagt gtggtaatta atactaagtc
ttactgtgag agaccataaa ctgctttagt attcagtgta
tttttcttaa ttgaaatatt taacttatga cttagtagat
actaagactt aacccttgag tttctattct aataaaggac
tactaatgaa caattttgag gttagacctc tactccattg
tttttgctga aatgatttag ctgcttttcc atgtcctgtg
tagtccagac ttaacacaca agtaataaaa tcttaattaa
ttgtatgtta atttcataac aaatcagtaa agttagcttt
ttactatgct agtgtctgtt ttgtgtctgt cttttgatt
atctttaaga ctgaatcttt gtcttcactg gcttttatc
agtttgcttt ctgtttccat ttacatacaa aaagtcaaaa
atttgtattt gtttcctaat cctactcctt gttttatt
tgtttttttc ctgatactag caatcatctt cttttcatgt
ttatctttc aatcactagc tagagatgat cgctatggaa
aatcctgcag acttgaagaa gcagttgtat gtggaatttg
aaggagaaca aggagttgat gagggaggtg tttccaaaga
attttttcag ctggttgtgg aggaaatctt caatccagat
attggtaaat acattagtaa tgtgattatg gtgtcgtatc
atcttttgag ttagttattt gtttatctta ctttgtaaat
attttcagct atgaagagca gcaaaagaag gatttggtat
ggattaccca gaatcacaca tcatgactga atttgtaggt
tttaggaact gatttgtatc actaatttat tcaaattctt
ttatttctta gaaggaatat tctaatgaag gaaattatct
ctttggtaaa ctgaattgaa agcactttag aatggtatat
tggaacagtt ggagggattt cttgctttt tgttgtctaa
aaccatcatc aaactcacgg ttttcctgac ctgtgaactt
caaagaacaa tggtttgaag agtattgaga gactgtctca
caagtatgtc atgctcaaag ttcagaaaca ctagctgata
tcacattaat taggtttatt tgctataaga tttcttgggg
cttaatatan gtagtgttcc cccaaacttt ttgaactcca
gaactctttt ctgccctaac agtagctact caggagctga
ggcaggagaa ttgtttgaac ctaggaggca gaggttgcag
tgagctgaga tcgtgccact ccagcccacc cctgggtaac
agagcgagac tccatctcaa agaaaaaaat gaaaaattgt
tttcaaaaat agtacgtgtg gtacagatat aagtaattat
atttttataa atgaaacact ttggaaatgt agccattttt
tgtttttta tgtttatttt tcagctatgg gtggataaag
catgaatata actttctta tgtgttagta gaaaattaga
```

```
aagcttgaat ttaattaacg tatttttcta cccgatgcca
ccaaattact tactacttta ttcctttggc ttcataaaat
tacatatcac cattcacccc aatttatagc agatatatgt
ggacattgtt ttctcaagtg ctaatataat agaaatcaat
gttgcatgcc taattacata tattttaaat gttttatatg
cataattatt ttaagtttat atttgtatta ttcatcagtc
cttaataaaa tacaaaagta atgtatttt aaaaatcatt
tcttataggt atgttcacat acgatgaatc tacaaaattg
ttttggttta atccatcttc ttttgaaact gagggtcagt
ttactctgat tggcatagta ctgggtctgg ctatttacaa
taactgtata ctggatgtac attttcccat ggttgtctac
aggaagctaa tggggaaaaa aggaactttt cgtgacttgg
gagactctca cccagtaagt tctttgtcat ttttttaatt
cagtctctta gatttatttt aaatgcaaaa atttaattta
tgtcaaaatt ttaaagtttt tgtttagaat ctttgttgat
actcttatca ataagataaa aatgttttaa tctgaccgaa
gtaccagaaa cacttaaaaa ctcaaagggg acattttta
tatattgctg tcagcacgaa gctttcgtaa gattgatttc
atagagaagt gtttctaaac attttgtttg tgttttagtg
aaatcttaag agataggtaa aaatcagagt agccctggct
aagggtcttg gtagttacaa cgagtgtgcc tgctcctacc
accccaccc ccaccttgag acaccacaga atttctcata
gagcacagtg tgaattctat tgctaaattg gtggtatggg
gtttctcagc agagaatggg acatcacagt gactgacaat
ctttcttta taggttggaa actatttggg ggactggagg
gatactgtct acacttttta caattttat tgataagatt
tttgttgtct tctaagaaga gtgatataaa ttatttgttg
tattttgtag ttctatggtg gcctcaattt accatttctg
gttgctaggt tctatatcag agtttaaaag atttattgga
gtatgaaggg aatgtggaag atgacatgat gatcactttc
cagatatcac agacagatct ttttggtaac ccaatgatgt
atgatctaaa ggaaaatggt gataaaattc caattacaaa
tgaaaacagg aagtaataa atgttttat gtcacatttt
gtctcttcat taacactttc aaagcatgta tgcttataat
ttttaaagaa gtatctaata tagtctgtac aaaaaaaaa
caagtaacta agtttatgta aatgctagag tccactttc
taaatcttgg atataagttg gtatgaaagc acacagttgg
gcactaaagc cccttttaga gaagaggac atgaagcagg
agatagttaa tagctaagtg tggttgtagt ataaagcaag
aagcagggtc tttcttgtat taagctgtaa gcaggaacct
catgattaag gtctttatca cagaacaaat aaaaattaca
tttaatttac acatgtatat cctgtttgtg ataaaaatac
atttctgaaa agtatacttt acgtcagatt tgggttctat
tgactaaaat gtgttcatcg ggaatgggaa taacccagaa
cataacaagc aaaaaattat gacaaatata tagtataacct
ttaagaaaca tgtttatatt gatataatt tttgattaaa
tattatacac actaagggta caangcacat ttttccttta
tganttngat acagtagttt atgtgtcagt cagatacttc
cacattttg ctgaactgga tacagtaagc agcttaccaa
atattctatg gtagaaaact nggacttcct ggtttgctta
aatcaaatat attgtactct cttaaaacgg ttggcattta
taaatagatg gatacatggt ttaaatgtgt ctgttnacat
acctagttga gagaacctaa agaattttct gcgtctccag
catttatatt cagttctgtt taatacatta tcgaaattga
catttataag tatgacagtt ttgtgtatat ggccttttca
tagcttaata ttggctgtaa cagagaattg tgaaattgta
agaagtagtt ttctttgtag gtgtaaaatt gaattttaa
gaatattctt gacagtttta tgtatatggc cttttcatag
cttaatattg gctataacag agaattgtga aattgttaag
aagtaggtgt aaaattgaat ttttaagaat attcttgaat
gtttttttct tggaaaaatt aaaaagctat gcagcccaat
aacttgtgtt ttgtttgcat agcatattat aagaagttct
tgtgattaat gttttctaca ggaatttgtc aatctttatt
ctgactacat tctcaataaa tcagtagaaa aacagttcaa
ggcttttcgg agaggttttc atatggtgac caatgaatct
cccttaaagt acttattcag accagaagaa attgaattgc
ttatatgtgg aagccgggta agaaagcagg tgtctgcaaa
aagtcatgta tcgatttatt gtttgtaatg atacagtagt
atagcagata actaagacat attttcttga atttgcagaa
tctagatttc caagcactag aagaaactac agaatatgac
ggtggctata ccagggactc tgttctgatt aggtgaggta
cttagttctt cagaggaaga tttgattcac caaaggggtg
tgtgatttg cttcagacct ttatctctag gtactaattc
ccaaataagc aaactcacaa attgtcatct atatacttag
atttgtattt gtaatataat caccattttt cagagctaat
cttgtgattt atttcatgaa tgaagtgttg ttatatataa
gtctcatgta atctcctgca tttggcgtat ggattatcta
gtattcctca ctggttagag tatgcttact gctggttaga
agataattaa aataaggcta ccatgtctgc aattttttcct
ttcttttgaa ctctgcattt gtgaactgtt acatggcttc
ccaggatcaa gcacttttg agtgaaatgg tagtctttta
```

```
tttaattctt aagataatat gtccagatac atactagtat
ttccatttta caccctaaaa aactaagccc tgaattctca
cagaaagatg tagaggttcc cagttctatc tgcttttaaa
caaatgccct tactactcta ctgtctactt ctgtgtacta
catcatcgta tgtagttgtt tgcatttggg ccagttggtt
ggggcagggg tcttttttc ttttgtccct taatctgtat
cacttttcc tcccaaagtt gagttaaagg atgagtagac
caggagaata aaggagaaag gataaataaa atatataccc
aaaggcacct ggagttaatt tttccaaata ttcatttcag
tcttttcaa ttcataggat tttgtctttt gctcattact
gactgcataa tgtgattata ccatagttta aatagtcact
tcctgttact acacacttgg gttttctcaa tttttacta
ttgtagtact aatatttac tatattgtaa tctaatccaa
attttacgt attcagagct gttcaggata aatttgcttg
gaaatttta aatcaccaga agtgatacta tcctgataat
taacttccaa gttgtctctt aatatagttt taatgcaaat
cataagctta tgttagtacc agtcataatg aatgccaaac
tgaaaccagt attgtatttt ttctcattag ggagttctgg
gaaatcgttc attcatttac agatgaacag aaaagactct
tcttgcagtt tacaacgggc acagacagag cacctgtggg
aggactagga aaattaaaga tgattatagc caaaaatggc
ccagacacag aaaggtaggt aattattaac ttgtgactgt
atacctaccg aaaaccttgc attcctcgtc acatacatat
gaactgtctt tatagtttct gagcacattc gtgattttat
atacaaatcc ccaaatcata ttagacaatt gagaaaatac
tttgctgtca ttgtgtgagg aaacttttaa gaaattgccc
tagttaaaaa ttattatggg gctcacattg gtttggaatc
aaattagtgt gattcattta cttttttgat tcccagcttg
ttaattgaaa gccatataac atgatcatct atttagaatg
gttacattga ggctcggaag attatcattt gattgtgcta
gaatcctgtt atcaaatcat tttcttagtc atattgccag
cagtgtttct aataagcatt taagagcaca cactttgcag
tcttgtaaaa caggtttgag tattttctcc accttagagg
aagttacttg acttctcagt gacctaacct ctaaagtgca
tttactgatg tcctctctgt ggttttgttg tggaaagatt
tagttaaatg aactgtaaga attcagtacc taaaatggta
tctgttatgt agtaaaaact caatggatac agtatcttat
catcgtcact agctttgagt aatttatagg ataaaggcaa
cttggtagtt acacaacaaa aagtttatga tttgcattaa
tgtatagttt gcattgcaga ccgtctcaac tatatacaat
ctaaaaatag gagcatttaa ttctaagtgt atttcccatg
acttacagtt ttcctgtttt tttcccttt tctctattta
ggttacctac atctcatact tgctttaatg tgcttttact
tccggaatac tcaagcaaag aaaaacttaa agagagattg
ttgaaggcca tcacgtatgc caaaggattt ggcatgctgt
aaaacaaaac aaaacaaaat aaaacaaaaa aaaggaagga
aaaaaaaaga aaaatttaa aaaatttaa aaatataacg
agggataaat ttt,
```
which encodes for;

```
(SEQ ID No. 7)
MKRAAAKHLIERYYHQLTEGCGNEACTNEFCASCPTFLRMDNNAAAI
KALELYKINAKLCDPHPSKKGASSAYLENSKGAPNNSCSEIKMNKKG
ARIDFKDVTYLTEEKVYEILELCREREDYSPLIRVIGRVFSSAEALV
QSFRKVKQHTKEELKSLQAKDEDKDEDEKEKAACSAAAMEEDSEASS
SRIGDSSQGDNNLQKLGPDDVSVDIDAIRRVYTRLLSNEKIETAFLN
ALVYLSPNVECDLTYHNVYSRDPNYLNLFIIVMENRNLHSPEYLEMA
LPLFCKAMSKLPLAAQGKLIRLWSKYNADQIRRMMETFQQLITYKVI
SNEFNSRNLVNDDDAIVAASKCLKMVYYANVVGGEVDTNHNEEDDEE
PIPESSELTLQELLGEERRNKKGPRVDPLETELGVKTLDCRKPLIPF
EEFINEPLNEVLEMDKDYTFFKVETENKFSFMTCPFILNAVTKNLGL
YYDNRIRMYSERRITVLYSLVQGQQLNPYLRLKVRRDHIIDDALVRL
EMIAMENPADLKKQLYVEFEGEQGVDEGGVSKEFFQLVVEEIFNPDI
GMFTYDESTKLFWFNPSSFETEGQFTLIGIVLGLAIYNNCILDVHFP
MVVYRKLMGKKGTFRDLGDSHPVLYQSLKDLLEYEGNVEDDMMITFQ
ISQTDLFGNPMMYDLKENGDKIPITNENRKEFVNLYSDYILNKSVEK
QFKAFRRGFHMVTNESPLKYLFRPEEIELLICGSRNLDFQALEETTE
YDGGYTRDSVLIREFWEIVHSFTDEQKRLFLQFTTGTDRAPVGGLGK
LKMIIAKNGPDTERLPTSHTCFNVLLLPEYSSKEKLKERLLKAITYA
KGFGML.
```

The cDNA was subcloned and sequenced. The UBE3A, variant 1 gene (SEQ ID No. 6) was fused to one of three genes encoding a section signaling peptide, based on GDNF;

```
(SEQ ID No. 8)
ATGAAGTTATGGGATGTCGTGGCTGTCTGCCTGGTGCTGCTCCACAC
CGCGTCCGCC,
```
from insulin protein;

```
(SEQ ID No. 9)
ATGGCCCTGTGGATGCGCCTCCTGCCCCTGCTGGCGCTGCTGGCCCT
CTGGGGACCTGACCCAGCCGCAGCC,
```
or from IgK;

```
(SEQ ID No. 10)
ATGGAGACAGACACACTCCTGCTATGGGTACTGCTGCTCTGGGTTCC
AGGTTCCACTGGT.
```

The construct was inserted into the hSTUb vector, under a CMV chicken-beta actin hybrid promoter or human ubiquitin c promoter. Woodchuck hepatitis post-transcriptional regulatory element (WPRE) is present to increase expression levels.

The UBE3A-seretion signal construct was then attached to a cellular uptake peptide (cell penetrating peptide); either a HIV TAT sequence

```
                                          (SEQ ID No. 5)
YGRKKRRQRRR;
or

HIV TATk sequence
                                         (SEQ ID No. 11)
YARKAARQARA.
```

Figure 21:
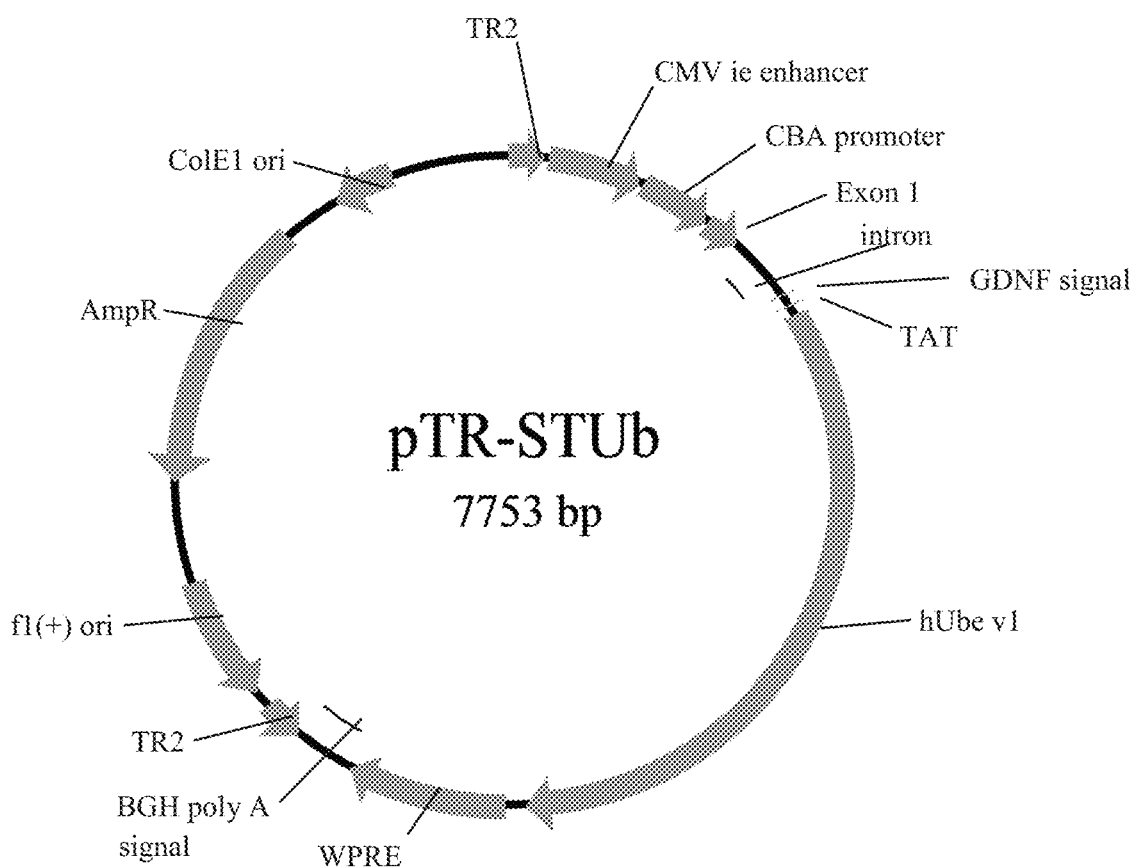
FIG. 21 is a map of the human UBE3A vector construct used in the present invention. Major genes are noted.

The human UBE3A vector, seen in FIG. 21, is then then transformed into *E. coli* using the heat shock method described in Example 2. The transformed *E. coli* were expanded in broth containing ampicillin to select for the vector and collect large amounts of vector.

Example 6

Human vector properties were tested in HEK293 cells (American Type Culture Collection, Manassas, Va.), grown at 37° C. 5% $CO_2$ in DMEM with 10% FBS and 1% Pen/Strep and subcultured at 80% confluence.

The vector (2 μg/well in a 6-well plate) was transfected into the cells using PEI transfection method. The cells were subcultured at $0.5 \times 10^6$ cells per well in a 6-well plate with DMEM medium two days before the transfection. Medium was replaced the night before transfection. Endotoxin-free $dH_2O$ was heated to at around 80° C., and polyethylenimine (Sigma-Aldrich Co. LLC, St. Louis, Mo.) dissolved. The solution was allowed to cool to around 25° C., and the solution neutralized using sodium hydroxide. AAV4-STUb vector or negative control (medium only) was added to serum-free DMEM at 2 μg to every 200 μl for each well transfected, and 9 μl of 1 μg/μl polyethylenimine added to the mix for each well. The transfection mix was incubated at room temperature for 15 minutes, then then added to each well of cells at 210 μl per well and incubated for 48 hours. Cells and media were harvested by scraping the cells from the plates. The medium and cells were then centrifuged at 5000×g for 5 minutes.

For Western blotting of the extracts, cell pellets were resuspended in 50 μL of hypo-osmotic buffer and the cells lysed by three repeated freeze/thaws. 15 μL of lysate was heated with Lamelli sample buffer and run on a BioRad 4-20% acrylamide gel. Transferred to nitrocellulose membrane using a TransBlot. The blot was blocked with 5% milk and protein detected using an anti-E6AP antibody.

Figure 22:
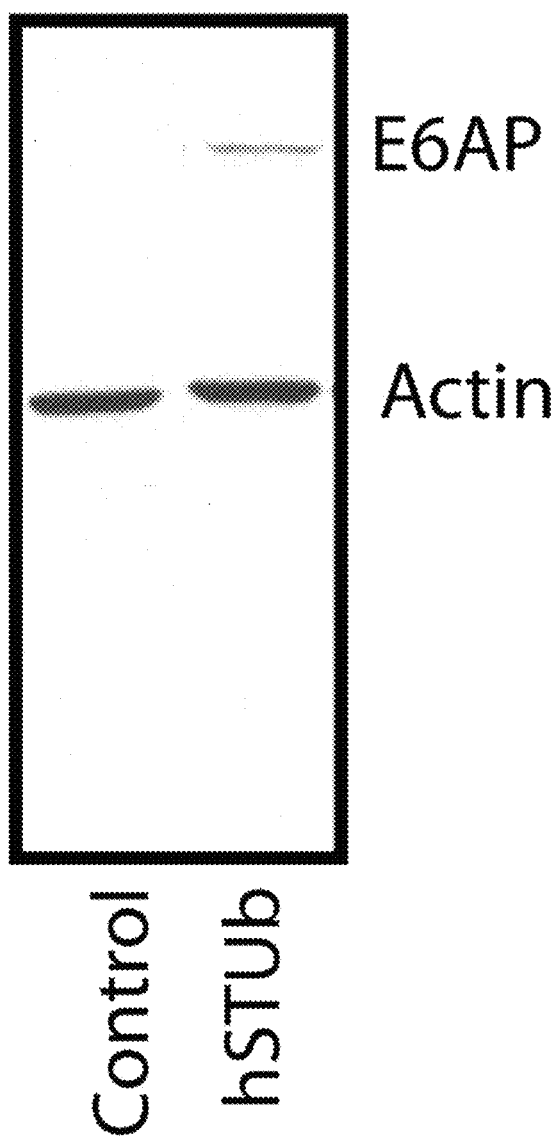
FIG. 22 is a Western blot of HEK293 cell lysate transfected with hSTUb construct. The proteins were stained with anti-E6AP.
Figure 23:
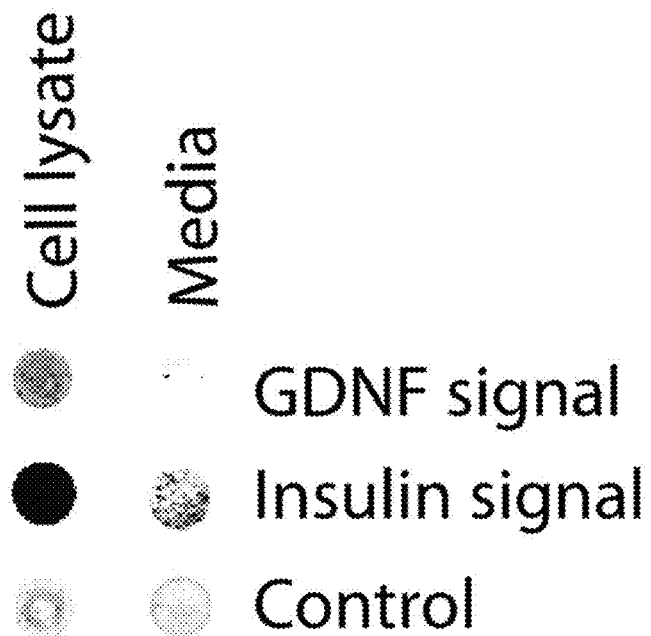
FIG. 23 is a dot blot with Anti-E6AP of HEK293 cells transfected with hSTUb construct with GDNF signal or insulin signal, shows insulin signal works better for expression and secretion.
Figure 24:
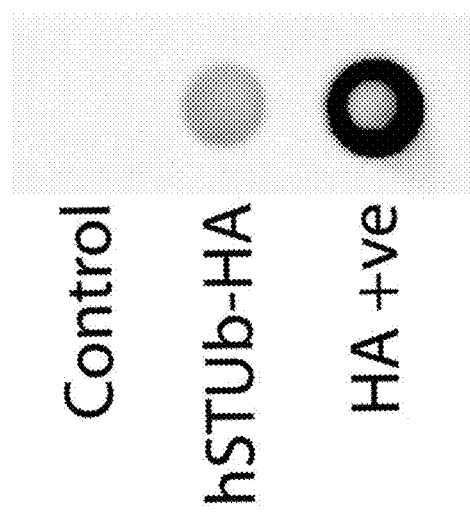
FIG. 24 is a dot blot confirming insulin signal secretion using anti-HA tag antibody.

As seen in FIG. 22, cells transfected with the construct express the UBE3A gene, i.e. E6-AP. Furthermore, appending the gene to the various secretion signals exhibited mixed results, based on the secretion signal peptide. For example, transfection using constructs based on the GDNF secretion signal exhibited less expression and no detectable secretion from the transfected cells, as seen in FIG. 23. Use of the insulin secretion signal resulted in moderate secretion of E6AP from transfected cells, along with high expression of the construct within the cell. The results of insulin-signal secretion were confirmed using an HA-tagged construct, as seen in FIG. 24.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a method of treating UBE3A deficiencies, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

SEQUENCE LISTING

```
<160> NUMBER OF SEQ ID NOS: 15

<210> SEQ ID NO 1
<211> LENGTH: 2550
<212> TYPE: DNA
<213> ORGANISM: Mus musculus

<400> SEQUENCE: 1
atgaagcgag cagctgcaaa gcatctaata gaacgctact accatcagtt aactgagggc      60
tgtggaaatg aggcctgcac gaatgagttt tgtgcttcct gtccaacttt tcttcgtatg     120
gataacaatg cagcagctat taaagcccct gagctttata aaattaatgc aaaactctgt     180
gatcctcatc cctccaagaa aggagcaagc tcagcttacc ttgagaactc aaaaggtgca     240
tctaacaact cagagataaa aatgaacaag aaggaaggaa aagattttaa agatgtgatt     300
tacctaactg aagagaaagt atatgaaatt tatgaatttt gtagagagag tgaggattat     360 tccccttta ttcgtgtaat tggaagaata tttctagtg ctgaggcact ggttctgagc     420
tttcggaaag tcaaacagca cacaaaggag gaattgaaat ctcttcaaga aaaggatgaa     480
gacaaggatg aagatgaaaa ggaaaaagct gcatgttctg ctgctgctat ggaagaagac    540
```

-continued

```
tcagaagcat cttcttcaag gatgggtgat agttcacagg gagacaacaa tgtacaaaaa      600
ttaggtcctg atgatgtgac tgtggatatt gatgctatta gaagggtcta cagcagtttg      660
ctcgctaatg aaaaattaga aactgccttc ctgaatgcac ttgtatatct gtcacctaac      720
gtggaatgtg atttgacata tcataatgtg tatactcgag atcctaatta tctcaatttg      780
ttcattattg taatggagaa tagtaatctc cacagtcctg aatatctgga aatggcgttg      840
ccattatttt gcaaagctat gtgtaagcta ccccttgaag ctcaaggaaa actgattagg      900
ctgtggtcta aatacagtgc tgaccagatt cggagaatga tggaaacatt tcagcaactt      960
attacctaca aagtcataag caatgaattt aatagccgaa atctagtgaa tgatgatgat     1020
gccattgttg ctgcttcaaa gtgtttgaaa atggtttact atgcaaatgt agtgggaggg     1080
gatgtggaca caaatcataa tgaggaagat gatgaagaac ccatacctga gtccagcgaa     1140
ttaacacttc aggagcttct gggagatgaa agaagaaata agaaaggtcc tcgagtggat     1200
ccactagaaa ccgaacttgg cgttaaaact ctagactgtc gaaaaccact tatctccttt     1260
gaagaattca ttaatgaacc actgaatgat gttctagaaa tggacaaaga ttatacctta     1320
ttcaaagttg aaacagagaa caaattctct tttatgacat gtccctttat attgaatgct     1380
gtcacaaaga atctgggatt atattatgac aatagaattc gcatgtacag tgaaagaaga     1440
atcactgttc tttacagcct agttcaagga cagcagttga atccgtattt gagactcaaa     1500
gtcagacgtg accatattat agatgatgca ctggtccggc tagagatgat tgctatggaa     1560
aatcctgcag acttgaagaa gcagttgtat gtggaatttg aaggagaaca aggagtaatg     1620
agggaggcgt ttccaaagag ttttttcagt tgggttgtgg aggaaatttt taatccaaat     1680
attggtatgt tcacatatga tgaagctacg aaattatttt ggtttaatcc atcttctttt     1740
gaaactgagg gtcaggttta ctctgattgg catatcctgg gtctggctat ttacaataat     1800
tgtatactgg atgtccattt tcccatggtt gtatacagga agctaatggg gaaaaaagga     1860
acctttcgtg acttgggaga ctctcaccca gttttatatc agagtttaaa ggatttattg     1920
gaatatgaag ggagtgtgga agatgatatg atgatcactt tccagatatc acagacagat     1980 cttttttggta acccaatgat gtatgatcta aaagaaaatg gtgataaaat tccaattaca     2040
aatgaaaaca ggaaggaatt tgtcaatctc tattcagact acattctcaa taaatctgta     2100
gaaaaacaat tcaaggcatt tcgcagaggt tttcatatgg tgactaatga atcgcccttta    2160 aaatacttat tcagaccaga agaaattgaa ttgcttatat gtggaagccg gaatctagat     2220
ttccaggcac tagaagaaac tacagagtat gacggtggct atacgaggga atctgttgtg     2280
attagggagt tctgggaaat tgttcattcg tttacagatg aacagaaaag actctttctg     2340
cagtttacaa caggcacaga cagagcacct gttggaggac taggaaaatt gaagatgatt     2400
atagccaaaa atggcccaga cacagaaagg ttacctacat ctcatacttg ctttaatgtc     2460
cttttacttc cggaatattc aagcaaagaa aaacttaaag agagattgtt gaaggccatc     2520
acatatgcca aaggatttgg catgctgtaa                                      2550
```

<210> SEQ ID NO 2
<211> LENGTH: 78
<212> TYPE: DNA
<213> ORGANISM: Mus musculus

<400> SEQUENCE: 2

```
atggccctgt tggtgcactt cctaccccctg ctggccctgc ttgccctctg ggagcccaaa      60
cccacccagg ctttttgtc                                                   78
```

```
<210> SEQ ID NO 3
<211> LENGTH: 26
<212> TYPE: PRT
<213> ORGANISM: Mus musculus

<400> SEQUENCE: 3

Met Ala Leu Leu Val His Phe Leu Pro Leu Leu Ala Leu Leu Ala Leu
1               5                   10                  15

Trp Glu Pro Lys Pro Thr Gln Ala Phe Val
            20                  25

<210> SEQ ID NO 4
<211> LENGTH: 33
<212> TYPE: DNA
<213> ORGANISM: Human immunodefiency virus

<400> SEQUENCE: 4
tacggcagaa agaagaggag gcagagaagg aga                                33

<210> SEQ ID NO 5
<211> LENGTH: 11
<212> TYPE: PRT
<213> ORGANISM: Human immunodeficiency virus

<400> SEQUENCE: 5

Tyr Gly Arg Lys Lys Arg Arg Gln Arg Arg Arg
1               5                   10

<210> SEQ ID NO 6
<211> LENGTH: 10893
<212> TYPE: DNA
<213> ORGANISM: Homo sapiens
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (1145)..(1145)
<223> OTHER INFORMATION: n is a, c, g, or t
<220> FEATURE:
<221> NAME/KEY: misc_feature
<222> LOCATION: (1180)..(1180)
<223> OTHER INFORMATION: n is a, c, g, or t
<220> FEATURE:
<221> NAME/KEY: misc_feature
<222> LOCATION: (1257)..(1257)
<223> OTHER INFORMATION: n is a, c, g, or t
<220> FEATURE:
<221> NAME/KEY: misc_feature
<222> LOCATION: (5410)..(5410)
<223> OTHER INFORMATION: n is a, c, g, or t
<220> FEATURE:
<221> NAME/KEY: misc_feature
<222> LOCATION: (7624)..(7624)
<223> OTHER INFORMATION: n is a, c, g, or t
<220> FEATURE:
<221> NAME/KEY: misc_feature
<222> LOCATION: (7644)..(7644)
<223> OTHER INFORMATION: n is a, c, g, or t
<220> FEATURE:
<221> NAME/KEY: misc_feature
<222> LOCATION: (7647)..(7647)
<223> OTHER INFORMATION: n is a, c, g, or t
<220> FEATURE:
<221> NAME/KEY: misc_feature
```

<222> LOCATION: (7741)..(7741)
<223> OTHER INFORMATION: n is a, c, g, or t
<220> FEATURE:
<221> NAME/KEY: misc_feature
<222> LOCATION: (7836)..(7836)
<223> OTHER INFORMATION: n is a, c, g, or t

<400> SEQUENCE: 6

```
ggagtagttt actgagccac taatctaaag tttaatactg tgagtgaata ccagtgagta      60
cctttgttaa tgtggataac caatacttgg ctataggaag ttttttagtt gtgtgtttta     120
tnacacgtat ttgactttgt gaataattat ggcttataat ggcttgtctg ttggtatcta     180
tgtatagcgt ttacagtttc ctttaaaaaa catgcattga gttttttaat agtccaaccc     240
ttaaaataaa tgtgttgtat ggccacctga tctgaccact ttctttcatg ttgacatctt     300
taattttaaa actgttttat ttagtgctta aatcttgttn acaaaattgt cttcctaagt     360
aatatgtcta cctttttttt tggaatatgg aatattttgc taactgtttc tcaattgcat     420
tttacagatc aggagaacct cagtctgacg acattgaagc tagccgaatg taagtgtaac     480
ttggttgaga ctgtggttct tattttgagt tgccctagac tgctttaaat tacgtcacat     540
tatttggaaa taatttctgg ttaaaagaaa ggaatcattt agcagtaaat gggagatagg     600
aacataccta cttttttttcc tatcagataa ctctaaacct cggtaacagt ttactaggtt     660
tctactacta gatagataaa tgcacacgcc taaattctta gtcttttttgc ttccctggta     720
gcagttgtag ggaaataggg aggttgagga aagagtttaa cagtctcaac gcctaccata     780
tttaaggcat caagtactat gttatagata cagagatgcg taataattag ttttcaccct     840
acagaaattt atattatact caagagtgaa agatgcagaa gcaaataatt tcagtcactg     900
aggtagaatg gtatccaaaa tacaatagta acatgaagga gtactggagt accaggtatg     960
caataggaat ctagtgtaga tggcagggaa gtaagagtgg ccaggaaatg ctaagttcag    1020
tcttgaaatg tgactgggaa tcaggcagct atcaactata agtcaaatgt ttacaagctg    1080
ttaaaaatga aatactgatt atgtaaaaga aaaccggatt gatgctttaa atagactcat    1140
tttcntaatg ctaattttta aaatgataga atcctacaan tcttagctgt aaaccttgtg    1200
attttttcagc tgttgtacta aacaacttaa gcacatatac catcagacaa gcccccntcc    1260
cccctttttaa accaaaggaa tgtatactct gttaatacag tcagtaagca ttgacattct    1320
ttatcataat atcctagaaa atatttatta actatttcac tagtcaggag ttgtggtaaa    1380
tagtgcatct ccattttcta cttctcatct tcatacacag gttaatcact tcagtgcttg    1440
actaactttt gccttgatga tatgttgagc tttgtacttg agagctgtac taatcactgt    1500
gcttattgtt tgaatgtttg gtacaggaag cgagcagctg caaagcatct aatagaacgc    1560
tactaccacc agttaactga gggctgtgga aatgaagcct gcacgaatga gttttgtgct    1620
tcctgtccaa cttttcttcg tatggataat aatgcagcag ctattaaagc cctcgagctt    1680
tataagatta atgcaaaact ctgtgatcct catccctcca agaaaggagc aagctcagct    1740
taccttgaga actcgaaagg tgcccccaac aactcctgct ctgagataaa aatgaacaag    1800
aaaggcgcta gaattgattt taaagtaagg atgttttatt ttcaattgag aattgttgcc    1860
tgaaaaccat gtgggagatt taaatgtatt agttttatt tgtttttttct tctgtgacat    1920
aaagacattt tgatatcgta gaaccaattt tttattgtgg taacggacag gaataataac    1980
tacattttac aggtctaatc attgctaatt agaagcagat catatgccaa aagttcattt    2040
gttaatagat tgatttgaac ttttttaaaat tcttaggaaa aatgtattaa gtggtagtga    2100
```

-continued

```
atctccaaaa ctatttaaga gctgtattat gattaatcag tacatgacat attggttcat      2160
atttataatt aaagctatac attaatagat atcttgatta taaagaaagt ttaaactcat      2220
gatcttatta agagttatac attgttgaaa gaatgtaaaa gcatgggtga ggtcattggt      2280
ataggtaggt agttcattga aaaaaatagg taagcattaa attttgtttg ctgaatctaa      2340
gtattagata ctttaagagt tgtatatcat aaatgatatt gagcctagaa tgtttggctg      2400
ttttactttt agaacttttt gcaacagagt aaacatacat attatgaaaa taaatgttct      2460
cttttttcct ctgattttct agatgtgact tacttaacag aagagaaggt atatgaaatt      2520
cttgaattat gtagagaaag agaggattat tcccctttaa tccgtgttat tggaagagtt      2580
ttttctagtg ctgaggcatt ggtacagagc ttccggaaag ttaaacaaca caccaaggaa      2640
gaactgaaat ctcttcaagc aaaagatgaa gacaaagatg aagatgaaaa ggaaaaagct      2700
gcatgttctg ctgctgctat ggaagaagac tcagaagcat cttcctcaag gataggtgat      2760
agctcacagg gagacaacaa tttgcaaaaa ttaggccctg atgatgtgtc tgtggatatt      2820
gatgccatta gaagggtcta caccagattg ctctctaatg aaaaaattga aactgccttt      2880
ctcaatgcac ttgtatattt gtcacctaac gtggaatgtg acttgacgta tcacaatgta      2940
tactctcgag atcctaatta tctgaatttg ttcattatcg taatggagaa tagaaatctc      3000
cacagtcctg aatatctgga aatggctttg ccattatttt gcaaagcgat gagcaagcta      3060 cccettgcag cccaaggaaa actgatcaga ctgtggtcta aatacaatgc agaccagatt      3120
cggagaatga tggagacatt tcagcaactt attacttata aagtcataag caatgaattt      3180
aacagtcgaa atctagtgaa tgatgatgat gccattgttg ctgcttcgaa gtgcttgaaa      3240
atggtttact atgcaaatgt agtgggaggg gaagtggaca caaatcacaa tgaagaagat      3300
gatgaagagc ccatccctga gtccagcgag ctgacacttc aggaacttttt gggagaagaa      3360 agaagaaaca agaaaggtcc tcgagtggac cccctggaaa ctgaacttgg tgttaaaacc      3420
ctggattgtc gaaaaccact tatccctttt gaagagttta ttaatgaacc actgaatgag      3480
gttctagaaa tggataaaga ttatactttt ttcaaagtag aaacagagaa caaattctct      3540
tttatgacat gtcccttat attgaatgct gtcacaaaga attgggatt atattatgac      3600 aatagaattc gcatgtacag tgaacgaaga atcactgttc tctacagctt agttcaagga      3660
cagcagttga atccatattt gagactcaaa gttagacgtg accatatcat agatgatgca      3720
cttgtccggg taagttgggc tgctagatta aaaacctaat aatggggata tcatgataca      3780
gttcagtgaa ttcattttaa aagtgactga aaaaaatgat accatatagc ataggaacac      3840
atggacattt ctgatcttat ataagtatta acttttgtt gttcctgtgc aagtttatag      3900
atgtgttcta caaagtatcg gttgtattat ataatggtca tgctatcttt gaaaaagaat      3960
gggttttcta aatcttgaaa actaaatcca aagtttcttt cattcagaag agaatagagt      4020
gttggacaaa gaccgaaaca agagaaatgt ggagataccc aataataagt gtggatgtgc      4080
agtcttgaac tgggagtaat ggtacagtaa aaccatacca taaaattata ggtagtgtcc      4140
aaaaaattcc atcgtgtaaa attcagagtt gcattattgt ggacttgaag aagcagttgt      4200
atgtgggacg gtatcgataa gcttgatatc gaattcctgc agcccggggg atccactagt      4260
gtggtaatta atactaagtc ttactgtgag agaccataaa ctgctttagt attcagtgta      4320
tttttcttaa ttgaaatatt taacttatga cttagtagat actaagactt aacccttgag      4380
tttctattct aataaggac tactaatgaa caattttgag gttagacctc tactccattg      4440
tttttgctga aatgatttag ctgcttttcc atgtcctgtg tagtccagac ttaacacaca      4500
```

```
agtaataaaa tcttaattaa ttgtatgtta atttcataac aaatcagtaa agttagcttt     4560
ttactatgct agtgtctgtt ttgtgtctgt cttttttgatt atctttaaga ctgaatcttt    4620
gtcttcactg gctttttatc agtttgcttt ctgtttccat ttacatacaa aaagtcaaaa     4680
atttgtattt gtttcctaat cctactcctt gttttttattt tgttttttttc ctgatactag  4740 caatcatctt cttttcatgt ttatcttttc aatcactagc tagagatgat cgctatggaa    4800
aatcctgcag acttgaagaa gcagttgtat gtggaatttg aaggagaaca aggagttgat    4860
gagggaggtg tttccaaaga attttttcag ctggttgtgg aggaaatctt caatccagat    4920
attggtaaat acattagtaa tgtgattatg gtgtcgtatc atcttttgag ttagttattt    4980
gtttatctta ctttgtaaat attttcagct atgaagagca gcaaagaag gatttggtat     5040 ggattaccca gaatcacaca tcatgactga atttgtaggt tttaggaact gatttgtatc    5100
actaatttat tcaaattctt ttatttctta aaggaatat tctaatgaag gaaattatct     5160
ctttggtaaa ctgaattgaa agcactttag aatggtatat tggaacagtt ggagggattt    5220
ctttgctttt tgttgtctaa aaccatcatc aaactcacgg ttttcctgac ctgtgaactt    5280
caaagaacaa tggtttgaag agtattgaga gactgtctca caagtatgtc atgctcaaag    5340
ttcagaaaca ctagctgata tcacattaat taggtttatt tgctataaga tttcttgggg    5400
cttaatatan gtagtgttcc cccaaacttt ttgaactcca gaactctttt ctgccctaac    5460
agtagctact caggagctga ggcaggagaa ttgtttgaac ctaggaggca gaggttgcag    5520
tgagctgaga tcgtgccact ccagcccacc cctgggtaac agagcgagac tccatctcaa    5580 agaaaaaat gaaaaattgt tttcaaaaat agtacgtgtg gtacagatat aagtaattat     5640 attttataa atgaaacact ttggaaatgt agccatttt tgtttttttta tgtttatttt     5700 tcagctatgg gtggataaag catgaatata acttttctta tgtgttagta gaaaattaga    5760
aagcttgaat ttaattaacg tattttctta cccgatgcca ccaaattact tactactttt    5820
ttcctttggc ttcataaaat tacatatcac cattcacccc aatttatagc agatatatgt    5880
ggacattgtt ttctcaagtg ctaatataat agaaatcaat gttgcatgcc taattacata    5940 tatttaaat gttttatatg cataattatt ttaagtttat atttgtatta ttcatcagtc     6000
cttaataaaa tacaaaagta atgtattttt aaaaatcatt tcttataggt atgttcacat    6060
acgatgaatc tacaaaattg ttttggttta atccatcttc ttttgaaact gagggtcagt    6120
ttactctgat tggcatagta ctgggtctgg ctatttacaa taactgtata ctggatgtac    6180
attttcccat ggttgtctac aggaagctaa tggggaaaaa aggaactttt cgtgacttgg    6240
gagactctca cccagtaagt tctttgtcat tttttttaatt cagtctctta gattttattt   6300
aaatgcaaaa atttaattta tgtcaaaatt ttaaagtttt tgtttagaat ctttgttgat    6360
actcttatca ataagataaa aatgttttaa tctgaccgaa gtaccagaaa cacttaaaaa    6420
ctcaaagggg gacattttta tatattgctg tcagcacgaa gctttcgtaa gattgatttc    6480
atagagaagt gtttctaaac attttgtttg tgttttagtg aaatcttaag agataggtaa    6540
aaatcagagt agccctggct aagggtcttg gtagttacaa cgagtgtgcc tgctcctacc    6600 accccccaccc ccaccttgag acaccacaga atttctcata gagcacagtg tgaattctat   6660
tgctaaattg gtggtatggg gtttctcagc agagaatggg acatcacagt gactgacaat    6720 ctttcttttta taggttggaa actatttggg ggactggagg gatactgtct acactttta    6780 caatttttat tgataagatt tttgttgtct tctaagaaga gtgatataaa ttatttgttg    6840
```

```
tattttgtag ttctatggtg gcctcaatttt accatttctg gttgctaggt tctatatcag   6900
agtttaaaag atttattgga gtatgaaggg aatgtggaag atgacatgat gatcactttc   6960
cagatatcac agacagatct ttttggtaac ccaatgatgt atgatctaaa ggaaaatggt   7020
gataaaattc caattacaaa tgaaaacagg aaggtaataa atgttttat gtcacatttt    7080
gtctcttcat taacactttc aaagcatgta tgcttataat ttttaaagaa gtatctaata   7140
tagtctgtac aaaaaaaaaa caagtaacta agtttatgta aatgctagag tccactttc    7200
taaatcttgg atataagttg gtatgaaagc acacagttgg gcactaaagc cccttttaga   7260
gaaagaggac atgaagcagg agatagttaa tagctaagtg tggttgtagt ataaagcaag   7320
aagcagggtg tttcttgtat taagctgtaa gcaggaacct catgattaag gtctttatca   7380
cagaacaaat aaaaattaca tttaatttac acatgtatat cctgtttgtg ataaaaatac   7440
atttctgaaa agtatacttt acgtcagatt tgggttctat tgactaaaat gtgttcatcg   7500
ggaatgggaa taacccagaa cataacaagc aaaaaattat gacaaatata tagtataacct  7560
ttaagaaaca tgtttatatt gatataatt tttgattaaa tattatacac actaagggta    7620
caangcacat tttccttta tganttngat acagtagttt atgtgtcagt cagatacttc    7680
cacatttttg ctgaactgga tacagtaagc agcttaccaa atattctatg gtagaaaact   7740
nggacttcct ggtttgctta aatcaaatat attgtactct cttaaaacgg ttggcatttta   7800
taaatagatg gatacatggt ttaaatgtgt ctgttacat acctagttga gagaacctaa    7860
agaattttct gcgtctccag catttatatt cagttctgtt taatacatta tcgaaattga   7920
catttataag tatgacagtt ttgtgtatat ggccttttca tagcttaata ttggctgtaa   7980
cagagaattg tgaaattgta agaagtagtt ttcttgtag gtgtaaaatt gaattttaa    8040
gaatattctt gacagtttta tgtatatggc cttttcatag cttaatattg gctataacag   8100
agaattgtga aattgttaag aagtaggtgt aaaattgaat ttttaagaat attcttgaat   8160
gtttttttct tggaaaaatt aaaagctat gcagcccaat aacttgtgtt ttgtttgcat    8220
agcatattat aagaagttct tgtgattaat gttttctaca ggaatttgtc aatctttatt   8280
ctgactacat tctcaataaa tcagtagaaa aacagttcaa ggcttttcgg agaggttttc    8340
atatggtgac caatgaatct ccccttaaagt acttattcag accagaagaa attgaattgc   8400
ttatatgtgg aagccgggta agaaagcagg tgtctgcaaa aagtcatgta tcgatttatt   8460
gtttgtaatg atacagtagt atagcagata actaagacat attttcttga atttgcagaa   8520
tctagatttc caagcactag aagaaactac agaatatgac ggtggctata ccagggactc   8580
tgttctgatt aggtgaggta cttagttctt cagaggaaga tttgattcac caagggtg    8640
tgtgatttttg cttcagacct ttatctctag gtactaattc ccaaataagc aaactcacaa   8700
attgtcatct atatacttag atttgtattt gtaatataat caccatttt cagagctaat    8760
cttgtgattt atttcatgaa tgaagtgttg ttatatataa gtctcatgta atctcctgca   8820
tttggcgtat ggattatcta gtattcctca ctggttagag tatgcttact gctgttaga   8880
agataattaa aataaggcta ccatgtctgc aatttttcct ttcttttgaa ctctgcattt    8940
gtgaactgtt acatggcttc ccaggatcaa gcacttttg agtgaaatgg tagtctttta   9000
tttaattctt aagataatat gtccagatac atactagtat ttccattta cacctaaaa    9060
aactaagccc tgaattctca cagaaagatg tagaggttcc cagttctatc tgcttttaaa   9120
caaatgccct tactactcta ctgtctactt ctgtgtacta catcatcgta tgtagttgtt   9180
tgcatttggg ccagttggtt ggggcagggg tcttttttttc ttttgtccct taatctgtat   9240
```

-continued

```
cacttttttcc tcccaaagtt gagttaaagg atgagtagac caggagaata aaggagaaag    9300
gataaataaa atatataccc aaaggcacct ggagttaatt tttccaaata ttcatttcag    9360
tcttttttcaa ttcataggat tttgtctttt gctcattact gactgcataa tgtgattata    9420
ccatagttta aatagtcact tcctgttact acacacttgg gttttctcaa ttttttacta    9480
ttgtagtact aatattttac tatattgtaa tctaatccaa attttttacgt attcagagct    9540
gttcaggata aatttgcttg gaaattttta aatcaccaga agtgatacta tcctgataat    9600
taacttccaa gttgtctctt aatatagttt taatgcaaat cataagctta tgttagtacc    9660
agtcataatg aatgccaaac tgaaaccagt attgtatttt ttctcattag ggagttctgg    9720
gaaatcgttc attcatttac agatgaacag aaaagactct tcttgcagtt tacaacgggc    9780
acagacagag cacctgtggg aggactagga aaattaaaga tgattatagc caaaaatggc    9840
ccagacacag aaaggtaggt aattattaac ttgtgactgt atacctaccg aaaaccttgc    9900
attcctcgtc acatacatat gaactgtctt tatagtttct gagcacattc gtgattttat    9960
atacaaatcc ccaaatcata ttagacaatt gagaaaatac tttgctgtca ttgtgtgagg   10020
aaacttttaa gaaattgccc tagttaaaaa ttattatggg gctcacattg gtttggaatc   10080
aaattagtgt gattcattta ctttttttgat tcccagcttg ttaattgaaa gccatataac   10140
atgatcatct atttagaatg gttacattga ggctcggaag attatcattt gattgtgcta   10200
gaatcctgtt atcaaatcat tttcttagtc atattgccag cagtgtttct aataagcatt   10260
taagagcaca cactttgcag tcttgtaaaa caggttttgag tattttctcc accttagagg   10320
aagttacttg acttctcagt gacctaacct ctaaagtgca tttactgatg tcctctctgt   10380
ggttttgttg tggaaagatt tagttaaatg aactgtaaga attcagtacc taaaatggta   10440
tctgttatgt agtaaaaact caatggatac agtatcttat catcgtcact agctttgagt   10500
aatttatagg ataaaggcaa cttggtagtt acacaacaaa aagttatga tttgcattaa   10560
tgtatagttt gcattgcaga ccgtctcaac tatatacaat ctaaaaatag gagcatttaa   10620
ttctaagtgt atttcccatg acttacagtt ttcctgtttt tttcccctttt tctctattta   10680
ggttacctac atctcatact tgctttaatg tgcttttact tccggaatac tcaagcaaag   10740
aaaaacttaa agagagattg ttgaaggcca tcacgtatgc caaaggatttt ggcatgctgt   10800
aaaacaaaac aaaacaaaat aaaacaaaaa aaaggaagga aaaaaaaga aaaaatttaa   10860
aaaattttaa aaatataacg agggataaat ttt                                10893
```

<210> SEQ ID NO 7
<211> LENGTH: 852
<212> TYPE: PRT
<213> ORGANISM: Homo sapiens

<400> SEQUENCE: 7

```
Met Lys Arg Ala Ala Ala Lys His Leu Ile Glu Arg Tyr Tyr His Gln
1               5                   10                  15

Leu Thr Glu Gly Cys Gly Asn Glu Ala Cys Thr Asn Glu Phe Cys Ala
            20                  25                  30

Ser Cys Pro Thr Phe Leu Arg Met Asp Asn Asn Ala Ala Ala Ile Lys
        35                  40                  45

Ala Leu Glu Leu Tyr Lys Ile Asn Ala Lys Leu Cys Asp Pro His Pro
    50                  55                  60

Ser Lys Lys Gly Ala Ser Ser Ala Tyr Leu Glu Asn Ser Lys Gly Ala
65                  70                  75                  80
```

```
Pro Asn Asn Ser Cys Ser Glu Ile Lys Met Asn Lys Gly Ala Arg
                85                  90                  95

Ile Asp Phe Lys Asp Val Thr Tyr Leu Thr Glu Lys Val Tyr Glu
            100                 105                 110

Ile Leu Glu Leu Cys Arg Glu Arg Glu Asp Tyr Ser Pro Leu Ile Arg
        115                 120                 125

Val Ile Gly Arg Val Phe Ser Ser Ala Glu Ala Leu Val Gln Ser Phe
    130                 135                 140

Arg Lys Val Lys Gln His Thr Lys Glu Glu Leu Lys Ser Leu Gln Ala
145                 150                 155                 160

Lys Asp Glu Asp Lys Asp Glu Asp Lys Lys Ala Ala Cys Ser
                165                 170                 175

Ala Ala Ala Met Glu Glu Asp Ser Glu Ala Ser Ser Ser Arg Ile Gly
            180                 185                 190

Asp Ser Ser Gln Gly Asp Asn Asn Leu Gln Lys Leu Gly Pro Asp Asp
        195                 200                 205

Val Ser Val Asp Ile Asp Ala Ile Arg Arg Val Tyr Thr Arg Leu Leu
    210                 215                 220

Ser Asn Glu Lys Ile Glu Thr Ala Phe Leu Asn Ala Leu Val Tyr Leu
225                 230                 235                 240

Ser Pro Asn Val Glu Cys Asp Leu Thr Tyr His Asn Val Tyr Ser Arg
            245                 250                 255

Asp Pro Asn Tyr Leu Asn Leu Phe Ile Ile Val Met Glu Asn Arg Asn
        260                 265                 270

Leu His Ser Pro Glu Tyr Leu Glu Met Ala Leu Pro Leu Phe Cys Lys
    275                 280                 285

Ala Met Ser Lys Leu Pro Leu Ala Ala Gln Gly Lys Leu Ile Arg Leu
290                 295                 300

Trp Ser Lys Tyr Asn Ala Asp Gln Ile Arg Arg Met Met Glu Thr Phe
305                 310                 315                 320

Gln Gln Leu Ile Thr Tyr Lys Val Ile Ser Asn Glu Phe Asn Ser Arg
            325                 330                 335

Asn Leu Val Asn Asp Asp Ala Ile Val Ala Ala Ser Lys Cys Leu
        340                 345                 350

Lys Met Val Tyr Tyr Ala Asn Val Val Gly Gly Glu Val Asp Thr Asn
    355                 360                 365

His Asn Glu Glu Asp Asp Glu Glu Pro Ile Pro Glu Ser Ser Glu Leu
    370                 375                 380

Thr Leu Gln Glu Leu Leu Gly Glu Glu Arg Arg Asn Lys Lys Gly Pro
385                 390                 395                 400

Arg Val Asp Pro Leu Glu Thr Glu Leu Gly Val Lys Thr Leu Asp Cys
            405                 410                 415

Arg Lys Pro Leu Ile Pro Phe Glu Glu Phe Ile Asn Glu Pro Leu Asn
        420                 425                 430

Glu Val Leu Glu Met Asp Lys Asp Tyr Thr Phe Phe Lys Val Glu Thr
    435                 440                 445

Glu Asn Lys Phe Ser Phe Met Thr Cys Pro Phe Ile Leu Asn Ala Val
    450                 455                 460

Thr Lys Asn Leu Gly Leu Tyr Tyr Asp Asn Arg Ile Arg Met Tyr Ser
465                 470                 475                 480

Glu Arg Arg Ile Thr Val Leu Tyr Ser Leu Val Gln Gly Gln Gln Leu
            485                 490                 495
```

```
Asn Pro Tyr Leu Arg Leu Lys Val Arg Asp His Ile Ile Asp Asp
                500                 505                 510

Ala Leu Val Arg Leu Glu Met Ile Ala Met Glu Asn Pro Ala Asp Leu
            515                 520                 525

Lys Lys Gln Leu Tyr Val Glu Phe Glu Gly Glu Gln Gly Val Asp Glu
        530                 535                 540

Gly Gly Val Ser Lys Glu Phe Phe Gln Leu Val Val Glu Glu Ile Phe
545                 550                 555                 560

Asn Pro Asp Ile Gly Met Phe Thr Tyr Asp Gly Ser Thr Lys Leu Phe
                565                 570                 575

Trp Phe Asn Pro Ser Ser Phe Glu Thr Glu Gly Gln Phe Thr Leu Ile
            580                 585                 590

Gly Ile Val Leu Gly Leu Ala Ile Tyr Asn Asn Cys Ile Leu Asp Val
        595                 600                 605

His Phe Pro Met Val Val Tyr Arg Lys Leu Met Gly Lys Lys Gly Thr
610                 615                 620

Phe Arg Asp Leu Gly Asp Ser His Pro Val Leu Tyr Gln Ser Leu Lys
625                 630                 635                 640

Asp Leu Leu Glu Tyr Glu Gly Asn Val Glu Asp Asp Met Met Ile Thr
                645                 650                 655

Phe Gln Ile Ser Gln Thr Asp Leu Phe Gly Asn Pro Met Met Tyr Asp
            660                 665                 670

Leu Lys Glu Asn Gly Asp Lys Ile Pro Ile Thr Asn Glu Asn Arg Lys
        675                 680                 685

Glu Phe Val Asn Leu Tyr Ser Asp Tyr Ile Leu Asn Lys Ser Val Glu
690                 695                 700

Lys Gln Phe Lys Ala Phe Arg Arg Gly Phe His Met Val Thr Asn Glu
705                 710                 715                 720

Ser Pro Leu Lys Tyr Leu Phe Arg Pro Glu Glu Ile Glu Leu Leu Ile
                725                 730                 735

Cys Gly Ser Arg Asn Leu Asp Phe Gln Ala Leu Glu Glu Thr Thr Glu
            740                 745                 750

Tyr Asp Gly Gly Tyr Thr Arg Asp Ser Val Leu Ile Arg Glu Phe Trp
        755                 760                 765

Glu Ile Val His Ser Phe Thr Asp Glu Gln Lys Arg Leu Phe Leu Gln
770                 775                 780

Phe Thr Thr Gly Thr Asp Arg Ala Pro Val Gly Gly Leu Gly Lys Leu
785                 790                 795                 800

Lys Met Ile Ile Ala Lys Asn Gly Pro Asp Thr Glu Arg Leu Pro Thr
                805                 810                 815

Ser His Thr Cys Phe Asn Val Leu Leu Leu Pro Glu Tyr Ser Ser Lys
            820                 825                 830

Glu Lys Leu Lys Glu Arg Leu Leu Lys Ala Ile Thr Tyr Ala Lys Gly
        835                 840                 845

Phe Gly Met Leu
    850

<210> SEQ ID NO 8
<211> LENGTH: 57
<212> TYPE: DNA
<213> ORGANISM: Homo sapiens

<400> SEQUENCE: 8
atgaagttat gggatgtcgt ggctgtctgc ctggtgctgc tccacaccgc gtccgcc        57
```

<210> SEQ ID NO 9
<211> LENGTH: 72
<212> TYPE: DNA
<213> ORGANISM: Homo sapiens

<400> SEQUENCE: 9

```
atggccctgt ggatgcgcct cctgcccctg ctggcgctgc tggccctctg gggacctgac      60
ccagccgcag cc                                                         72
```

<210> SEQ ID NO 10
<211> LENGTH: 60
<212> TYPE: DNA
<213> ORGANISM: Homo sapiens

<400> SEQUENCE: 10

```
atggagacag acacactcct gctatgggta ctgctgctct gggttccagg ttccactggt      60
```

<210> SEQ ID NO 11
<211> LENGTH: 11
<212> TYPE: PRT
<213> ORGANISM: Human Immunodeficiency Virus

<400> SEQUENCE: 11

Tyr Ala Arg Lys Ala Ala Arg Gln Ala Arg Ala
1               5                   10

<210> SEQ ID NO 12
<211> LENGTH: 2767
<212> TYPE: DNA
<213> ORGANISM: Homo sapiens

<400> SEQUENCE: 12

```
acagtatgac atctgatgct ggagggtcgc acttcacaa atgagtcagc tggtacatgg      60
ggttatcatc aattttttagc tcttctgtct gggagataca agtttggaag caatcttggg     120
gtacttaccc acaaggctgg tggagaccag atcaggagaa cctcagtctg acgacattga     180
agctagccga atgaagcgag cagctgcaaa gcatctaata gaacgctact accaccagtt     240
aactgagggc tgtggaaatg aagcctgcac gaatgagttt tgtgcttcct gtccaacttt     300
tcttcgtatg ataataatg cagcagctat aaagccctc gagctttata agattaatgc      360
aaaactctgt gatcctcatc cctccaagaa aggagcaagc tcagcttacc ttgagaactc     420
gaaaggtgcc cccaacaact cctgctctga gataaaaatg aacaagaaag gcgctagaat     480
tgattttaaa gatgtgactt acttaacaga agagaaggta tatgaaattc ttgaattatg     540
tagagaaaga gaggattatt cccctttaat ccgtgttatt ggaagagttt tttctagtgc     600
tgaggcattg gtacagagct tccggaaagt taaacaacac accaaggaag aactgaaatc     660
tcttcaagca aagatgaag acaaagatga ggatgaaaag gaaaaagctg catgttctgc     720
tgctgctatg gaagaagact cagaagcatc ttcctcaagg ataggtgata gctcacaggg     780
agacaacaat ttgcaaaaat taggccctga tgatgtgtct gtggatattg atgccattag     840
aagggtctac accagattgc tctctaatga aaaaattgaa actgcctttc tcaatgcact     900
tgtatatttg tcacctaacg tggaatgtga cttgacgtat cacaatgtat actctcgaga     960
tcctaattat ctgaatttgt tcattatcgt aatggagaat agaaatctcc acagtcctga    1020
atatctggaa atggctttgc cattattttg caaagcgatg agcaagctac ccctttgcagc    1080 ccaaggaaaa ctgatcagac tgtggtctaa atacaatgca gaccagattc ggagaatgat    1140
```

```
ggagacattt cagcaactta ttacttataa agtcataagc aatgaattta acagtcgaaa    1200
tctagtgaat gatgatgatg ccattgttgc tgcttcgaag tgcttgaaaa tggtttacta    1260
tgcaaatgta gtgggagggg aagtggacac aaatcacaat gaagaagatg atgaagagcc    1320
catccctgag tccagcgagc tgacacttca ggaacttttg ggagaagaaa gaagaaacaa    1380
gaaaggtcct cgagtggacc ccctggaaac tgaacttggt gttaaaaccc tggattgtcg    1440
aaaaccactt atccctttg aagagtttat taatgaacca ctgaatgagg ttctagaaat    1500
ggataaagat tatactttt tcaaagtaga aacagagaac aaattctctt ttatgacatg    1560
tccctttata ttgaatgctg tcacaaagaa tttgggatta ttatatgaca atagaattcg    1620
catgtacagt gaacgaagaa tcactgttct ctacagctta gttcaaggac agcagttgaa    1680
tccatatttg agactcaaag ttagacgtga ccatatcata gatgatgcac ttgtccggct    1740
agagatgatc gctatggaaa atcctgcaga cttgaagaag cagttgtatg tggaatttga    1800
aggagaacaa ggagttgatg agggaggtgt ttccaaagaa ttttttcagc tggttgtgga    1860
ggaaatcttc aatccagata ttggtatgtt cacatacgat gaatctacaa aattgttttg    1920
gtttaatcca tcttcttttg aaactgaggg tcagtttact ctgattggca tagtactggg    1980
tctggctatt tacaataact gtatactgga tgtacatttt cccatggttg tctacaggaa    2040
gctaatgggg aaaaaaggaa cttttcgtga cttgggagac tctcacccag ttctatatca    2100
gagtttaaaa gatttattgg agtatgaagg gaatgtggaa gatgacatga tgatcacttt    2160
ccagatatca cagacagatc ttttttggtaa cccaatgatg tatgatctaa aggaaaatgg    2220
tgataaaatt ccaattacaa atgaaaacag gaaggaattt gtcaatcttt attctgacta    2280
cattctcaat aaatcagtag aaaaacagtt caaggctttt cggagaggtt ttcatatggt    2340
gaccaatgaa tctcccttaa agtacttatt cagaccagaa gaaattgaat tgcttatatg    2400
tggaagccgg aatctagatt tccaagcact agaagaaact acagaatatg acggtggcta    2460
taccagggac tctgttctga ttagggagtt ctggaaaatc gttcattcat ttacagatga    2520
acagaaaaga ctcttcttgc agtttacaac gggcacagac agagcacctg tgggaggact    2580
aggaaaatta aagatgatta tagccaaaaa tggcccagac acagaaaggt tacctacatc    2640
tcatacttgc tttaatgtgc ttttacttcc ggaatactca agcaaagaaa aacttaaaga    2700
gagattgttg aaggccatca cgtatgccaa aggattttgg catgctgtaaa acaaaacaaa    2760 acaaaat                                                              2767

<210> SEQ ID NO 13
<211> LENGTH: 5276
<212> TYPE: DNA
<213> ORGANISM: Homo sapiens

<400> SEQUENCE: 13
agccagtcct cccgtcttgc gccgcggccg cgagatccgt gtgtctccca agatggtggc      60
gctgggctcg gggtgactac aggagacgac ggggccttt cccttcgcca ggacccgaca     120
caccaggctt cgctcgctcg cgcaccccte cgccgcgtag ccatccgcca gcgcgggcgc     180
ccgccatccg ccgcctactt acgcttcacc tctgccgacc cggcgcgctc ggctgcgggc     240
ggcggcgcct ccttcggctc ctcctcggaa tagctcgcgg cctgtagccc ctggcaggag     300 ggccccctcag ccccccggtg tggacaggca gcgcgggctg cgacgaacg ccgggatttc     360 ggcggccccg gcgctccctt tcccggcctc gttttccgga taaggaagcg cgggtcccgc     420
atgagccccg gcggtggcgg cagcgaaaga gaacgaggcg gtggcgggcg gaggcggcgg    480
```

```
gcgagggcga ctacgaccag tgaggcggcc gccgcagccc aggcgcgggg gcgacgacag      540
gttaaaaatc tgtaagagcc tgattttaga attcaccagc tcctcagaag tttggcgaaa      600
tatgagttat taagcctacg ctcagatcaa ggtagcagct agactggtgt gacaacctgt      660
ttttaatcag tgactcaaag ctgtgatcac cctgatgtca ccgaatggcc acagcttgta      720
aaagagagtt acagtggagg taaaaggagt ggcttgcagg atggagaagc tgcaccagtg      780
ttattggaaa tcaggagaac ctcagtctga cgacattgaa gctagccgaa tgaagcgagc      840
agctgcaaag catctaatag aacgctacta ccaccagtta actgagggct gtggaaatga      900
agcctgcacg aatgagtttt gtgcttcctg tccaactttt cttcgtatgg ataataatgc      960
agcagctatt aaagccctcg agctttataa gattaatgca aaactctgtg atcctcatcc     1020
ctccaagaaa ggagcaagct cagcttacct tgagaactcg aaaggtgccc caacaactc     1080 ctgctctgag ataaaaatga caagaaagg cgctagaatt gattttaaag atgtgactta     1140
cttaacagaa gagaaggtat atgaaattct tgaattatgt agagaaagag aggattattc     1200
ccctttaatc cgtgttattg gaagagtttt ttctagtgct gaggcattgg tacagagctt     1260
ccggaaagtt aaacaacaca ccaaggaaga actgaaatct cttcaagcaa agatgaaga     1320 caaagatgaa gatgaaaagg aaaaagctgc atgttctgct gctgctatgg aagaagactc     1380
agaagcatct tcctcaagga taggtgatag ctcacaggga gacaacaatt tgcaaaaatt     1440
aggccctgat gatgtgtctg tggatattga tgccattaga agggtctaca ccagattgct     1500
ctctaatgaa aaaattgaaa ctgcctttct caatgcactt gtatatttgt cacctaacgt     1560
ggaatgtgac ttgacgtatc acaatgtata ctctcgagat cctaattatc tgaatttgtt     1620
cattatcgta atgagaata gaaatctcca cagtcctgaa tatctggaaa tggctttgcc     1680 attatttgc aaagcgatga gcaagctacc ccttgcagcc aaggaaaac tgatcagact     1740 gtggtctaaa tacaatgcag accagattcg gagaatgatg gagacatttc agcaacttat     1800
tacttataaa gtcataagca atgaatttaa cagtcgaaat ctagtgaatg atgatgatgc     1860
cattgttgct gcttcgaagt gcttgaaaat ggtttactat gcaaatgtag tgggagggga     1920
agtggacaca aatcacaatg aagaagatga tgaagagccc atccctgagt ccagcgagct     1980
gacacttcag gaactttttgg gagaagaaag aagaaacaag aaaggtcctc gagtggaccc     2040
cctggaaact gaacttggtg ttaaaaccct ggattgtcga aaaccactta tcccttttga     2100
agagtttatt aatgaaccac tgaatgaggt tctagaaatg gataaagatt atactttttt     2160
caaagtagaa acagagaaca aattctcttt tatgacatgt cccttttatat tgaatgctgt     2220 cacaaagaat ttgggattat attatgacaa tagaattcgc atgtacagtg aacgaagaat     2280
cactgttctc tacagcttag ttcaaggaca gcagttgaat ccatatttga gactcaaagt     2340
tagacgtgac catatcatag atgatgcact tgtccggcta gagatgatcg ctatggaaaa     2400
tcctgcagac ttgaagaagc agttgtatgt ggaatttgaa ggaacaag gagttgatga     2460 gggaggtgtt tccaaagaat tttttcagct ggttgtggag gaaatcttca atccagatat     2520
tggtatgttc acatacgatg aatctacaaa attgttttgg tttaatccat cttcttttga     2580
aactgagggt cagtttactc tgattggcat agtactgggg ctggctattt acaataactg     2640
tatactggat gtacattttc ccatggttgt ctacaggaag ctaatgggga aaaaggaac     2700 ttttcgtgac ttgggagact ctcacccagt tctatatcag agtttaaaag atttattgga     2760
gtatgaaggg aatgtggaag atgacatgat gatcactttc cagatatcac agacagatct     2820
```

```
ttttggtaac ccaatgatgt atgatctaaa ggaaaatggt gataaaattc caattacaaa      2880
tgaaaacagg aaggaatttg tcaatcttta ttctgactac attctcaata aatcagtaga      2940
aaaacagttc aaggcttttc ggagaggttt tcatatggtg accaatgaat ctcccttaaa      3000
gtacttattc agaccagaag aaattgaatt gcttatatgt ggaagccgga atctagattt      3060
ccaagcacta gaagaaacta cagaatatga cggtggctat accagggact ctgttctgat      3120
tagggagttc tgggaaatcg ttcattcatt tacagatgaa cagaaaagac tcttcttgca      3180
gtttacaacg ggcacagaca gagcacctgt gggaggacta ggaaaattaa agatgattat      3240
agccaaaaat ggcccagaca cagaaaggtt acctacatct catacttgct ttaatgtgct      3300
tttacttccg gaatactcaa gcaaagaaaa acttaaagag agattgttga aggccatcac      3360
gtatgccaaa ggatttggca tgctgtaaaa caaaacaaaa caaaataaaa caaaaaaaag      3420
gaaggaaaaa aaagaaaaa atttaaaaaa ttttaaaaat ataacgaggg ataaattttt      3480
ggtggtgata gtgtcccagt acaaaaaggc tgtaagatag tcaaccacag tagtcaccta      3540
tgtctgtgcc tcccttcttt attggggaca tgtgggctgg aacagcagat ttcagctaca      3600
tatatgaaca aatccttat tattattata attatttttt tgcgtgaaag tgttacatat      3660
tctttcactt gtatgtacag agaggttttt ctgaatattt atttttaaggg ttaaatcact      3720 tttgcttgtg tttattactg cttgaggttg agccttttga gtatttaaaa aatatatacc      3780
aacagaacta ctctcccaag gaaaatattg ccaccatttg tagaccacgt aaccttcaag      3840
tatgtgctac ttttttgtcc ctgtatctaa ctcaaatcag gaactgtatt ttttttaatg      3900
atttgctttt gaaacttgaa gtcttgaaaa cagtgtgatg caattactgc tgttctagcc      3960
cccaaagagt tttctgtgca aaatcttgag aatcaatcaa taaagaaaga tggaaggaag      4020
ggagaaattg gaatgtttta actgcagccc tcagaacttt agtaacagca caacaaatta      4080
aaaacaaaaa caactcatgc cacagtatgt cgtcttcatg tgtcttgcaa tgaactgttt      4140
cagtagccaa tcctctttct tagtatatga aaggacaggg attttgttc ttgttgttct      4200 cgttgttgtt ttaagtttac tggggaaagt gcatttggcc aaatgaaatg gtagtcaagc      4260
ctattgcaac aaagttagga agtttgttgt ttgtttatta taaacaaaaa gcatgtgaaa      4320
gtgcacttaa gatagagttt ttattaatta cttacttatt acctagattt taaatagaca      4380
atccaaagtc tccccttcgt gttgccatca tcttgttgaa tcagccattt tatcgaggca      4440
cgtgatcagt gttgcaacat aatgaaaaag atggctactg tgccttgtgt tacttaatca      4500
tacagtaagc tgacctggaa atgaatgaaa ctattactcc taagaattac attgtatagc      4560
cccacagatt aaatttaatt aattaattca aaacatgtta aacgttactt tcatgtacta      4620
tggaaaagta caagtaggtt tacattactg atttccagaa gtaagtagtt tcccctttcc      4680
tagtcttctg tgtatgtgat gttgttaatt tcttttattg cattataaaa taaaaggatt      4740
atgtattttt aactaaggtg agacattgat atatccttt gctacaagct atagctaatg      4800
tgctgagctt gtgccttggt gattgattga ttgattgact gattgtttta actgattact      4860
gtagatcaac ctgatgattt gtttgtttga aattggcagg aaaaatgcag ctttcaaatc      4920
attgggggga gaaaaggat gtctttcagg attattttaa ttaatttttt tcataattga      4980
gacagaactg tttgttatgt accataatgc taaataaaac tgtggcactt tcaccataa      5040 tttaatttag tggaaaaaga agacaatgct ttccatattg tgataaggta acatgggggtt      5100 tttctgggcc agcctttaga acactgttag ggtacatacg ctaccttgat gaagggacc      5160 ttcgtgcaac tgtagtcatc ttaaaggctt ctcatccact gtgcttctta atgtgtaatt      5220
```

```
aaagtgagga gaaattaaat actctgaggg cgttttatat aataaattcg tgaaga        5276
```

<210> SEQ ID NO 14
<211> LENGTH: 875
<212> TYPE: PRT
<213> ORGANISM: Homo sapiens

<400> SEQUENCE: 14

```
Met Glu Lys Leu His Gln Cys Tyr Trp Lys Ser Gly Glu Pro Gln Ser
1               5                   10                  15

Asp Asp Ile Glu Ala Ser Arg Met Lys Arg Ala Ala Lys His Leu
            20                  25                  30

Ile Glu Arg Tyr Tyr His Gln Leu Thr Glu Gly Cys Gly Asn Glu Ala
            35                  40                  45

Cys Thr Asn Glu Phe Cys Ala Ser Cys Pro Thr Phe Leu Arg Met Asp
50                  55                  60

Asn Asn Ala Ala Ala Ile Lys Ala Leu Glu Leu Tyr Lys Ile Asn Ala
65                  70                  75                  80

Lys Leu Cys Asp Pro His Pro Ser Lys Lys Gly Ala Ser Ser Ala Tyr
                85                  90                  95

Leu Glu Asn Ser Lys Gly Ala Pro Asn Asn Ser Cys Ser Glu Ile Lys
            100                 105                 110

Met Asn Lys Lys Gly Ala Arg Ile Asp Phe Lys Asp Val Thr Tyr Leu
            115                 120                 125

Thr Glu Glu Lys Val Tyr Glu Ile Leu Glu Leu Cys Arg Glu Arg Glu
    130                 135                 140

Asp Tyr Ser Pro Leu Ile Arg Val Ile Gly Arg Val Phe Ser Ser Ala
145                 150                 155                 160

Glu Ala Leu Val Gln Ser Phe Arg Lys Val Lys Gln His Thr Lys Glu
                165                 170                 175

Glu Leu Lys Ser Leu Gln Ala Lys Asp Glu Asp Lys Asp Glu Asp Glu
            180                 185                 190

Lys Glu Lys Ala Ala Cys Ser Ala Ala Ala Met Glu Glu Asp Ser Glu
            195                 200                 205

Ala Ser Ser Ser Arg Ile Gly Asp Ser Ser Gln Gly Asp Asn Asn Leu
    210                 215                 220

Gln Lys Leu Gly Pro Asp Asp Val Ser Val Asp Ile Asp Ala Ile Arg
225                 230                 235                 240

Arg Val Tyr Thr Arg Leu Leu Ser Asn Glu Lys Ile Glu Thr Ala Phe
                245                 250                 255

Leu Asn Ala Leu Val Tyr Leu Ser Pro Asn Val Glu Cys Asp Leu Thr
            260                 265                 270

Tyr His Asn Val Tyr Ser Arg Asp Pro Asn Tyr Leu Asn Leu Phe Ile
            275                 280                 285

Ile Val Met Glu Asn Arg Asn Leu His Ser Pro Glu Tyr Leu Glu Met
    290                 295                 300

Ala Leu Pro Leu Phe Cys Lys Ala Met Ser Lys Leu Pro Leu Ala Ala
305                 310                 315                 320

Gln Gly Lys Leu Ile Arg Leu Trp Ser Lys Tyr Asn Ala Asp Gln Ile
                325                 330                 335

Arg Arg Met Met Glu Thr Phe Gln Gln Leu Ile Thr Tyr Lys Val Ile
            340                 345                 350

Ser Asn Glu Phe Asn Ser Arg Asn Leu Val Asn Asp Asp Ala Ile
            355                 360                 365
```

```
Val Ala Ala Ser Lys Cys Leu Lys Met Val Tyr Tyr Ala Asn Val Val
    370                 375                 380
Gly Gly Glu Val Asp Thr Asn His Asn Glu Glu Asp Asp Glu Glu Pro
385                 390                 395                 400
Ile Pro Glu Ser Ser Glu Leu Thr Leu Gln Glu Leu Leu Gly Glu Glu
                405                 410                 415
Arg Arg Asn Lys Lys Gly Pro Arg Val Asp Pro Leu Glu Thr Glu Leu
                420                 425                 430
Gly Val Lys Thr Leu Asp Cys Arg Lys Pro Leu Ile Pro Phe Glu Glu
                435                 440                 445
Phe Ile Asn Glu Pro Leu Asn Glu Val Leu Glu Met Asp Lys Asp Tyr
    450                 455                 460
Thr Phe Phe Lys Val Glu Thr Glu Asn Lys Phe Ser Phe Met Thr Cys
465                 470                 475                 480
Pro Phe Ile Leu Asn Ala Val Thr Lys Asn Leu Gly Leu Tyr Tyr Asp
                485                 490                 495
Asn Arg Ile Arg Met Tyr Ser Glu Arg Arg Ile Thr Val Leu Tyr Ser
                500                 505                 510
Leu Val Gln Gly Gln Gln Leu Asn Pro Tyr Leu Arg Leu Lys Val Arg
    515                 520                 525
Arg Asp His Ile Ile Asp Asp Ala Leu Val Arg Leu Glu Met Ile Ala
    530                 535                 540
Met Glu Asn Pro Ala Asp Leu Lys Lys Gln Leu Tyr Val Glu Phe Glu
545                 550                 555                 560
Gly Glu Gln Gly Val Asp Glu Gly Gly Val Ser Lys Glu Phe Phe Gln
                565                 570                 575
Leu Val Val Glu Glu Ile Phe Asn Pro Asp Ile Gly Met Phe Thr Tyr
                580                 585                 590
Asp Glu Ser Thr Lys Leu Phe Trp Phe Asn Pro Ser Ser Phe Glu Thr
                595                 600                 605
Glu Gly Gln Phe Thr Leu Ile Gly Ile Val Leu Gly Leu Ala Ile Tyr
    610                 615                 620
Asn Asn Cys Ile Leu Asp Val His Phe Pro Met Val Val Tyr Arg Lys
625                 630                 635                 640
Leu Met Gly Lys Lys Gly Thr Phe Arg Asp Leu Gly Asp Ser His Pro
                645                 650                 655
Val Leu Tyr Gln Ser Leu Lys Asp Leu Leu Glu Tyr Glu Gly Asn Val
    660                 665                 670
Glu Asp Asp Met Met Ile Thr Phe Gln Ile Ser Gln Thr Asp Leu Phe
    675                 680                 685
Gly Asn Pro Met Met Tyr Asp Leu Lys Glu Asn Gly Asp Lys Ile Pro
    690                 695                 700
Ile Thr Asn Glu Asn Arg Lys Glu Phe Val Asn Leu Tyr Ser Asp Tyr
705                 710                 715                 720
Ile Leu Asn Lys Ser Val Glu Lys Gln Phe Lys Ala Phe Arg Arg Gly
                725                 730                 735
Phe His Met Val Thr Asn Glu Ser Pro Leu Lys Tyr Leu Phe Arg Pro
                740                 745                 750
Glu Glu Ile Glu Leu Leu Ile Cys Gly Ser Arg Asn Leu Asp Phe Gln
    755                 760                 765
Ala Leu Glu Glu Thr Thr Glu Tyr Asp Gly Gly Tyr Thr Arg Asp Ser
    770                 775                 780
```

| | | | | | | | | | | | | | | |
|---|---|---|---|---|---|---|---|---|---|---|---|---|---|---|
|Val|Leu|Ile|Arg|Glu|Phe|Trp|Glu|Ile|Val|His|Ser|Phe|Thr|Asp|Glu|
|785| | | | |790| | | | |795| | | | |800|

Gln Lys Arg Leu Phe Leu Gln Phe Thr Thr Gly Thr Asp Arg Ala Pro
                    805                     810                 815

Val Gly Gly Leu Gly Lys Leu Lys Met Ile Ile Ala Lys Asn Gly Pro
                    820                     825                 830

Asp Thr Glu Arg Leu Pro Thr Ser His Thr Cys Phe Asn Val Leu Leu
                    835                     840                 845

Leu Pro Glu Tyr Ser Ser Lys Glu Lys Leu Lys Glu Arg Leu Leu Lys
                    850                     855                 860

Ala Ile Thr Tyr Ala Lys Gly Phe Gly Met Leu
865                 870                 875

<210> SEQ ID NO 15
<211> LENGTH: 2970
<212> TYPE: DNA
<213> ORGANISM: Homo sapiens

<400> SEQUENCE: 15

```
tttttccgga taaggaagcg cgggtcccgc atgagccccg gcggtggcgg cagcgaaaga      60
gaacgaggcg gtggcgggcg gaggcggcgg gcgagggcga ctacgaccag tgaggcggcc     120
gccgcagccc aggcgcgggg gcgacgacag gttaaaaatc tgtaagagcc tgattttaga     180
attccaccagc tcctcagaag tttggcgaaa tatgagttat taagcctacg ctcagatcaa    240
ggtagcagct agactggtgt gacaacctgt ttttaatcag tgactcaaag ctgtgatcac     300
cctgatgtca ccgaatggcc acagcttgta aagatcagg agaacctcag tctgacgaca      360
ttgaagctag ccgaatgaag cgagcagctg caaagcatct aatagaacgc tactaccacc    420
agttaactga gggctgtgga aatgaagcct gcacgaatga gttttgtgct tcctgtccaa     480
cttttcttcg tatggataat aatgcagcag ctattaaagc cctcgagctt tataagatta    540
atgcaaaact ctgtgatcct catccctcca agaaaggagc aagctcagct taccttgaga    600
actcgaaagg tgccccccaac aactcctgct ctgagataaa aatgaacaag aaaggcgcta    660
gaattgattt taaagatgtg acttacttaa cagaagagaa ggtatatgaa attcttgaat    720
tatgtagaga aagagaggat tattcccctt taatccgtgt tattggaaga gttttttcta    780
gtgctgaggc attggtacag agcttccgga agttaaaaca acacaccaag gaagaactga    840
aatctcttca agcaaaagat gaagacaaag atgaagatga aaggaaaaa gctgcatgtt     900
ctgctgctgc tatggaagaa gactcagagg catcttcctc aaggataggt gatagctcac    960
agggagacaa caatttgcaa aaattaggcc ctgatgatgt gtctgtggat attgatgcca  1020
ttagaagggt ctacaccaga ttgctctcta atgaaaaaat tgaaactgcc tttctcaatg  1080
cacttgtata tttgtcacct aacgtggaat gtgacttgac gtatcacaat gtatactctc  1140
gagatcctaa ttatctgaat ttgttcatta tcgtaatgga gaatagaaat ctccacagtc   1200
ctgaatatct ggaaatggct ttgccattat tttgcaaagc gatgagcaag ctacccttg   1260
cagcccaagg aaaactgatc agactgtggt ctaaatacaa tgcagaccag attcggagaa   1320
tgatggagac atttcagcaa cttattactt ataaagtcat aagcaatgaa tttaacagtc   1380
gaaatctagt gaatgatgat gatgccattg ttgctgcttc gaagtgcttg aaaatggttt   1440
actatgcaaa tgtagtggga ggggaagtgg acacaaatca caatgaagaa gatgatgaag   1500
agcccatccc tgagtccagc gagctgacac ttcaggaact tttgggagaa gaagaagaa    1560
acaagaaagg tcctcgagtg gaccccctgg aaactgaact tggtgttaaa accctggatt   1620
```

```
gtcgaaaacc acttatccct tttgaagagt ttattaatga accactgaat gaggttctag    1680
aaatggataa agattatact tttttcaaag tagaaacaga gaacaaattc tcttttatga    1740
catgtccctt tatattgaat gctgtcacaa agaatttggg attatattat gacaatagaa    1800
ttcgcatgta cagtgaacga agaatcactg ttctctacag cttagttcaa ggacagcagt    1860
tgaatccata tttgagactc aaagttagac gtgaccatat catagatgat gcacttgtcc    1920
ggctagagat gatcgctatg gaaaatcctg cagacttgaa gaagcagttg tatgtggaat    1980
ttgaaggaga acaaggagtt gatgagggag gtgtttccaa agaattttt cagctggttg     2040 tggaggaaat cttcaatcca gatattggta tgttcacata cgatgaatct acaaaattgt    2100
tttggtttaa tccatcttct tttgaaactg agggtcagtt tactctgatt ggcatagtac    2160
tgggtctggc tatttacaat aactgtatac tggatgtaca ttttcccatg gttgtctaca    2220
ggaagctaat ggggaaaaaa ggaacttttc gtgacttggg agactctcac ccagttctat    2280
atcagagttt aaaagattta ttggagtatg aagggaatgt ggaagatgac atgatgatca    2340 cttccagat atcacagaca gatctttttg gtaacccaat gatgtatgat ctaaaggaaa     2400
atggtgataa aattccaatt acaaatgaaa acaggaagga atttgtcaat ctttattctg    2460
actacattct caataaatca gtagaaaaac agttcaaggc ttttcggaga ggttttcata    2520
tggtgaccaa tgaatctccc ttaaagtact tattcagacc agaagaaatt gaattgctta    2580
tatgtggaag ccggaatcta gatttccaag cactagaaga aactacagaa tatgacggtg    2640
gctataccag ggactctgtt ctgattaggg agttctggga aatcgttcat tcatttacag    2700
atgaacagaa aagactcttc ttgcagttta caacgggcac agacagagca cctgtgggag    2760
gactaggaaa attaaagatg attatagcca aaaatggccc agacacagaa aggttaccta    2820
catctcatac ttgcttaat gtgcttttac ttccggaata ctcaagcaaa gaaaaactta    2880
aagagagatt gttgaaggcc atcacgtatg ccaaaggatt tggcatgctg taaaacaaaa    2940
caaaacaaaa taaaacaaaa aaaaggaagg                                     2970
```

What is claimed is:

1. A therapeutically effective amount of a ubiquitin protein ligase E3A (UBE3A) adeno-associated viral (AAV) vector for treating disturbances in synaptic function associated with a UBE3A deficiency disease comprising:
   a transcription initiation sequence;
   a UBE3A sequence disposed downstream of the transcription initiation sequence, wherein the UBE3A sequence is SEQ ID No. 12 or a nucleotide sequence possessing at least 95% sequence identity thereto;
   a secretion sequence disposed downstream of the transcription initiation sequence and upstream of the UBE3A sequence, wherein the secretion sequence is SEQ ID NO: 2, SEQ ID NO: 9, SEQ ID NO: 9, SEQ ID NO: 10, or a homologous sequence; and
   a cell uptake sequence disposed downstream of the transcription initiation sequence and between the secretion sequence and the UBE3A sequence, wherein the cell uptake sequence is SEQ ID NO: 4, a cDNA of SEQ ID NO: 5, or a homologous sequence,
   said amount of vector being effective at expressing a secreted E6-associated protein (E6-AP) and rescuing E6-AP function in non-transduced cerebral cells in a subject with the UBE3A deficiency disease.

2. The vector of claim 1, wherein the transcription initiation sequence is a cytomegalovirus chicken-beta actin hybrid promoter, or human ubiquitin c promoter.

3. The vector of claim 2, further comprising a cytomegalovirus immediate-early enhancer sequence disposed upstream of the transcription initiation sequence.

4. The vector of claim 1, further comprising a woodchuck hepatitis post-transcriptional regulatory element.

5. The vector of claim 1, wherein the secretion sequence is SEQ ID NO: 9.

6. The vector of claim 1, wherein the UBE3A deficiency disease is selected from Angelman syndrome, Prader-Willi syndrome, and Huntington's disease.

7. The vector of claim 1, wherein the vector is formulated for injection into the hippocampus or ventricle.

8. The vector of claim 1, wherein the therapeutically effective amount is a dose in the range of about $5.55 \times 10^{11}$ to about $2.86 \times 10^{12}$ genomes/g brain mass.

9. The vector of claim 1, wherein the disturbances in synaptic function are disturbances in long-term synaptic plasticity.

10. A method of treating disturbances in synaptic function in a patient with a UBE3A deficiency disease, comprising:
    administering the vector of claim 1 to the brain of a patient suffering from the UBE3A deficiency disease;
    wherein the UBE3A deficiency disease is Angelman syndrome, Prader-Willi syndrome, or Huntington's disease.

11. The method of claim 10, wherein the administering a vector to the brain comprises injecting the vector into the brain.

12. The method of claim 11, wherein the vector is injected into the hippocampus or ventricle.

13. The method of claim 12, wherein the vector is injected bilaterally.

14. The method of claim 10, wherein the vector is administered at about $5.55 \times 10^{11}$ to about $2.86 \times 10^{12}$ genomes/g brain mass.

15. The method of claim 10, wherein the vector is administered at $5.55 \times 10^{11}$ to $2.86 \times 10^{12}$ genomes/g brain mass, $2.86 \times 10^{12}$ genomes/g brain mass, or $5.55 \times 10^{11}$ genomes/g brain mass.

16. The method of claim 10, wherein the disturbances in synaptic function are disturbances in long-term synaptic plasticity.

\* \* \* \* \*